(12) United States Patent
Regueira et al.

(10) Patent No.: US 11,407,986 B2
(45) Date of Patent: Aug. 9, 2022

(54) ENZYME VARIANTS AND POLYNUCLEOTIDES ENCODING SAME

(71) Applicant: Novozymes A/S, Bagsvaerd (DK)

(72) Inventors: Torsten Bak Regueira, Vaerloese (DK); Bitten Plesner, Copenhagen (DK); Thomas Holberg Blicher, Copenhagen (DK); Anne Dorte Houg, Copenhagen (DK); Sofia Arnehed, Tygelsjo (SE); Lars Lehmann Hylling Christensen, Alloeroed (DK); Carsten Andersen, Vaerloese (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 16/062,492

(22) PCT Filed: Dec. 29, 2016

(86) PCT No.: PCT/EP2016/082828
§ 371 (c)(1),
(2) Date: Jun. 14, 2018

(87) PCT Pub. No.: WO2017/114891
PCT Pub. Date: Jul. 6, 2017

(65) Prior Publication Data
US 2018/0371441 A1   Dec. 27, 2018

(30) Foreign Application Priority Data

Dec. 30, 2015  (EP) .................................... 15203051
May 3, 2016   (EP) .................................... 16168114

(51) Int. Cl.
| | | |
|---|---|---|
| *C12N 9/26* | (2006.01) | |
| *C11D 3/386* | (2006.01) | |
| *C12N 1/14* | (2006.01) | |
| *C12N 1/20* | (2006.01) | |
| *C12N 15/52* | (2006.01) | |
| *C12N 15/63* | (2006.01) | |
| *C12N 9/28* | (2006.01) | |

(52) U.S. Cl.
CPC ............ *C12N 9/2414* (2013.01); *C11D 3/386* (2013.01); *C12N 1/14* (2013.01); *C12N 1/20* (2013.01); *C12N 9/2417* (2013.01); *C12N 15/52* (2013.01); *C12N 15/63* (2013.01); *C12Y 302/01001* (2013.01)

(58) Field of Classification Search
None
See application file for complete search history.

(56) References Cited

U.S. PATENT DOCUMENTS

| | | |
|---|---|---|
| 6,204,232 B1 | 3/2001 | Borchert |
| 2008/0193999 A1* | 8/2008 | Andersen ............ C12N 9/2417 435/201 |
| 2011/0097778 A1 | 4/2011 | Power et al. |
| 2014/0206026 A1 | 7/2014 | Kaasgaard |
| 2017/0044509 A1* | 2/2017 | Jenewein ............ C12N 9/2417 |
| 2018/0371441 A1* | 12/2018 | Regueira ............ C11D 3/386 |

FOREIGN PATENT DOCUMENTS

| | | |
|---|---|---|
| DE | 102005062984 A1 | 7/2007 |
| WO | 1996/23873 A1 | 8/1996 |
| WO | 2000/60060 A2 | 10/2000 |
| WO | 2001/66712 A2 | 9/2001 |
| WO | 2006/002643 A2 | 1/2006 |
| WO | 2011100410 A2 | 8/2011 |
| WO | 2015121133 A1 | 8/2015 |
| WO | 2015/149641 A1 | 10/2015 |
| WO | 2015/162038 A1 | 10/2015 |

OTHER PUBLICATIONS

PIR Accession No. G98247, published Oct. 22, 2001 (Year: 2001).*
PIR Accession No. AH2079, published Dec. 14, 2001 (Year: 2001).*
PIR Accession No. S15713, published Feb. 18, 1994 (Year: 1994).*
Geneseq Accession No. AXT20195, published Mar. 18, 2010 (Year: 2010).*
Geneseq Accession No. AYY97812, published Aug. 21, 2000 (Year: 2000).*
Tsukamoto et al, 1988, Biochem Biophys Res Com, vol. 151, pp. 25-31.

* cited by examiner

*Primary Examiner* — Richard C Ekstrom
(74) *Attorney, Agent, or Firm* — Yoshimi Barron

(57) ABSTRACT

The present invention relates to polypeptide having alpha-amylase activity. The present invention also relates to polynucleotides encoding the polypeptides; nucleic acid constructs, vectors, and host cells comprising the polynucleotides; and methods of using the polypeptides.

42 Claims, No Drawings
Specification includes a Sequence Listing.

ENZYME VARIANTS AND POLYNUCLEOTIDES ENCODING SAME

CROSS-REFERENCE TO RELATED APPLICATIONS

This application is a 35 U.S.C. 371 national application of PCT/EP2016/082828 filed Dec. 29, 2016 which claims priority or the benefit under 35 U.S.C. 119 of European application nos. 15203051.6 and 16168114.3 filed Dec. 30, 2015 and May 3, 2016, the contents of which are fully incorporated herein by reference.

REFERENCE TO A SEQUENCE LISTING

This application comprises a Sequence Listing in computer readable form, which is incorporated herein by reference.

BACKGROUND OF THE INVENTION

Field of the Invention

The present invention relates to alpha-amylase variants (i.e. polypeptides having alpha-amylase activity), nucleic acids encoding the alpha-amylases, methods of producing the alpha-amylases, compositions comprising the alpha-amylases and methods of using the alpha-amylases.

Description of the Related Art

Alpha-amylases (alpha-1,4-glucan-4-glucanohydrolases, E.C. 3.2.1.1) constitute a group of enzymes which catalyse hydrolysis of starch and other linear and branched 1,4-gluosidic oligo- and polysaccharides.

There is a long history of industrial use of alpha-amylases in several known applications such as detergent, baking, brewing, starch liquefaction and saccharification e.g. in preparation of high fructose syrups or as part of ethanol production from starch. These and other applications of alpha-amylases are known and utilize alpha-amylases derived from microorganisms, in particular bacterial alpha-amylases.

Bacillus alpha-amylases, such as Termamyl, AA560 (SEQ ID NO: 2; see also WO 2000/060060) and SP707 (SEQ ID NO: 8; see also Tsukamoto et al., 1988, Biochem. Biophys. Res. Comm. 151:25-31) form a particular group of alpha-amylases that have found use in detergents. These amylases have been modified to improve the stability in detergents. For example, WO 96/23873 discloses deletion mutants of alpha-amylases SP690, SP722 (SEQ ID NO: 5) and SP707 (SEQ ID NO: 8) (see also SEQ ID NOs: 1, 2 and 7 of WO 96/23873) to improve the stability of these amylases. WO 96/23873 further discloses substitution mutants to stabilize the amylases towards oxidation. Additional alpha-amylase mutants with improved properties are disclosed in WO 2006/002643 and WO 01/66712.

Thus, it is known to modify naturally-occurring amylases to improve certain properties.

It is an object of the present invention to provide polypeptides having alpha-amylase activity (alpha-amylases) which have enhanced wash performance, especially at high temperature (for example at 40° C. or higher).

SUMMARY OF THE INVENTION

The present invention relates to polypeptides having alpha-amylase activity corresponding to variants of an alpha-amylase derived from Bacillus. In particular, the polypeptides of the invention comprise or consist of an amino acid sequence of SEQ ID NO:1 in which one or more of the amino acids are mutated (for example, by substitution or deletion), such that the polypeptide exhibits enhanced wash performance (especially at temperatures of 40° C. or higher).

The present invention also relates to polynucleotides encoding the variant alpha-amylase polypeptides; nucleic acid constructs, vectors, and host cells comprising the polynucleotides; and methods of producing the variant alpha-amylase polypeptides.

The present invention also relates to detergent compositions comprising the variant alpha-amylase polypeptides and uses of the same in domestic and industrial cleaning processes, such as the laundry cleaning and dishwashing.

Definitions

Alpha-amylase: The term "alpha-amylase" (alpha-1,4-glucan-4-glucanohydrolase, E.C. 3.2.1.1) constitutes a group of enzymes which catalyse hydrolysis of starch and other linear and branched 1,4-gluosidic oligo- and polysaccharides. For purposes of the present invention, alpha-amylase activity is determined according to the procedure described in Example 1. In one aspect, the variants of the present invention have at least 20%, e.g., at least 40%, at least 50%, at least 60%, at least 70%, at least 80%, at least 90%, at least 95%, or at least 100% of the alpha-amylase activity of the mature polypeptide of SEQ ID NO: 1.

Amino acid: The term 'amino acid' as used herein includes the standard twenty genetically-encoded amino acids and their corresponding stereoisomers in the 'D' form (as compared to the natural 'L' form), omega-amino acids other naturally-occurring amino acids, unconventional amino acids (e.g. α,α-disubstituted amino acids, N-alkyl amino acids, etc.) and chemically derivatised amino acids. Chemical derivatives of one or more amino acids may be achieved by reaction with a functional side group. Such derivatised molecules include, for example, those molecules in which free amino groups have been derivatised to form amine hydrochlorides, p-toluene sulphonyl groups, carboxybenzoxy groups, t-butyloxycarbonyl groups, chloroacetyl groups or formyl groups. Free carboxyl groups may be derivatised to form salts, methyl and ethyl esters or other types of esters and hydrazides. Free hydroxyl groups may be derivatised to form O-acyl or O-alkyl derivatives. Also included as chemical derivatives are those peptides which contain naturally occurring amino acid derivatives of the twenty standard amino acids. For example: 4-hydroxyproline may be substituted for proline; 5-hydroxylysine may be substituted for lysine; 3-methylhistidine may be substituted for histidine; homoserine may be substituted for serine and ornithine for lysine. Derivatives also include peptides containing one or more additions or deletions as long as the requisite activity is maintained. Other included modifications are amidation, amino terminal acylation (e.g. acetylation or thioglycolic acid amidation), terminal carboxylamidation (e.g. with ammonia or methylamine), and the like terminal modifications.

When an amino acid is being specifically enumerated, such as 'alanine' or 'Ala' or 'A', the term refers to both L-alanine and D-alanine unless explicitly stated otherwise. Other unconventional amino acids may also be suitable components for polypeptides of the present invention, as long as the desired functional property is retained by the polypeptide. For the peptides shown, each encoded amino acid residue, where appropriate, is represented by a single letter designation, corresponding to the trivial name of the conventional amino acid. In one embodiment, the polypeptides of the invention comprise or consist of L-amino acids.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a variant. The boundaries of the coding sequence are generally determined by an open reading frame, which begins with a start codon such as ATG, GTG or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a variant of the present invention. Each control sequence may be native (i.e., from the same gene) or foreign (i.e., from a different gene) to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

Enhanced wash performance: The terms "enhanced wash performance" or "improved wash performance" mean the ability of the polypeptide of the invention to provide a cleaning effect (e.g. stain removal) in a wash process, such as laundry or dishwashing, is improved compared to that of the parent alpha amylase of SEQ ID NO:1. Wash performance may be determined using methods well known in the art, such as using an automatic mechanical stress assay (AMSA) or automatic dish wash (ADW) (see Examples 2 and 3). It will be appreciated by persons skilled in the art that the enhanced wash performance may be achieved under only some or perhaps all wash conditions, for example at wash temperatures of 40° C. or higher (such as at 40° C. and/or at 50° C.) and/or with or without the presence of bleach.

Expression: The term "expression" includes any step involved in the production of a variant including, but not limited to, transcription, post-transcriptional modification, translation, post-translational modification, and secretion.

Expression vector: The term "expression vector" means a linear or circular DNA molecule that comprises a polynucleotide encoding a variant and is operably linked to control sequences that provide for its expression.

Fragment: The term "fragment" means a polypeptide having one or more (e.g., several) amino acids absent from the amino and/or carboxyl terminus of the mature polypeptide of SEQ ID NO:1; wherein the fragment has alpha-amylase activity. In one aspect, a fragment contains at least 200 contiguous amino acid residues of SEQ ID NO: 1, for example at least 300 contiguous amino acid residues, or at least 350 contiguous amino acid residues, or at least 400 contiguous amino acid residues, or at least 450 contiguous amino acid residues of SEQ ID NO: 1.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Improvement factor: The term "improvement factor" means a quantitative way of calculating the improvement of a particular property of a variant according to the present invention. Determination of the Improvement Factor may be according to the following formula:

$$\frac{\text{Intensity value of variant} - \text{Intensity value of blank}}{\text{Intensity value of parent} - \text{Intensity value of blank}}$$

Other formulas may be used to determine the Improvement Factor. The skilled person knows the presently presented formula as well as alternative ways of calculating the Improvement Factor.

According to the present invention, a value of 1.0 corresponds to the specific activity observed for the parent alpha-amylase. A value above 1.0 indicates an improvement of specific activity of the variant tested compared to the parent alpha-amylase. Accordingly, any value of >1.0 is indicative for improvement of property, such as specific activity, of the variant compared to the parent alpha-amylase. A value of 1.0 indicates that the property of the variant is at least on par with the parent alpha-amylase.

Isolated: The term "isolated" means a substance in a form or environment which does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

Mature polypeptide: The term "mature polypeptide" means a polypeptide in its final form following translation and any post-translational modifications, such as N-terminal processing, C-terminal truncation, glycosylation, phosphorylation, etc. It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes a mature polypeptide having alpha-amylase activity.

Mutation: The term "mutation", in the context of the polypeptides of the invention, means that one or more amino acids within the reference amino acid sequence (i.e. SEQ ID NO:1) are altered by substitution with a different amino acid or by deletion. Additionally, the mutation may correspond to an insertion of one or more extra amino acid(s) within the reference amino acid sequence.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Parent or parent alpha-amylase: The term "parent" or "parent alpha-amylase" means the alpha-amylase of SEQ ID NO:1 (commercialised by Novozymes NS under the trade name "Stainzyme® Plus"; see WO 2006/002643).

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used may be gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−
Total Number of Gaps in Alignment)

Alternatively, the parameters used may be gap open penalty of 10, gap extension penalty of 0.5, and the EDNA-FULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of
Alignment−Total Number of Gaps in Alignment)

Subsequence: The term "subsequence" means a polynucleotide having one or more (e.g., several) nucleotides absent from the 5' and/or 3' end of a mature polypeptide coding sequence; wherein the subsequence encodes a fragment having alpha-amylase activity.

Variant: The term "variant" means a polypeptide having alpha-amylase activity comprising a mutation, i.e., a substitution, insertion, and/or deletion, at one or more (e.g., several) positions relative to the 'parent' alpha-amylase of SEQ ID NO:1. A substitution means replacement of the amino acid occupying a position with a different amino acid; a deletion means removal of the amino acid occupying a position; and an insertion means adding an amino acid adjacent to and immediately following the amino acid occupying a position The variants of the present invention have at least 20%, e.g., at least 40%, at least 50%, at least 60%, at least 70%, at least 80%, at least 90%, at least 95%, or at least 100% of the alpha-amylase activity of the mature polypeptide of SEQ ID NO: 1.

Wild-type alpha-amylase: The term "wild-type" alpha-amylase means an alpha-amylase expressed by a naturally occurring microorganism, such as a bacterium, yeast, or filamentous fungus found in nature.

Conventions for Designation of Variants

The polypeptides of the invention having alpha-amylase activity correspond to variants of an alpha-amylase derived from *Bacillus*, as shown in SEQ ID NO: 1 (which is marketed by Novozymes NS under the name Stainzyme Plus™).

[SEQ ID NO: 1]
HHNGTNGTLM QYFEWYLPND GNHWNRLRSD ASNLKDKGIS

AVWIPPAWKG ASQNDVGYGA YDLYDLGEFN QKGTIRTKYG

TRNQLQAAVN ALKSNGIQVY GDVVMNHKGG ADATEMVKAV

EVNPNNRNQE VSGEYTIEAW TKFDFPGRAN THSNFKWRWY

HFDGVDWDQS RKLNNRIYKF RTKAWDWEVD TEFGNYDYLL

YADIDMDHPE VVNELRNWGV WYTNTLGLDG FRIDAVKHIK

YSFTRDWINH VRSAIGKNMF AVAEFWKNDL GAIENYLNKT

NWNHSVFDVP LHFNLYYASK SGGNYDMRQI FNGTVVQKHP

THAVTFVDNH DSQPEESLES FVREWFKPLA YALTLTREQG

YPSVFYGDYY GIPTHGVPAM KSKIDPILEA RQKYAYGRQN

DYLDHHNIIG WTREGNTAHP NSGLATIMSD GAGGNKWMFV

GRNKAGQVWT DITGNKAGTV TINADGWGNF SVNGGSVSIW VNK

The variant, i.e. mutated, amino acids in the polypeptides of the invention are defined by reference to the amino acid numbering of SEQ ID NO: 2 (which corresponds to the mature protein AA560 of *B. subtilis*). The amino acid sequence differences relative to SEQ ID NO:1 are shown below in bold, underlined.

[SEQ ID NO: 2]
HHNGTNGTMMQYFEWYLPNDGNHWNRLRSDASNLKDKGISAVWIPPAWKG

ASQNDVGYGAYDLYDLGEFNQKGTIRTKYGTRNQLQAAVNALKSNGIQVY

GDVVMNHKGGADATEMVRAVEVNPNNRNQEVSGEYTIEAWTKFDFPGRGN

THSNFKWRWYHFDGVDWDQSRKLNNRIYKFRGDGKGWDWEVDTENGNYDY

LMYADIDMDHPEVVNELRNWGVWYTNTLGLDGFRIDAVKHIKYSFTRDWI

NHVRSATGKNMFAVAEFWKNDLGAIENYLNKTNWNHSVFDVPLHYNLYNA

SKSGGNYDMRQIFNGTVVQRHPMHAVTFVDNHDSQPEEALESFVEEWFKP

LAYALTTTREQGYPSVFYGDYYGIPTHGVPAMKSKIDPILEARQKYAYGR

QNDYLDHHNIIGWTREGNTAHPNSGLATIMSDGAGGNKWMFVGRNKAGQV

WTDITGNRAGTVTINADGWGNFSVNGGSVSIWVNK

Consequently, amino acid positions 1 to 182 in SEQ ID NO:2 correspond to the same numbering in SEQ ID NO:1, amino acid positions 183 and 184 of SEQ ID NO: 2 are absent in SEQ ID NO:1 and amino acid positions 185 to 485 of SEQ ID NO:2 correspond to positions 183 to 483 of SEQ ID NO:1, respectively.

Thus, for purposes of the present invention, the mature polypeptide disclosed in SEQ ID NO: 2 is used to determine the corresponding amino acid residue in another alpha-amylase polypeptide. The amino acid sequence of another alpha-amylase is aligned with the mature polypeptide disclosed in SEQ ID NO: 2, and based on the alignment, the amino acid position number corresponding to any amino acid residue in the mature polypeptide disclosed in SEQ ID NO: 2 is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix.

Identification of the corresponding amino acid residue in another alpha-amylase can be determined by an alignment of multiple polypeptide sequences using several computer programs including, but not limited to, MUSCLE (multiple sequence comparison by log-expectation; version 3.5 or later; Edgar, 2004, *Nucleic Acids Research* 32: 1792-1797), MAFFT (version 6.857 or later; Katoh and Kuma, 2002, *Nucleic Acids Research* 30: 3059-3066; Katoh et al., 2005, *Nucleic Acids Research* 33: 511-518; Katoh and Toh, 2007, *Bioinformatics* 23: 372-374; Katoh et al., 2009, *Methods in Molecular Biology* 53709-64; Katoh and Toh, 2010, *Bioinformatics* 26: 1899-1900), and EMBOSS EMMA employing ClustalW (1.83 or later; Thompson et al., 1994, *Nucleic Acids Research* 22: 4673-4680), using their respective default parameters.

When the other alpha-amylase has diverged from the mature polypeptide of SEQ ID NO: 2 such that traditional sequence-based comparison fails to detect their relationship (Lindahl and Elofsson, 2000, *J. Mol. Biol.* 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the polypeptide has one or more representatives in the protein structure databases. Programs such as GenTHREADER (Jones, 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. Two or more protein structures can be aligned using a variety of algorithms such as the distance alignment matrix (Holm and Sander, 1998, *Proteins* 33: 88-96) or combinatorial extension (Shindyalov and Bourne, 1998, *Protein Engineering* 11: 739-747), and implementation of these algorithms can additionally be utilized to query structure databases with a structure of interest in order to discover possible structural homologs (e.g., Holm and Park, 2000, *Bioinformatics* 16: 566-567).

In describing the alpha-amylase variants of the present invention, the nomenclature described below is adapted for ease of reference. The accepted IUPAC single letter or three letter amino acid abbreviation is employed.

Substitutions: For an amino acid substitution, the following nomenclature is used: Original amino acid, position, substituted amino acid. Accordingly, the substitution of threonine at position 226 with alanine is designated as "Thr226Ala" or "T226A". Multiple mutations are separated by addition marks ("+"), e.g., "Gly205Arg+Ser411Phe" or "G205R+S411F", representing substitutions at positions 205 and 411 of glycine (G) with arginine (R) and serine (S) with phenylalanine (F), respectively.

Deletions: For an amino acid deletion, the following nomenclature is used: Original amino acid, position, *. Accordingly, the deletion of glycine at position 195 is designated as "Gly195*" or "G195*". Multiple deletions are separated by addition marks ("+"), e.g., "Gly195*+Ser411*" or "G195*+S411*".

Insertions: For an amino acid insertion, the following nomenclature is used: Original amino acid, position, original amino acid, inserted amino acid. Accordingly the insertion of lysine after glycine at position 195 is designated "Gly195GlyLys" or "G195GK". An insertion of multiple amino acids is designated [Original amino acid, position, original amino acid, inserted amino acid #1, inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
|---|---|
| 195 | 195 195a 195b |
| G | G - K - A |

Multiple alterations: Variants comprising multiple alterations are separated by addition marks ("+"), e.g., "Arg170Tyr+Gly195Glu" or "R170Y+G195E" representing a substitution of arginine and glycine at positions 170 and 195 with tyrosine and glutamic acid, respectively.

Different alterations: Where different alterations can be introduced at a position, the different alterations are separated by a comma, e.g., "Arg170Tyr,Glu" represents a substitution of arginine at position 170 with tyrosine or glutamic acid. Thus, "Tyr167Gly,Ala+Arg170Gly,Ala" designates the following variants: "Tyr167Gly+Arg170Gly", "Tyr167Gly+Arg170Ala", "Tyr167Ala+Arg170Gly", and "Tyr167Ala+Arg170Ala".

DETAILED DESCRIPTION OF THE INVENTION

Polypeptides Having Alpha-Amylase Activity

The present invention relates to variant alpha-amylase polypeptides, comprising a mutation at one or more (e.g., several) positions within the amino acid sequence of the mature polypeptide of SEQ ID NO: 1, wherein the variant exhibits an enhanced wash performance compared to the polypeptide of SEQ ID NO: 1.

In one embodiment the invention relates to a polypeptide comprising a variant amino acid sequence of SEQ ID NO: 1, wherein the polypeptide has alpha-amylase activity and exhibits an enhanced wash performance compared to the polypeptide of SEQ ID NO: 1.

In one embodiment, the variant amino acid sequence comprises a mutation at amino acid position 167 of SEQ ID NO: 1.

Thus, in one embodiment, the variant amino acid sequence comprises a substitution at amino acid position 167 of SEQ ID NO: 1, such as W167Y.

The amino acid sequence of the parent alpha-amylase is shown below:

[SEQ ID NO: 1]
HHNGTNGTLM QYFEWYLPND GNHWNRLRSD ASNLKDKGIS

AVWIPPAWKG ASQNDVGYGA YDLYDLGEFN QKGTIRTKYG

TRNQLQAAVN ALKSNGIQVY GDVVMNHKGG ADATEMVKAV

EVNPNNRNQE VSGEYTIEAW TKFDFPGRAN THSNFKWRWY

HFDGVDWDQS RKLNNRIYKF RTKAWDWEVD TEFGNYDYLL

YADIDMDHPE VVNELRNWGV WYTNTLGLDG FRIDAVKHIK

YSFTRDWINH VRSAIGKNMF AVAEFWKNDL GAIENYLNKT

NWNHSVFDVP LHFNLYYASK SGGNYDMRQI FNGTVVQKHP

THAVTFVDNH DSQPEESLES FVREWFKPLA YALTLTREQG

YPSVFYGDYY GIPTHGVPAM KSKIDPILEA RQKYAYGRQN

DYLDHHNIIG WTREGNTAHP NSGLATIMSD GAGGNKWMFV

GRNKAGQVWT DITGNKAGTV TINADGWGNF SVNGGSVSIW VNK

The polypeptides of the invention represent variants of the parent alpha amylase of SEQ ID NO: 1, which variants exhibit enhanced wash performance in domestic and/or industrial cleaning processes, such as the laundry cleaning and dishwashing. Wash performance may be determined using methods well known in the art, such as using an automatic dish wash (ADW) (see Example 2) or an automatic mechanical stress assay (AMSA) (see Example 3).

In one embodiment, the polypeptide exhibits enhanced wash performance during high temperature washes, for example wherein the temperature is at least 40° C., such as at least 45° C., such as at least 50° C., such as at least 55° C., and such as at least 60° C.

In one embodiment, enhanced wash performance is assessed in an automatic dish wash (ADW) assay using melamine tiles stained with starch. Exemplary wash conditions for determining such enhanced wash performance of the polypeptides of the invention include:
 a. Model ADW detergent with bleach at 40° C. and a wash cycle of 10 min;
 b. Model ADW detergent without bleach at 40° C. and a wash cycle of 10 min;
 c. Model ADW detergent with bleach at 50° C. and a wash cycle of 20 min; and
 d. Model ADW detergent without bleach at 50° C. and a wash cycle of 20 min;
wherein said model ADW detergent comprises trisodium salt of methylglycinediacetic acid (such as Trilon M granules SG), sodium citrate, sodium carbonate, sodium silicate, sodium sulphate, polyphosphate and silicate scale inhibitor (such as Acusol 588G) and Surfac 23-6.5.

In addition to enhanced wash performance, it will be appreciated by persons skilled in the art that the polypeptides of the invention may also exhibit improvements in one or more of the following properties relative to the parent alpha amylase of SEQ ID NO:1:
 (i) Substrate specificity;
 (ii) Substrate binding;
 (iii) Specific activity;
 (iv) Thermal stability
 (v) pH stability profile;
 (vi) $Ca^{2+}$ dependency;
 (vii) Oxidation stability;
 (viii) Increased/decreased pI; and/or
 (ix) Sensitivity to surfactants.

Assays for determining the above properties of a polypeptide are described in WO 2006/002643, WO 2001/066712 and EP 2 264 460 A.

The polypeptides of the invention may be longer or shorter than the parent alpha-amylase of SEQ ID NO:1. Thus, the polypeptide may be 1000 or fewer amino acids in length, for example 900, 800, 700, 600, 500, 400, 300, 200, 175, 150, 125, 100 or fewer amino acids. In one embodiment, the polypeptide is between 400 and 600 amino acids in length, for example between 450 and 500, between 460 and 500, or between 470 and 490 amino acids in length.

The variant polypeptides of the invention comprise a mutation (i.e., a substitution, insertion, and/or deletion) at one or more amino acid positions relative to the 'parent' alpha-amylase of SEQ ID NO:1.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for alpha-amylase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

In one alternative or further embodiment, the polypeptide of the invention is a variant of the alpha-amylase of SEQ ID NO:1 having a mutation (such as a substitution, deletion, and/or insertion) at one or more positions corresponding to positions 10, 25, 30, 37, 40, 48, 51, 54, 64, 81, 86, 93, 98, 105, 108, 109, 113, 116, 118, 121, 130, 135, 138, 142, 167, 174, 175, 178, 182, 186, 187, 189, 195, 198, 202, 203, 206, 208, 210, 214, 218, 235, 238, 242, 243, 246, 247, 250, 255, 257, 259, 260, 261, 265, 267, 269, 270, 274, 275, 276, 281, 295, 298, 299, 311, 319, 320, 334, 339, 360, 365, 366, 383, 384, 385, 394, 398, 402, 404, 416, 434, 460, 469, 474, and 482, wherein numbering is according to the amino acid sequence set forth in SEQ ID NO: 2.

Thus, the polypeptide may comprise one or more of the following substitutions relative to the amino acid sequence of SEQ ID NO:2; M10L, N25K, D30N, K37H, K37L, K37M, K37R, K37V, S40T, W48F, A51Q, A51T, N54S, Y64W, T81S, Q86H, Q86I, Q86L, K93H, K93R, Q98R, M105Y, M105F, M105I, M105L, K108R, G109A, G109M, A113E, M116I, M116L, M116A, M116V, M116F, K118Q, K118H, K118N, K118R, E121H, E130H, E130Q, Y135H, E138Q, K142R, K142Q, W167Y, W167H, N174Q, N174*, N175Q, Y178W, T182G, A186D, A186G, W187Y, W189H, F195N, Y198F, L202M, Y203H, Y203N, Y203G, Y203F, I206L, M208F, M208L, M208V, H210N, V214R, V214T, V214I, R218N, I235V, I235L, I235M, V238T, V238A, K242P, Y243F, Y243M, T246V, T246I, T246L, T246M, R247K, I250L, I250V, S255K, I257A, K259N, N260D, M261L, M261A, A265G, F267Y, K269S, K269N, N270G, A274K, I275L, E276Q, K281H, F295Y, F295W, Y298W, Y298F, Y299W, Y299F, Q311T, Q311H, Q311R, Q319H, Q319R, K320H, K320R, S334T, S339A, E360F, S365M, S365C, V366I, K383Q, K383R, S384E, K385H, K385Q, K385R, Q394K, Y398W, N402Y, Y404W, E416L, A434D, G460E, W469F, V474C, and W482Y.

For example, the polypeptide of the invention may be selected from the group consisting of polypeptides of the amino acid sequence of SEQ ID NO:1 with the following mutations; E360F+S365C (i.e. a polypeptide having an amino acid sequence based on SEQ ID NO:1 but with mutations E360F and S365C), K37H+L202M, M261L, H210N, Y243F, K108R, V474C, G460E, T81S, K269S+ N270G+A274K, K37V+L202M, L202M+Q311R, N174Q+ L202M, K385H, K385Q, K385R, K383Q, K320H, K320R, E276Q, K93R, K93H, Q98R, K118Q, K118H, K118N, E130H, E130Q, E138Q, K142R, K142Q, E416L, Q394K, S384E, Y64W, K37R, D30N, F295Y, Y243M, Y178W, K281H, K269N, Y198F, Q311T, F195N, I257A, S255K, R247K, Y404W, Y398W, Q319H, Q319R, Q311H, Q311R, Y299W, N260D, K259N, Y299F, A434D, V366I, S365M, S339A, N174*, I235V, I250L, I250V, K37V, K37M, K37L, Y203H, S40T, W187Y, V238T, M105Y, M105F, M105I, I206L, T182G, M116I, Y135H, Y203N, Y203G, N25K, M116L, A265G, F295Y, A265G, K242P, V214R, M208F, Y198F, W482Y, V214T, V214I, M261A, M105F, M208L, M116A, N174Q, N174*+N175Q, I235L, A265G, M105L, K37H, Q311R, W469F, Y203F, G109A, N175Q, W48F, M116V, M116F, F295W, Y298W, M208V, M208F, M10L+ M261L, W187Y+M208L, Y298F, W167Y, W167H, W189H, F295Y, I235M, Y243F+F267Y, K37V+P45R+ K383R, D30N+N33D+K37V+K383R, W167Y+H210N+ S339A+V366I, S339A+V366I, W167Y+H210N+S339A, H210N+S339A, W167Y+H210N, W167Y+L202M+ H210N+Y299F+S339A+V366I, W167Y+H210N+Y243F+ S339A+V366I, W167Y+H210N+S339A+V366I+W482Y, M116F+W167Y+H210N+S339A+V366I, W48F+W167Y+ H210N+S339A+V366I, W167Y+H210N+Y299F+S339A+ V366I, W167Y+L202M+H210N+S339A+V366I, W167Y+ L202M+H210N+Y299F+S339A, W167Y+H210N+ S339A+W482Y, M116F+W167Y+H210N+S339A, W48F+ W167Y+H210N+S339A, W167Y+H210N+Y299F+S339A, W167Y+L202M+H210N+S339A, W167Y+L202M+ Y299F, W167Y+Y243F, M116F+W167Y, W48F+W167Y, W167Y+Y299F, W167Y+L202M, W167Y+H210N+ V366I, W167Y+V366I, H210N+V366I, W167Y+S339A+ V366I, D30N+N33D+K37V+L202M+K383R, D30N+ N33D+K37V+W48F+K383R, D30N+N33D+K37V+ M116F+K383R, D30N+N33D+K37V+K383R+W482Y, A51T, A51T+N54S, S334T, T246M, T246L, T246V, T246I, A186G, A51Q+G109M+Y203G, V238A+S334T, A51T+ L202M, L202M+T246L, A51T+N174Q+L202M+T246I+ S334T, A51T+N174Q+L202M+Q311R+S334T, I235L+ T246M+I250L, A186D+L202M, A186D+L202M+N270G+ N402Y, A186D+L202M+S339A, A186D+F195N+L202M, K37H+A51T+L202M, K37V+, A51T+L202M, A51T+ L202M+S365C, A51T+L202M+S339A, A51T+L202M+ Q311T, A51T+L202M+M261L, A51T+L202M+H210N, A51T+L202M+N270G, A51T+F195N+L202M, A51T+ L202M+Q319H, A51T+L202M+Q319R, A51T+L202M+ Q311H, A51T+L202M+R247K, A51T+L202M+Q311R, A51T+L202M+Y398W, A51T+L202M+Y299W, A51T+ K108R+L202M, A51T+L202M+Y243F, A51T+L202M+ V474C, A51T+L202M+G460E, N174Q+L202M+A265G+ Q311R+S334T, A51T+L202M+T246V+A265G+Q311R, A51T+L202M+A265G+Q311R, K37H+L202M+T246V+ S334T, L202M+T246V+S334T+E416L, L202M+T246V+ S334T+N402Y, L202M+T246V+S334T+V366I, L202M+ T246V+S334T+S365M, L202M+T246V+S334T+S365O, L202M+T246V+M261L+S334T, D30N+L202M+H210N+ T246V+S334T, L202M+T246V+N270G+S334T, F195N+ L202M+T246V+S334T, L202M+T246V+Q319H+S334T, L202M+T246V+Q319R+S334T, L202M+T246V+Q311H+ S334T, L202M+T246V+Q311R+S334T, L202M+T246V+ S334T+Y398W, L202M+T246V+K320H+S334T, L202M+ T246V+Y299W+S334T, L202M+T246V+K320R+S334T, L202M+Y243F+S334T, L202M+T246V+S334T+V474O, L202M+T246V+S334T+G460E, L202M+I235M+T246V+ S334T, K108R+L202M+T246V+S334T, A51T+A186D+ L202M+N270G+N402Y, A186D+L202M+N270G+ S339A+N402Y, A51T+A186D+L202M+N270G, A51T+ L202M+T246V+N270G, K37H+A51T+L202M+N270G, A51T+L202M+T246L+N270G, A51T+N174Q+L202M+ N270G, A51T+L202M+V238A+N270G, A51T+L202M+ A265G, A51T+L202M+M261L+N270G, A51T+L202M+ F267Y, A51T+L202M+I275L, A51T+L202M+N270G+ S365M, A51T+L202M+N270G+S365C, A51T+L202M+ N270G+Q311T, A51T+L202M+N270G+E416L, A51T+ L202M+N270G+N402Y, A51T+L202M+N270G+S365C, A51T+L202M+N270G+K383R, A51T+L202M+N270G+ V474C, A51T+L202M+N270G+G460E, A51T+Q86L+ L202M+N270G, A51T+Q86I+L202M+N270G, A51T+ A113E+L202M+N270G, A51T+K93H+L202M+N270G, A51T+K108R+L202M+N270G, A51T+L202M+K269N, A51T+L202M+Y243F+N270G, A51T+F195N+L202M+ N270G, A51T+L202M+R247K+N270G, A51T+L202M+ R218N+N270G, A51T+L202M+S255K+N270G, A51T+ L202M+I257A+N270G, A51T+L202M+V214I+R218N+

N270G, A51T+L202M+N270G+Q311H, A51T+L202M+ N270G+K320H, A51T+L202M+N270G+Y299W, A51T+ L202M+N270G+K320R, A51T+L202M+N270G+K383Q, A51T+K142R+L202M+N270G, A51T+E130Q+L202M+ N270G, A51T+K118N+L202M+N270G, A51T+E138Q+ L202M+N270G, A51T+K118H+L202M+N270G, A51T+ K118Q+L202M+N270G, A51T+Q86H+L202M+N270G, A51T+E121H+L202M+N270G, A51T+K118R+L202M+ N270G, K37H+A51T+N174Q+L202M+A265G+Q311R+ S334T, A51T+N174Q+L202M+T246I+Q311R+S334T, K37V+A51T+L202M+A265G+F267Y+Q311R+S334T, A51T+N174Q+L202M+A265G+F267Y+Q311R+S334T, A51G+L202M+Q311R+S334T, L202M+T246I+A265G+ F267Y+Q311R+S334T, A51T+L202M+F267Y+Q311R+ S334T+S365L, A51T+L202M+S365C, A51T+K108R+L202M, A51T+S365C, A51T+K108R, L202M+V238A+S334T, W48F+V238A+S334T, M116F+V238A+S334T, V238A+S334T+W482Y, Y243F+S334T, L202M+V238A+Y299F+S334T, L202M+T246V+N270G+S334T, W48F+K118H+V238A+S334T, W48F+L202M+V238A+S334T, A51T+A186N+L202M+N270G+S365C, W167Y+A186N+H210N+S339A+V366I, W48F+W167Y+A186N+H210N+S339A, W167Y+A186N+H210N+Y299F+S339A+V366I, L202M+T246V+N270G+S334T+S365C, A186N+L202M+T246V+N270G+S334T, and fragments thereof having alpha amylase activity, wherein numbering of amino acid positions is according to the amino acid sequence set forth in SEQ ID NO: 2.

In one embodiment, the polypeptide exhibits an enhanced wash performance corresponding to an Improvement Factor (IF) of at least 1.2 when the polypeptide is evaluated in an ADW assay with a detergent comprising bleach and at 40° C. for 10 min (for example, see Example 2). Suitable polypeptides may be a variant of SEQ ID NO:1 comprising a mutation at one or more positions corresponding to positions 37, 51, 93, 98, 108, 118, 167, 186, 202, 210, 235, 243, 246, 247, 250, 255, 259, 260, 261, 270, 299, 311, 319, 334, 339, 365, 385, 398, and 404, wherein numbering of amino acid positions is according to the amino acid sequence set forth in SEQ ID NO: 2. For example, the polypeptide may be selected from the group consisting of polypeptides of the amino acid sequence of SEQ ID NO:1 with the following mutations; K37H+L202M, M261L, Y243F, K385H, K385R, K93H, Q98R, K118Q, K118H, S255K, Y404W, Y398W, Q319R, Y299W, N260D, K259N, Y299F, S339A, S334T, A51T+L202M, I235L+T246M+I250L, K37V+A51T+L202M, A51T+L202M+5365C, A51T+L202M+Q311T, A51T+L202M+M261L, A51T+L202M+R247K, A51T+L202M+Y299W, A51T+K108R+L202M, A51T+L202M+Y243F, A51T+A186D+L202M+N270G, A51T+L202M+N270G+5365C, W167Y+A186N+H210N+S339A+V366I, W48F+W167Y+A186N+H210N+S339A, or W167Y+A186N+H210N+Y299F+S339A+V366, and fragments thereof having alpha amylase activity, wherein numbering of amino acid positions is according to the amino acid sequence set forth in SEQ ID NO: 2.

In another embodiment, the polypeptide exhibits an enhanced wash performance corresponding to an IF of at least 1.2 when the polypeptide is evaluated in an ADW assay with a detergent comprising bleach and at 50° C. for 20 min (for example, see Example 2). Suitable polypeptides may be a variant of SEQ ID NO:1 comprising a mutation at one or more positions corresponding to positions 30, 33, 37, 40, 48, 51, 81, 86, 93, 105, 108, 116, 118, 130, 138, 142, 167, 174, 175, 182, 186, 195, 198, 202, 206, 210, 235, 238, 243, 246, 247, 250, 255, 257, 259, 260, 261, 265, 266, 267, 269, 270, 299, 311, 319, 320, 334, 339, 360, 365, 366, 383, 385, 402, 416, 474, and 482, wherein numbering of amino acid positions is according to the amino acid sequence set forth in SEQ ID NO: 2. For example, the polypeptide may be selected from the group consisting of polypeptides of the amino acid sequence of SEQ ID NO:1 with the following mutations; K37H+L202M, E360F+5365C, M261L, H210N, Y243F, K108R, V474C, T81S, K385H, K385Q, K385R, K93R, K118Q, K118N, E130H, E130Q, E138Q, K37R, D30N, Y243M, K269N, Y198F, Q311T, F195N, I257A, S255K, R247K, Y404W, Y398W, Q319H, Q319R, Q311H, Q311R, Y299W, N260D, K259N, Y299F, V366I, S365M, S339A, I250L, I250V, K37M, S40T, V238T, M105F, M105I, I206L, T182G, M116I, M116L, N174Q, I235L, A265G, K37H, Q311R, N175Q, W48F, M116F, W167Y+H210N+S339A, H210N+S339A, W48F+W167Y+H210N+S339A, W48F+W167Y, W167Y+H210N+V366I, D30N+N33D+K37V+K383R+W482Y, A51T, S334T, T246M, T246L, T246V, T246I, A186G, V238A+S334T, A51T+L202M, A51T+N174Q+L202M+Q311R+S334T, I235L+T246M+I250L, L202M+T246V+S334T+E416L, D30N+L202M+H210N+T246V+S334T, L202M+T246V+N270G+S334T, F195N+L202M+T246V+S334T, L202M+T246V+K320R+S334T, L202M+Y243F+S334T, A51T+A186D+L202M+N270G+N402Y, A186D+L202M+N270G+S339A+N402Y, A51T+A186D+L202M+N270G, A51T+L202M+T246V+N270G, K37H+A51T+L202M+N270G, A51T+L202M+T246L+N270G, A51T+N174Q+L202M+N270G, A51T+L202M+V238A+N270G, A51T+L202M+A265G, A51T+L202M+M261L+N270G, A51T+L202M+F267Y, A51T+L202M+N270G+S365C, A51T+L202M+N270G+S365C, A51T+L202M+N270G+K383R, A51T+Q86I+L202M+N270G, A51T+K93H+L202M+N270G, A51T+K108R+L202M+N270G, A51T+L202M+N270G+K320H, A51T+L202M+N270G+K383Q, A51T+K142R+L202M+N270G, A51T+E130Q+L202M+N270G, A51T+E138Q+L202M+N270G, A51T+L202M+S365C, A51T+S365C, W48F+V238A+S334T, M116F+V238A+S334T, V238A+S334T+W482Y, Y243F+S334T, W48F+K118H+V238A+S334T, A51T+A186N+L202M+N270G+S3650, W167Y+A186N+H210N+S339A+V366I, W48F+W167Y+A186N+H210N+S339A, W167Y+A186N+H210N+Y299F+S339A+V366I, L202M+T246V+N270G+S334T+S365C, or A186N+L202M+T246V+N270G+S334T, and fragments thereof having alpha amylase activity, wherein numbering of amino acid positions is according to the amino acid sequence set forth in SEQ ID NO: 2.

In a further embodiment, the polypeptide exhibits an enhanced wash performance corresponding to an Improvement Factor (IF) of at least 1.2 when the polypeptide is evaluated in an ADW assay with a detergent without bleach and at 40° C. for 10 min (for example, see Example 2). Suitable polypeptides may be a variant of SEQ ID NO:1 comprising a mutation at one or more positions corresponding to positions 37, 48, 51, 64, 81, 108, 116, 167, 174, 186, 187, 189, 195, 198, 202, 208, 210, 235, 238, 243, 246, 250, 261, 265, 267, 269, 270, 275, 311, 319, 334, 339, 365, 366, 385, 460, and 474, wherein numbering of amino acid positions is according to the amino acid sequence set forth in SEQ ID NO: 2. For example, the polypeptide may be selected from the group consisting of polypeptides of the amino acid sequence of SEQ ID NO:1 with the following mutations; K37H+L202M, M261L, H210N, Y243F, K108R, G460E, T81S, N174Q+L202M, K385R, Y64W, Y243M, K269N, Y198F, S365M, S339A, W48F, M116V, M116F, W187Y+M208L, W167Y, W189H, W167Y+L202M+H210N+Y299F+S339A, W167Y+L202M+H210N+S339A, W167Y+L202M, V238A+S334T, A51T+L202M, L202M+

T246L, A51T+N174Q+L202M+T246I+S334T, I235L+ T246M+I250L, A186D+F195N+L202M, K37H+A51T+ L202M, K37V+A51T+L202M, A51T+L202M+S365C, A51T+L202M+Q311T, A51T+L202M+M261L, A51T+ L202M+Q319R, A51T+L202M+Q311H, A51T+K108R+ L202M, A51T+L202M+V474C, A51T+A186D+L202M+ N270G, K37H+A51T+L202M+N270G, A51T+L202M+ A265G, A51T+L202M+M261L+N270G, A51T+L202M+ F267Y, A51T+L202M+I275L, A51T+L202M+N270G+ S365C, W167Y+A186N+H210N+S339A+V366I, W48F+ W167Y+A186N+H210N+S339A, or W167Y+A186N+ H210N+Y299F+S339A+V366I, and fragments thereof having alpha amylase activity, wherein numbering of amino acid positions is according to the amino acid sequence set forth in SEQ ID NO: 2.

In a still further embodiment, the polypeptide exhibits an enhanced wash performance corresponding to an IF of at least 1.2 when the polypeptide is evaluated in an ADW assay with a detergent without bleach and at 50° C. for 20 min (for example, see Example 2). Suitable polypeptides may be a variant of SEQ ID NO:1 comprising a mutation at one or more positions corresponding to positions 30, 33, 37, 40, 48, 51, 86, 93, 108, 109, 113, 116, 118, 121, 130, 138, 142, 167, 174, 175, 182, 186, 195, 198, 202, 203, 210, 218, 235, 238, 243, 246, 247, 250, 255, 257, 259, 260, 261, 265, 267, 269, 270, 274, 275, 299, 311, 319, 320, 334, 339, 365, 366, 383, 385, 398, 402, 416, 404, 460, 474, and 482, wherein numbering of amino acid positions is according to the amino acid sequence set forth in SEQ ID NO: 2. For example, the polypeptide may be selected from the group consisting of polypeptides of the amino acid sequence of SEQ ID NO:1 with the following mutations; K269S+N270G+A274K, K37V+L202M, N174Q+L202M, K385H, K385R, K93H, K118Q, E130Q, E138Q, K37R, D30N, Y243M, K269N, Y198F, F195N, I257A, S255K, R247K, Y404W, Y398W, Q319H, Q319R, Q311H, Q311R, Y299W, N260D, K259N, Y299F, V366I, S365M, S339A, N174*, K37L, S40T, T182G, A265G, W482Y, M116A, N174Q, I235L, A265G, K37H, Q311R, N175Q, W48F, M116V, M116F, W167Y+ L202M+H210N+S339A+V366I, W167Y+L202M+ H210N+Y299F+S339A, W167Y+L202M+H210N+S339A, W167Y+L202M+Y299F, W48F+W167Y, W167Y+Y299F, W167Y+L202M, D30N+N33D+K37V+L202M+K383R, D30N+N33D+K37V+W48F+K383R, A51T, S334T, T246M, T246L, T246I, A186G, A51Q+G109M+Y203G, V238A+S334T, A51T+L202M, L202M+T246L, A51T+ N174Q+L202M+T246I+S334T, A51T+N174Q+L202M+ Q311R+S334T, I235L+T246M+I250L, A186D+L202M, A186D+L202M+N270G+N402Y, A186D+L202M+S339A, A186D+F195N+L202M, K37H+A51T+L202M, K37V+ A51T+L202M, A51T+L202M+S365C, A51T+L202M+ S339A, A51T+L202M+Q311T, A51T+L202M+M261L, A51T+L202M+H210N, A51T+L202M+N270G, A51T+ F195N+L202M, A51T+L202M+Q319H, A51T+L202M+ Q319R, A51T+L202M+Q311H, A51T+L202M+R247K, A51T+L202M+Q311R, A51T+L202M+Y398W, A51T+ L202M+Y299W, A51T+K108R+L202M, A51T+L202M+ Y243F, A51T+L202M+V474C, A51T+L202M+G460E, N174Q+L202M+A265G+Q311R+S334T, A51T+L202M+ T246V+A265G+Q311R, K37H+L202M+T246V+S334T, L202M+T246V+S334T+E416L, L202M+T246V+S334T+ N402Y, L202M+T246V+S334T+V366I, L202M+T246V+ S334T+S365M, L202M+T246V+S334T+S3650, L202M+ T246V+M261L+S334T, D30N+L202M+H210N+T246V+ S334T, L202M+T246V+N270G+S334T, F195N+L202M+ T246V+S334T, L202M+T246V+Q319H+S334T, L202M+ T246V+Q319R+S334T, L202M+T246V+Q311H+S334T, L202M+T246V+Q311R+S334T, L202M+T246V+S334T+ Y398W, L202M+T246V+K320H+S334T, L202M+T246V+ Y299W+S334T, L202M+T246V+K320R+S334T, L202M+ Y243F+S334T, L202M+T246V+S334T+V4740, L202M+ T246V+S334T+G460E, L202M+I235M+T246V+S334T, K108R+L202M+T246V+S334T, A51T+A186D+L202M+ N270G+N402Y, A186D+L202M+N270G+S339A+N402Y, A51T+A186D+L202M+N270G, A51T+L202M+T246V+ N270G, K37H+A51T+L202M+N270G, A51T+L202M+ T246L+N270G, A51T+N174Q+L202M+N270G, A51T+ L202M+V238A+N270G, A51T+L202M+A265G, A51T+ L202M+M261L+N270G, A51T+L202M+F267Y, A51T+ L202M+I275L, A51T+L202M+N270G+S365M, A51T+ L202M+N270G+S365C, A51T+L202M+N270G+Q311T, A51T+L202M+N270G+E416L, A51T+L202M+N270G+ N402Y, A51T+L202M+N270G+S365C, A51T+L202M+ N270G+K383R, A51T+L202M+N270G+V474C, A51T+ L202M+N270G+G460E, A51T+Q86L+L202M+N270G, A51T+Q86I+L202M+N270G, A51T+A113E+L202M+ N270G, A51T+K93H+L202M+N270G, A51T+K108R+ L202M+N270G, A51T+L202M+K269N, A51T+L202M+ Y243F+N270G, A51T+L202M+R247K+N270G, A51T+ L202M+R218N+N270G, A51T+L202M+S255K+N270G, A51T+L202M+I257A+N270G, A51T+L202M+V214I+ R218N+N270G, A51T+L202M+N270G+Q311H, A51T+ L202M+N270G+K320H, A51T+L202M+N270G+Y299W, A51T+L202M+N270G+K320R, A51T+L202M+N270G+ K383Q, A51T+K142R+L202M+N270G, A51T+E130Q+ L202M+N270G, A51T+K118N+L202M+N270G, A51T+ E138Q+L202M+N270G, A51T+K118H+L202M+N270G, A51T+E121H+L202M+N270G, K37H+A51T+N174Q+ L202M+A265G+Q311R+S334T, A51T+N174Q+L202M+ T246I+Q311R+S334T, K37V+A51T+L202M+A265G+ F267Y+Q311R+S334T, A51T+N174Q+L202M+A265G+ F267Y+Q311R+S334T, L202M+T246I+A265G+F267Y+ Q311R+S334T, A51T+L202M+F267Y+Q311R+S334T+ S365L, A51T+L202M+S365C, A51T+K108R+L202M, L202M+V238A+S334T, W48F+V238A+S334T, M116F+ V238A+S334T, V238A+S334T+W482Y, Y243F+S334T, L202M+V238A+Y299F+S334T, L202M+T246V+N270G+ S334T, W48F+K118H+V238A+S334T, W48F+L202M+ V238A+S334T, A51T+A186N+L202M+N270G+S365C, W167Y+A186N+H210N+S339A+V366I, W48F+W167Y+ A186N+H210N+S339A, W167Y+A186N+H210N+ Y299F+S339A+V366I, L202M+T246V+N270G+S334T+ S365C, or A186N+L202M+T246V+N270G+S334T, and fragments thereof having alpha amylase activity, wherein numbering of amino acid positions is according to the amino acid sequence set forth in SEQ ID NO: 2.

In one particular subset of the polypeptides of the invention, the polypeptide is a variant of SEQ ID NO:1 comprising a mutation at one or more positions corresponding to positions 48, 118, 167, 186, 210, 235, 238, 243, 246, 250, 299, 334, 339, 366, and 482, wherein numbering is according to SEQ ID NO: 2. Thus, the polypeptide may consist of the amino acid sequence of SEQ ID NO:1 with one or more mutations selected from the group consisting of W48F, K118H, W167Y, H210N, I235L, V238A, Y243F, T246M, I250L, Y299F, S334T, S339A, V366I, and W482Y, or a fragment thereof having alpha amylase activity, wherein numbering of amino acid positions is according to the amino acid sequence set forth in SEQ ID NO: 2. For example, the polypeptide may comprise or consist of an amino acid sequence selected from the following:

(a) SEQ ID NO: 1 with mutations W167Y, H210N and S339A;
(b) SEQ ID NO: 1 with mutations W167Y, H210N, S339A and V366I;
(c) SEQ ID NO: 1 with mutations W167Y, H210N, Y299F, S339A and V366I;
(d) SEQ ID NO: 1 with mutations W48F and W167Y;
(e) SEQ ID NO: 1 with mutations W48F, W167Y, H210N and S339A;
(f) SEQ ID NO: 1 with mutations W48F, W167Y, H210N, Y299F, S339A and V366I;
(g) SEQ ID NO: 1 with mutations V238A, S334T, and W482Y;
(h) SEQ ID NO: 1 with mutations Y243F and S334T;
(i) SEQ ID NO: 1 with mutation W48F;
(j) SEQ ID NO: 1 with mutation K118H;
(k) SEQ ID NO: 1 with mutation W167Y;
(l) SEQ ID NO: 1 with mutations W48F, V238A, and S334T;
(m) SEQ ID NO: 1 with mutations I234L, T246M, and I250L;
(n) SEQ ID NO: 1 with mutation S339A; and
(o) SEQ ID NO: 1 with mutation S334T;
and fragments thereof having alpha amylase activity, wherein numbering of amino acid positions is according to the amino acid sequence set forth in SEQ ID NO: 2.

The polypeptides of the invention represent variants of the amino acid sequence of the parent alpha-amylase, SEQ ID NO:1, which exhibit enhanced wash performance (for example, at temperatures of 40° C. or more). It will be appreciated by persons skilled in the art that different examples of the polypeptides of the invention will possess a different degree of amino acid sequence identity with the sequence of SEQ ID NO:1. Thus, the polypeptide may comprise or consist of an amino acid sequence which shares at least 70% sequence identity with SEQ ID NO: 1, for example at least 75%, at least 80%, at least 85%, at least 90%, at least 95%, at least 96%, at least 97%, at least 98%, or at least 99% sequence identity to SEQ ID NO: 1. In one embodiment, the number of mutations within the polypeptide relative to the amino acid sequence of SEQ ID NO:1 is between 1 and 20, e.g., between 1 and 10 mutations or between 1 and 5 mutations, such as 1, 2, 3, 4, 5, 6, 7, 8, 9 or 10 mutations.

Examples of alpha-amylase polypeptides of the invention are shown in Table 1 (wherein the amino acid sequence of the polypeptide is indicated relative to the sequence of the parent alpha-amylase of SEQ ID NO:1).

TABLE 1

Amino acid sequence of polypeptide (wherein the mutation positions are relative to SEQ ID NO: 2)

SEQ ID NO: 1 + K37H + L202M
SEQ ID NO: 1 + E360F + S365C
SEQ ID NO: 1 + M261L
SEQ ID NO: 1 + H210N
SEQ ID NO: 1 + Y243F
SEQ ID NO: 1 + K108R
SEQ ID NO: 1 + V474C
SEQ ID NO: 1 + G460E
SEQ ID NO: 1 + T81S
SEQ ID NO: 1 + K269S + N270G + A274K
SEQ ID NO: 1 + K37V + L202M
SEQ ID NO: 1 + L202M + Q311R
SEQ ID NO: 1 + N174Q + L202M
SEQ ID NO: 1 + K385H
SEQ ID NO: 1 + K385Q
SEQ ID NO: 1 + K385R
SEQ ID NO: 1 + K383Q

TABLE 1-continued

Amino acid sequence of polypeptide (wherein the mutation positions are relative to SEQ ID NO: 2)

SEQ ID NO: 1 + K320H
SEQ ID NO: 1 + K320R
SEQ ID NO: 1 + E276Q
SEQ ID NO: 1 + K93R
SEQ ID NO: 1 + K93H
SEQ ID NO: 1 + Q98R
SEQ ID NO: 1 + K118Q
SEQ ID NO: 1 + K118H
SEQ ID NO: 1 + K118N
SEQ ID NO: 1 + E130H
SEQ ID NO: 1 + E130Q
SEQ ID NO: 1 + E138Q
SEQ ID NO: 1 + K142R
SEQ ID NO: 1 + K142Q
SEQ ID NO: 1 + E416L
SEQ ID NO: 1 + Q394K
SEQ ID NO: 1 + S384E
SEQ ID NO: 1 + Y64W
SEQ ID NO: 1 + K37R
SEQ ID NO: 1 + D30N
SEQ ID NO: 1 + F295Y
SEQ ID NO: 1 + Y243M
SEQ ID NO: 1 + Y178W
SEQ ID NO: 1 + K281H
SEQ ID NO: 1 + K269N
SEQ ID NO: 1 + Y198F
SEQ ID NO: 1 + Q311T
SEQ ID NO: 1 + F195N
SEQ ID NO: 1 + I257A
SEQ ID NO: 1 + S255K
SEQ ID NO: 1 + R247K
SEQ ID NO: 1 + Y404W
SEQ ID NO: 1 + Y398W
SEQ ID NO: 1 + Q319H
SEQ ID NO: 1 + Q319R
SEQ ID NO: 1 + Q311H
SEQ ID NO: 1 + Q311R
SEQ ID NO: 1 + Y299W
SEQ ID NO: 1 + N260D
SEQ ID NO: 1 + K259N
SEQ ID NO: 1 + Y299F
SEQ ID NO: 1 + A434D
SEQ ID NO: 1 + V366I
SEQ ID NO: 1 + S365M
SEQ ID NO: 1 + S339A
SEQ ID NO: 1 + N174*
SEQ ID NO: 1 + I235V
SEQ ID NO: 1 + I250L
SEQ ID NO: 1 + I250V
SEQ ID NO: 1 + K37V
SEQ ID NO: 1 + K37M
SEQ ID NO: 1 + K37L
SEQ ID NO: 1 + Y203H
SEQ ID NO: 1 + S40T
SEQ ID NO: 1 + W187Y
SEQ ID NO: 1 + V238T
SEQ ID NO: 1 + M105Y
SEQ ID NO: 1 + M105F
SEQ ID NO: 1 + M105I
SEQ ID NO: 1 + I206L
SEQ ID NO: 1 + T182G
SEQ ID NO: 1 + M116I
SEQ ID NO: 1 + Y135H
SEQ ID NO: 1 + Y203N
SEQ ID NO: 1 + Y203G
SEQ ID NO: 1 + N25K
SEQ ID NO: 1 + M116L
SEQ ID NO: 1 + A265G
SEQ ID NO: 1 + K242P
SEQ ID NO: 1 + V214R
SEQ ID NO: 1 + M208F
SEQ ID NO: 1 + Y198F
SEQ ID NO: 1 + W482Y
SEQ ID NO: 1 + V214T
SEQ ID NO: 1 + V214I
SEQ ID NO: 1 + M261A
SEQ ID NO: 1 + M105F

TABLE 1-continued

Amino acid sequence of polypeptide (wherein the mutation positions are relative to SEQ ID NO: 2)

SEQ ID NO: 1 + M208L
SEQ ID NO: 1 + M116A
SEQ ID NO: 1 + N174Q
SEQ ID NO: 1 + N174* + N175Q
SEQ ID NO: 1 + I235L
SEQ ID NO: 1 + M105L
SEQ ID NO: 1 + K37H
SEQ ID NO: 1 + W469F
SEQ ID NO: 1 + Y203F
SEQ ID NO: 1 + G109A
SEQ ID NO: 1 + N175Q
SEQ ID NO: 1 + W48F
SEQ ID NO: 1 + M116V
SEQ ID NO: 1 + M116F
SEQ ID NO: 1 + F295W
SEQ ID NO: 1 + Y298W
SEQ ID NO: 1 + M208V
SEQ ID NO: 1 + M208F
SEQ ID NO: 1 + M10L + M261L
SEQ ID NO: 1 + W187Y + M208L
SEQ ID NO: 1 + Y298F
SEQ ID NO: 1 + W167Y
SEQ ID NO: 1 + W167H
SEQ ID NO: 1 + W189H
SEQ ID NO: 1 + F295Y
SEQ ID NO: 1 + I235M
SEQ ID NO: 1 + Y243F + F267Y
SEQ ID NO: 1 + K37V + P45R + K383R
SEQ ID NO: 1 + D30N + N33D + K37V + K383R
SEQ ID NO: 1 + W167Y + H210N + S339A + V366I
SEQ ID NO: 1 + S339A + V366I
SEQ ID NO: 1 + W167Y + H210N + S339A
SEQ ID NO: 1 + H210N + S339A
SEQ ID NO: 1 + W167Y + H210N
SEQ ID NO: 1 + W167Y + L202M + H210N + Y299F + S339A + V366I
SEQ ID NO: 1 + W167Y + H210N + Y243F + S339A + V366I
SEQ ID NO: 1 + W167Y + H210N + S339A + V366I + W482Y
SEQ ID NO: 1 + M116F + W167Y + H210N + S339A + V366I
SEQ ID NO: 1 + W48F + W167Y + H210N + S339A + V366I
SEQ ID NO: 1 + W167Y + H210N + Y299F + S339A + V366I
SEQ ID NO: 1 + W167Y + L202M + H210N + S339A + V366I
SEQ ID NO: 1 + W167Y + L202M + H210N + Y299F + S339A
SEQ ID NO: 1 + W167Y + H210N + S339A + W482Y
SEQ ID NO: 1 + M116F + W167Y + H210N + S339A
SEQ ID NO: 1 + W48F + W167Y + H210N + S339A
SEQ ID NO: 1 + W167Y + H210N + Y299F + S339A
SEQ ID NO: 1 + W167Y + L202M + H210N + S339A
SEQ ID NO: 1 + W167Y + L202M + Y299F
SEQ ID NO: 1 + W167Y + Y243F
SEQ ID NO: 1 + M116F + W167Y
SEQ ID NO: 1 + W48F + W167Y
SEQ ID NO: 1 + W167Y + Y299F
SEQ ID NO: 1 + W167Y + L202M
SEQ ID NO: 1 + W167Y + H210N + V366I
SEQ ID NO: 1 + W167Y + V366I
SEQ ID NO: 1 + H210N + V366I
SEQ ID NO: 1 + W167Y + S339A + V366I
SEQ ID NO: 1 + D30N + N33D + K37V + L202M + K383R
SEQ ID NO: 1 + D30N + N33D + K37V + W48F + K383R
SEQ ID NO: 1 + D30N + N33D + K37V + M116F + K383R
SEQ ID NO: 1 + D30N + N33D + K37V + K383R + W482Y
SEQ ID NO: 1 + A51T
SEQ ID NO: 1 + A51T + N54S
SEQ ID NO: 1 + S334T
SEQ ID NO: 1 + T246M
SEQ ID NO: 1 + T246L
SEQ ID NO: 1 + T246V
SEQ ID NO: 1 + T246I
SEQ ID NO: 1 + A186G
SEQ ID NO: 1 + A51Q + G109M + Y203G
SEQ ID NO: 1 + V238A + S334T
SEQ ID NO: 1 + L202M + T246V
SEQ ID NO: 1 + A51T + L202M
SEQ ID NO: 1 + L202M + T246L
SEQ ID NO: 1 + L202M + T246I + S334T
SEQ ID NO: 1 + L202M + T246V + S334T
SEQ ID NO: 1 + L202M + T246L + S334T

TABLE 1-continued

Amino acid sequence of polypeptide (wherein the mutation positions are relative to SEQ ID NO: 2)

SEQ ID NO: 1 + A51T + L202M + T246I + S334T
SEQ ID NO: 1 + A51T + N174Q + L202M + T246I + S334T
SEQ ID NO: 1 + L202M + T246L + S334T
SEQ ID NO: 1 + A51T + N174Q + L202M + Q311R + S334T
SEQ ID NO: 1 + I235L + T246M + I250L
SEQ ID NO: 1 + A186D + L202M
SEQ ID NO: 1 + A186D + L202M + N270G + N402Y
SEQ ID NO: 1 + A186D + L202M + S339A
SEQ ID NO: 1 + A186D + F195N + L202M
SEQ ID NO: 1 + K37H + A51T + L202M
SEQ ID NO: 1 + K37V + A51T + L202M
SEQ ID NO: 1 + A51T + L202M + S365C
SEQ ID NO: 1 + A51T + L202M + S339A
SEQ ID NO: 1 + A51T + L202M + Q311T
SEQ ID NO: 1 + A51T + L202M + M261L
SEQ ID NO: 1 + A51T + L202M + H210N
SEQ ID NO: 1 + A51T + L202M + N270G
SEQ ID NO: 1 + A51T + F195N + L202M
SEQ ID NO: 1 + A51T + L202M + Q319H
SEQ ID NO: 1 + A51T + L202M + Q319R
SEQ ID NO: 1 + A51T + L202M + Q311H
SEQ ID NO: 1 + A51T + L202M + R247K
SEQ ID NO: 1 + A51T + L202M + Q311R
SEQ ID NO: 1 + A51T + L202M + Y398W
SEQ ID NO: 1 + A51T + L202M + Y299W
SEQ ID NO: 1 + A51T + K108R + L202M
SEQ ID NO: 1 + A51T + L202M + Y243F
SEQ ID NO: 1 + A51T + L202M + V474C
SEQ ID NO: 1 + A51T + L202M + G460E
SEQ ID NO: 1 + N174Q + L202M + A265G + Q311R + S334T
SEQ ID NO: 1 + A51T + L202M + T246V + A265G + Q311R
SEQ ID NO: 1 + A51T + L202M + A265G + Q311R
SEQ ID NO: 1 + K37H + L202M + T246V + S334T
SEQ ID NO: 1 + L202M + T246V + S334T + E416L
SEQ ID NO: 1 + L202M + T246V + S334T + N402Y
SEQ ID NO: 1 + L202M + T246V + S334T + V366I
SEQ ID NO: 1 + L202M + T246V + S334T + S365M
SEQ ID NO: 1 + L202M + T246V + S334T + S365C
SEQ ID NO: 1 + L202M + T246V + M261L + S334T
SEQ ID NO: 1 + D30N + L202M + H210N + T246V + S334T
SEQ ID NO: 1 + L202M + T246V + N270G + S334T
SEQ ID NO: 1 + F195N + L202M + T246V + S334T
SEQ ID NO: 1 + L202M + T246V + Q319H + S334T
SEQ ID NO: 1 + L202M + T246V + Q319R + S334T
SEQ ID NO: 1 + L202M + T246V + Q311H + S334T
SEQ ID NO: 1 + L202M + T246V + Q311R + S334T
SEQ ID NO: 1 + L202M + T246V + S334T + Y398W
SEQ ID NO: 1 + L202M + T246V + K320N + S334T
SEQ ID NO: 1 + L202M + T246V + Y299W + S334T
SEQ ID NO: 1 + L202M + T246V + K320R + S334T
SEQ ID NO: 1 + L202M + T246V + Y243F + S334T
SEQ ID NO: 1 + L202M + T246V + S334T + V474C
SEQ ID NO: 1 + L202M + T246V + S334T + G460E
SEQ ID NO: 1 + L202M + I235M + T246V + S334T
SEQ ID NO: 1 + K108R + L202M + T246V + S334T
SEQ ID NO: 1 + A51T + A186D + L202M + N270G + N402Y
SEQ ID NO: 1 + A186D + L202M + N270G + S339A + N402Y
SEQ ID NO: 1 + A51T + A186D + L202M + N270G
SEQ ID NO: 1 + A51T + L202M + T246V + N270G
SEQ ID NO: 1 + K37H + A51T + L202M + N270G
SEQ ID NO: 1 + A51T + L202M + T246L + N270G
SEQ ID NO: 1 + A51T + N174Q + L202M + N270G
SEQ ID NO: 1 + A51T + L202M + V238A + N270G
SEQ ID NO: 1 + A51T + L202M + A265G
SEQ ID NO: 1 + A51T + L202M + M261L + N270G
SEQ ID NO: 1 + A51T + L202M + F267Y
SEQ ID NO: 1 + A51T + L202M + I275L
SEQ ID NO: 1 + A51T + L202M + N270G + S365M
SEQ ID NO: 1 + A51T + L202M + N270G + S365C
SEQ ID NO: 1 + A51T + L202M + N270G + Q311T
SEQ ID NO: 1 + A51T + L202M + N270G + E416L
SEQ ID NO: 1 + A51T + L202M + N270G + N402Y
SEQ ID NO: 1 + A51T + L202M + N270G + S365C
SEQ ID NO: 1 + A51T + L202M + N270G + K383R
SEQ ID NO: 1 + A51T + L202M + N270G + V474C
SEQ ID NO: 1 + A51T + L202M + N270G + G460E
SEQ ID NO: 1 + A51T + Q86L + L202M + N270G

TABLE 1-continued

Amino acid sequence of polypeptide (wherein the mutation positions are relative to SEQ ID NO: 2)

SEQ ID NO: 1 + A51T + Q86I + L202M + N270G
SEQ ID NO: 1 + A51T + A113E + L202M + N270G
SEQ ID NO: 1 + A51T + K93H + L202M + N270G
SEQ ID NO: 1 + A51T + K108R + L202M + N270G
SEQ ID NO: 1 + A51T + L202M + K269N
SEQ ID NO: 1 + A51T + L202M + Y243F + N270G
SEQ ID NO: 1 + A51T + F195N + L202M + N270G
SEQ ID NO: 1 + A51T + L202M + R247K + N270G
SEQ ID NO: 1 + A51T + L202M + R218N + N270G
SEQ ID NO: 1 + A51T + L202M + S255K + N270G
SEQ ID NO: 1 + A51T + L202M + I257A + N270G
SEQ ID NO: 1 + A51T + L202M + V214I + R218N + N270G
SEQ ID NO: 1 + A51T + L202M + N270G + Q311H
SEQ ID NO: 1 + A51T + L202M + N270G + K320H
SEQ ID NO: 1 + A51T + L202M + N270G + Y299W
SEQ ID NO: 1 + A51T + L202M + N270G + K320R
SEQ ID NO: 1 + A51T + L202M + N270G + K383Q
SEQ ID NO: 1 + A51T + K142R + L202M + N270G
SEQ ID NO: 1 + A51T + E130Q + L202M + N270G
SEQ ID NO: 1 + A51T + K118N + L202M + N270G
SEQ ID NO: 1 + A51T + E138Q + L202M + N270G
SEQ ID NO: 1 + A51T + K118H + L202M + N270G
SEQ ID NO: 1 + A51T + K118Q + L202M + N270G
SEQ ID NO: 1 + A51T + Q86H + L202M + N270G
SEQ ID NO: 1 + A51T + E121H + L202M + N270G
SEQ ID NO: 1 + A51T + K118R + L202M + N270G
SEQ ID NO: 1 + K37H + A51T + N174Q + L202M + A265G + Q311R + S334T
SEQ ID NO: 1 + A51T + N174Q + L202M + T246I + Q311R + S334T
SEQ ID NO: 1 + K37V + A51T + L202M + A265G + F267Y + Q311R + S334T
SEQ ID NO: 1 + A51T + N174Q + L202M + A265G + F267Y + Q311R + S334T
SEQ ID NO: 1 + A51G + L202M + Q311R + S334T
SEQ ID NO: 1 + L202M + T246I + A265G + F267Y + Q311R + S334T
SEQ ID NO: 1 + A51T + L202M + F267Y + Q311R + S334T + S365L
SEQ ID NO: 1 + A51T + L202M + S365C
SEQ ID NO: 1 + A51T + K108R + L202M
SEQ ID NO: 1 + A51T + S365C
SEQ ID NO: 1 + A51T + K108R
SEQ ID NO: 1 + L202M + V238A + S334T
SEQ ID NO: 1 + W48F + V238A + S334T
SEQ ID NO: 1 + M116F + V238A + S334T
SEQ ID NO: 1 + V238A + S334T + W482Y
SEQ ID NO: 1 + Y243F + S334T
SEQ ID NO: 1 + L202M + V238A + Y299F + S334T
SEQ ID NO: 1 + L202M + T246V + N270G + S334T
SEQ ID NO: 1 + W48F + K118H + V238A + S334T
SEQ ID NO: 1 + W48F + L202M + V238A + S334T
SEQ ID NO: 1 + A51T + A186N + L202M + N270G + S365C
SEQ ID NO: 1 + W167Y + A186N + H210N + S339A + V366I
SEQ ID NO: 1 + W48F + W167Y + A186N + H210N + S339A
SEQ ID NO: 1 + W167Y + A186N + H210N + Y299F + S339A + V366I
SEQ ID NO: 1 + L202M + T246V + N270G + S334T + S365C
SEQ ID NO: 1 + A186N + L202M + T246V + N270G + S334T

In a particular embodiment, the variant alpha-amylase of the invention have an enhanced wash performance at a temperature of both 40° C. and 50° C. Such variant alpha-amylases may be selected from (a) SEQ ID NO: 1 with mutations V238A, S334T, and W482Y;
(b) SEQ ID NO: 1 with mutations Y243F and S334T;
(c) SEQ ID NO: 1 with mutations W48F, W167Y, H210N, Y299F, S339A, and V366I;
(d) SEQ ID NO: 1 with mutations W48F, W167F, H210N, and S339A;
(e) SEQ ID NO: 1 with mutation W48F; and
(f) SEQ ID NO: 1 with mutations W167Y, H210N, and S339A, and fragments thereof having alpha amylase activity, wherein numbering of amino acid positions is according to the amino acid sequence set forth in SEQ ID NO: 2.

Preparation of Polypeptides of the Invention

The variant alpha-amylases of the invention can be prepared using any mutagenesis procedure known in the art, such as site-directed mutagenesis, synthetic gene construction, semi-synthetic gene construction, random mutagenesis, shuffling, etc.

Site-directed mutagenesis is a technique in which one or more (e.g., several) mutations are introduced at one or more defined sites in a polynucleotide encoding the parent.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests the plasmid and the oligonucleotide is the same, permitting sticky ends of the plasmid and the insert to ligate to one another. See, e.g., Scherer and Davis, 1979, Proc. Natl. Acad. Sci. USA 76: 4949-4955; and Barton et al., 1990, Nucleic Acids Res. 18: 7349-4966.

Site-directed mutagenesis can also be accomplished in vivo by methods known in the art. See, e.g., U.S. Patent Application Publication No. 2004/0171154; Storici et al., 2001, Nature Biotechnol. 19: 773-776; Kren et al., 1998, Nat. Med. 4: 285-290; and Calissano and Macino, 1996, Fungal Genet. Newslett. 43: 15-16.

Any site-directed mutagenesis procedure can be used in the present invention. There are many commercial kits available that can be used to prepare variants.

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, Nature 432: 1050-1054) and similar technologies wherein oligonucleotides are synthesized and assembled upon photo-programmable microfluidic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, Science 241: 53-57; Bowie and Sauer, 1989, Proc. Natl. Acad. Sci. USA 86: 2152-2156; WO 95/17413; or WO 95/22625. Other methods that can be used include error-prone PCR, phage display (e.g., Lowman et al., 1991, Biochemistry 30: 10832-10837; U.S. Pat. No. 5,223,409; WO 92/06204) and region-directed mutagenesis (Derbyshire et al., 1986, Gene 46: 145; Ner et al., 1988, DNA 7: 127).

Mutagenesis/shuffling methods can be combined with high-throughput, automated screening methods to detect activity of cloned, mutagenized polypeptides expressed by host cells (Ness et al., 1999, Nature Biotechnology 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled.

Polynucleotides

The present invention also relates to polynucleotides encoding a variant of the present invention. Accordingly, the present invention relates to polynucleotides encoding a variant polypeptide having alpha-amylase activity and exhibits an enhanced wash performance compared to the polypeptide of SEQ ID NO: 1. In particular, the invention relates to polynucleotides encoding a variant polypeptide comprising a mutation at one or more positions corresponding to positions 10, 25, 30, 37, 40, 48, 51, 54, 64, 81, 86, 93, 98, 105, 108, 109, 113, 116, 118, 121, 130, 135, 138, 142, 167, 174, 175, 178, 182, 186, 187, 189, 195, 198, 202, 203, 206, 208, 210, 214, 218, 235, 238, 242, 243, 246, 247, 250, 255, 257, 259, 260, 261, 265, 267, 269, 270, 274, 275, 276, 281, 295, 298, 299, 311, 319, 320, 334, 339, 360, 365, 366, 383, 384, 385, 394, 398, 402, 404, 416, 434, 460, 469, 474, and 482, wherein numbering is according to the amino acid sequence set forth in SEQ ID NO: 2.

Nucleic Acid Constructs

The present invention also relates to nucleic acid constructs comprising a polynucleotide encoding a variant polypeptide of the invention operably linked to one or more control sequences that direct the expression of the coding sequence in a suitable host cell under conditions compatible with the control sequences. Accordingly, the present invention relates to nucleic acid constructs comprising a polynucleotide encoding a variant polypeptide having alpha-amylase activity and exhibits an enhanced wash performance compared to the polypeptide of SEQ ID NO: 1, operably linked to one or more control sequences that direct the expression of the coding sequence in a suitable host cell under conditions compatible with the control sequences. In particular, the invention relates to nucleic acid constructs encoding a variant polypeptide comprising a mutation at one or more positions corresponding to positions 10, 25, 30, 37, 40, 48, 51, 54, 64, 81, 86, 93, 98, 105, 108, 109, 113, 116, 118, 121, 130, 135, 138, 142, 167, 174, 175, 178, 182, 186, 187, 189, 195, 198, 202, 203, 206, 208, 210, 214, 218, 235, 238, 242, 243, 246, 247, 250, 255, 257, 259, 260, 261, 265, 267, 269, 270, 274, 275, 276, 281, 295, 298, 299, 311, 319, 320, 334, 339, 360, 365, 366, 383, 384, 385, 394, 398, 402, 404, 416, 434, 460, 469, 474, and 482, wherein numbering is according to the amino acid sequence set forth in SEQ ID NO: 2, operably linked to one or more control sequences that direct the expression of the coding sequence in a suitable host cell under conditions compatible with the control sequences.

The polynucleotide may be manipulated in a variety of ways to provide for expression of a variant. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide which is recognized by a host cell for expression of the polynucleotide. The promoter contains transcriptional control sequences that mediate the expression of the variant. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator sequence is operably linked to the 3'-terminus of the polynucleotide encoding the variant. Any terminator that is functional in the host cell may be used.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, Journal of Bacteriology 177: 3465-3471).

The control sequence may also be a leader, a nontranslated region of an mRNA that is important for translation by the host cell. The leader sequence is operably linked to the 5'-terminus of the polynucleotide encoding the variant. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the variant-encoding sequence and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a variant and directs the variant into the cell's secretory pathway. The 5'-end of the coding sequence of the polynucleotide may inherently contain a signal peptide coding sequence naturally linked in translation reading frame with the segment of the coding sequence that encodes the variant. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the variant. However, any signal peptide coding sequence that directs the expressed variant into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, Microbiological Reviews 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a variant. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of the variant and the signal peptide sequence is positioned next to the N-terminus of the propeptide sequence.

It may also be desirable to add regulatory sequences that regulate expression of the variant relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the variant would be operably linked with the regulatory sequence.

Expression Vectors

The present invention also relates to recombinant expression vectors comprising a polynucleotide encoding a variant polypeptide of the present invention, a promoter, and transcriptional and translational stop signals. Accordingly, the present invention relates to recombinant expression vectors comprising a polynucleotide encoding a variant polypeptide having alpha-amylase activity and exhibits an enhanced wash performance compared to the polypeptide of SEQ ID NO: 1, a promoter, and transcriptional and translational stop signals. In particular, the present invention relates to recombinant expression vector comprising a polynucleotide encoding a variant polypeptide comprising a mutation at one or more positions corresponding to positions 10, 25, 30, 37, 40, 48, 51, 54, 64, 81, 86, 93, 98, 105, 108, 109, 113, 116, 118, 121, 130, 135, 138, 142, 167, 174, 175, 178, 182, 186, 187, 189, 195, 198, 202, 203, 206, 208, 210, 214, 218, 235, 238, 242, 243, 246, 247, 250, 255, 257, 259, 260, 261, 265, 267, 269, 270, 274, 275, 276, 281, 295, 298, 299, 311, 319, 320, 334, 339, 360, 365, 366, 383, 384, 385, 394, 398, 402, 404, 416, 434, 460, 469, 474, and 482, wherein numbering is according to the amino acid sequence set forth in SEQ ID NO: 2, a promoter, and transcriptional and translational stop codons.

The various nucleotide and control sequences may be joined together to produce a recombinant expression vector that may include one or more convenient restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene.

The vector preferably contains an element(s) that permits integration of the vector into the host cell's genome or autonomous replication of the vector in the cell independent of the genome. For integration into the host cell genome, the vector may rely on the polynucleotide's sequence encoding the variant or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMß1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a variant. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide encoding a variant polypeptide of the present invention operably linked to one or more control sequences that direct the production of the variant polypeptide of the present invention. Accordingly, the present invention relates to recombinant host cells, comprising a polynucleotide encoding a variant polypeptide having alpha-amylase activity and exhibits an enhanced wash performance compared to the polypeptide of SEQ ID NO: 1, operably linked to one or more control sequences that direct the production of the variant polypeptide. In particular, the present invention relates to recombinant host cells, comprising a polynucleotide encoding a variant polypeptide comprising a mutation at one or more positions corresponding to positions 10, 25, 30, 37, 40, 48, 51, 54, 64, 81, 86, 93, 98, 105, 108, 109, 113, 116, 118, 121, 130, 135, 138, 142, 167, 174, 175, 178, 182, 186, 187, 189, 195, 198, 202, 203, 206, 208, 210, 214, 218, 235, 238, 242, 243, 246, 247, 250, 255, 257, 259, 260, 261, 265, 267, 269, 270, 274, 275, 276, 281, 295, 298, 299, 311, 319, 320, 334, 339, 360, 365, 366, 383, 384, 385, 394, 398, 402, 404, 416, 434, 460, 469, 474, and 482, wherein numbering is according to the amino acid sequence set forth in SEQ ID NO: 2, operably linked to one or more control sequences that direct the production of the variant polypeptide.

A construct or vector comprising a polynucleotide is introduced into a host cell so that the construct or vector is maintained as a chromosomal integrant or as a self-replicating extrachromosomal vector as described earlier. The term "host cell" encompasses any progeny of a parent cell that is not identical to the parent cell due to mutations that occur during replication. The choice of a host cell will to a large extent depend upon the gene encoding the variant and its source.

The host cell may be any cell useful in the recombinant production of a variant, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausfi, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell, including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (Praha) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397), or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804) or conjugation (see, e.g., Clewell, 1981, *Microbiol. Rev.* 45: 409-436). However, any method known in the art for introducing DNA into a host cell can be used.

The host cell may also be a eukaryote, such as a plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, *Soc. App. Bacteriol. Symposium Series* No. 9, 1980).

The yeast host cell may be a *Candida, Hansenula, Kluyveromyces, Pichia, Saccharomyces, Schizosaccharomyces*, or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus*

*fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a variant alpha-amylase, comprising: (a) cultivating a host cell of the present invention under conditions suitable for expression of the variant polypeptide; and (b) recovering the variant polypeptide.

The host cells are cultivated in a nutrient medium suitable for production of the variant using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the variant to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the variant is secreted into the nutrient medium, the variant can be recovered directly from the medium. If the variant is not secreted, it can be recovered from cell lysates.

The variant may be detected using methods known in the art. Suitable detection methods include, but are not limited to, use of specific antibodies, formation of an enzyme product, or disappearance of an enzyme substrate. For example, an enzyme assay may be used to determine the alpha-amylase activity of the variant (see Examples).

The variant may be recovered using methods known in the art. For example, the variant may be recovered from the nutrient medium by conventional procedures including, but not limited to, collection, centrifugation, filtration, extraction, spray-drying, evaporation, or precipitation.

The variant may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure variants.

In an alternative aspect, the variant is not recovered, but rather a host cell of the present invention expressing the variant is used as a source of the variant.

Compositions

The alpha-amylase polypeptides of the invention may be added to and thus become a component of a detergent composition. Accordingly, the present invention relates to compositions comprising a variant polypeptide having alpha-amylase activity and exhibits an enhanced wash performance compared to the polypeptide of SEQ ID NO: 1. In particular, the present invention relates to compositions comprising a variant polypeptide comprising a mutation at one or more positions corresponding to positions 10, 25, 30, 37, 40, 48, 51, 54, 64, 81, 86, 93, 98, 105, 108, 109, 113, 116, 118, 121, 130, 135, 138, 142, 167, 174, 175, 178, 182, 186, 187, 189, 195, 198, 202, 203, 206, 208, 210, 214, 218, 235, 238, 242, 243, 246, 247, 250, 255, 257, 259, 260, 261, 265, 267, 269, 270, 274, 275, 276, 281, 295, 298, 299, 311, 319, 320, 334, 339, 360, 365, 366, 383, 384, 385, 394, 398, 402, 404, 416, 434, 460, 469, 474, and 482, wherein numbering is according to the amino acid sequence set forth in SEQ ID NO: 2.

Thus, a further aspect of the invention provides a detergent composition comprising a polypeptide of the invention and a surfactant (such as an anionic surfactant, a cationic surfactant, a nonionic surfactant and/or an amphoteric surfactant). Also provided is a concentrate or additive for making such detergent compositions, which concentrate or additive comprises a polypeptide of the invention and, optionally, a surfactant.

As discussed in detail below, the detergent composition may further comprise one or more additional components selected from the group consisting of oxidizing agents, bleach activators, bulking agents, builders, buffering agents, structurants, sequestrants, optical brighteners, antifoaming agents, enzymes, fragrances, anti-redeposition agents, skin conditioning agents, softness extenders, emulsifiers, and colorants.

In one embodiment, the composition is a liquid or powder laundry detergent composition.

In a further embodiment, the composition is a liquid or powder automatic dishwashing (ADW) detergent composition.

The detergent composition of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the invention provides a detergent concentrate/additive comprising the alpha-amylase polypeptide of the invention. The detergent concentrate/additive, as well as the detergent composition, may comprise one or more other enzymes such as a protease, a lipase, a peroxidase, another amylolytic enzyme, e.g., another alpha-amylase, glucoamylase, maltogenic amylase, CGTase and/or a cellulase, mannanase (such as MANNAWAY™ from Novozymes, Denmark)), pectinase, pectine lyase, cutinase, and/or laccase.

In general the properties of the chosen enzyme(s) should be compatible with the selected detergent, (i.e., pH-optimum, compatibility with other enzymatic and non-enzymatic ingredients, etc.), and the enzyme(s) should be present in effective amounts.

Proteases: Suitable proteases include those of animal, vegetable or microbial origin. Microbial origin is preferred. Chemically modified or protein engineered mutants are included. The protease may be a serine protease or a metallo protease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like pro-teases are trypsin (e.g., of porcine or bovine origin) and the *Fusarium* protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235 and 274. Preferred commercially available protease enzymes include ALCALASE®, SAVINASE® (SEQ ID NO: 3), PRIMASE®, DURALASE®, ESPERASE®, and KANNASE® (from Novozymes NS), MAXATASE®, MAXACAL, MAXAPEM®, PROPERASE®, PURAFECT®, PURAFECT OXP®, FN2®, FN3®, FN4® (Genencor International Inc.).

Lipases: Suitable lipases include those of bacterial or fungal origin. Chemically modified or protein engineered mutants are included. Examples of useful lipases include lipases from *Humicola* (synonym *Thermomyces*), e.g., from *H. lanuginosa* (*T. lanuginosus*) as described in EP 258 068 and EP 305 216 or from *H. insolens* as described in WO 96/13580, a *Pseudomonas* lipase, e.g., from *P. alcaligenes* or *P. pseudoalcaligenes* (EP 218 272), *P. cepacia* (EP 331 376), *P. stutzeri* (GB 1,372,034), *P. fluorescens*, *Pseudomonas* sp. strain SD 705 (WO 95/06720 and WO 96/27002), *P. wisconsinensis* (WO 96/12012), a *Bacillus* lipase, e.g., from *B. subtilis* (Dartois et al. (1993), Biochemica et Biophysica Acta, 1131:253-360), *B. stearothermophilus* (JP 64/744992) or *B. pumilus* (WO 91/16422). Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipase enzymes include LIPOLASE<™> and LIPOLASE ULTRA<™> (Novozymes NS, SEQ ID NO: 4 herein).

Amylases: Suitable amylases (alpha and/or beta) include those of bacterial or fungal origin. Chemically modified or protein engineered mutants are included. Amylases include, for example, alpha-amylases obtained from *Bacillus*, e.g., a special strain of *B. licheniformis*, described in more detail in GB 1,296,839. Examples of useful alpha-amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444. Commercially available alpha-amylases are DURAMYL<™>, LIQUEZYME™, TERMAMYL<™>, NATALASE<™>, FUNGAMYL<™> and BAN<™> (Novozymes NS), Preferenz S100, Preferenz S110, Preferenz S1000, Excellenz S110, Excellenz S1000, Excellenz S2000, RAPIDASE<™> and PURASTAR<™> (from Genencor International Inc.). Thus, suitable amylases may be any one of those listed herein as SEQ ID NOs: 5, 6, 7, 8, 9, 10, and 11, and a variant thereof.

Cellulases: Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259. Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and PCT/DK98/00299.

Commercially available cellulases include CELLUZYME®, and CAREZYME® (Novozymes A/S), CLAZINASE®, and PURADAX HA® (Genencor International Inc.), and KAC-500(B)® (Kao Corporation).

Peroxidases/Oxidases: Suitable peroxidases/oxidases include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257. Commercially available peroxidases include GUARDZYME® (Novozymes NS).

Lechinases: Suitable Lechinases include those of bacterial or fungal orign. They may be chemically modified or protein engineered. Examples of useful lechinases include those presented in SEQ ID NO: 3, 4, and 5 (Novozymes NS) and WO 99/06516 (Henkel KGAA). Examples of other suitable lichinases, which may be chemically modified or protein engineered, are those shown as SEQ ID NOs: 12, 13, 14, and 15 herein.

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, e.g., granulate, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonyl-phenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238 216.

The detergent composition of the invention may be in any convenient form, e.g., a bar, a tablet, a powder, a granule, a paste or a liquid. A liquid detergent may be aqueous, typically containing up to 70% water and 0-30% organic solvent, or non-aqueous.

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually comprise from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually comprise from about 0.2% to about 40% of a non-ionic surfactant such as alcohol ethoxylate, nonyl-phenol ethoxylate, alkylpolyglycoside, alkyldimethylamine-oxide, ethoxylated fatty acid monoethanol-amide, fatty acid mono-ethanolamide, polyhydroxy alkyl fatty acid amide, or N-acyl N-alkyl derivatives of glucosamine ("glucamides").

The detergent may comprise 0-65% of a detergent builder or complexing agent such as zeolite, diphosphate, triphosphate, phosphonate, carbonate, citrate, nitrilotriacetic acid, ethylenediaminetetraacetic acid, diethylenetri-aminepentaacetic acid, alkyl- or alkenylsuccinic acid, soluble silicates or layered silicates (e.g. SKS-6 from Hoechst). Other complexing agents may be methylglycinediacetic acid (MGDA) and glutamic acid diacetic acid (GLDA) which may be in particular used in phosphate-free automatic dishwash detergents.

The detergent may comprise one or more polymers. Examples are sulfonated polymers, carboxymethylcellulose, poly(vinyl-pyrrolidone), poly (ethylene glycol), poly(vinyl alcohol), poly(vinylpyridine-N-oxide), poly(vinylimidazole), polycarboxylates such as polyacrylates, maleic/acrylic acid copolymers and lauryl methacrylate/acrylic acid copolymers.

The detergent may contain a bleaching system, which may comprise a $H_2O_2$ source such as perborate or percarbonate which may be combined with a peracid-forming bleach activator such as tetraacetylethylenediamine or nonanoyloxyben-zenesul-fonate. Furthermore, the bleach catalyst may be Mn and/or Co based components. Alternatively, the bleaching system may comprise peroxyacids of, e.g., the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in, e.g., WO 92/19709 and WO 92/19708.

The detergent may also contain other conventional detergent ingredients such as e.g. fabric conditioners including clays, foam boosters, suds suppressors, anti-corrosion agents, soil-suspending agents, anti-soil re-deposition agents, dyes, bactericides, optical brighteners, hydrotropes, tarnish inhibitors, or perfumes.

It is at present contemplated that in the detergent compositions any enzyme, in particular the alpha amylase polypeptides of the invention, may be added in an amount corresponding to 0.01-100 mg of enzyme protein per liter of wash liquor, preferably 0.05-5 mg of enzyme protein per liter of wash liquor, in particular 0.1-1 mg of enzyme protein per liter of wash liquor.

The alpha amylase polypeptides of the invention may additionally be incorporated in the detergent formulations disclosed in WO 2006/002643, which is hereby incorporated as reference.

Examples of Dishwash Detergent Compositions of the Invention

The alpha-amylase polypeptide of the invention may also be used in dish wash detergent compositions, including the following:

| (a) POWDER AUTOMATIC DISHWASHING COMPOSITION | |
|---|---|
| Nonionic surfactant | 0.4-2.5% |
| Sodium metasilicate | 0-20% |
| Sodium disilicate | 3-20% |
| Sodium triphosphate | 20-40% |
| Sodium carbonate | 0-20% |
| Sodium perborate | 2-9% |
| Tetraacetyl ethylene diamine (TAED) | 1-4% |
| Sodium sulphate | 5-33% |
| Enzymes (e.g. alpha-amylase polypeptide) | 0.0001-0.1% |

| (b) POWDER AUTOMATIC DISHWASHING COMPOSITION | |
|---|---|
| Nonionic surfactant | 1-2% |
| Sodium disilicate | 2-30% |
| Sodium carbonate | 10-50% |
| Sodium phosphonate | 0-5% |
| Trisodium citrate dihydrate | 9-30% |
| Nitrilotrisodium acetate (NTA) | 0-20% |
| Sodium perborate monohydrate | 5-10% |
| Tetraacetyl ethylene diamine (TAED) | 1-2% |
| Polyacrylate polymer (e.g. maleic acid/acrylic acid copolymer) | 6-25% |
| Enzymes (e.g. alpha-amylase polypeptide) | 0.0001-0.1% |
| Perfume | 0.1-0.5% |
| Water | 5-10% |

| (c) POWDER AUTOMATIC DISHWASHING COMPOSITION | |
|---|---|
| Nonionic surfactant | 0.5-2.0% |
| Sodium disilicate | 25-40% |
| Sodium citrate | 30-55% |
| Sodium carbonate | 0-29% |
| Sodium bicarbonate | 0-20% |
| Sodium perborate monohydrate | 0-15% |
| Tetraacetyl ethylene diamine (TAED) | 0-6% |
| Maleic acid/acrylic acid copolymer | 0-5% |
| Clay | 1-3% |
| Polyamino acids | 0-20% |
| Sodium polyacrylate | 0-8% |
| Enzymes (e.g. alpha-amylase polypeptide) | 0.0001-0.1% |

| (d) POWDER AUTOMATIC DISHWASHING COMPOSITION | |
| --- | --- |
| Nonionic surfactant | 1-2% |
| Zeolite MAP | 15-42% |
| Sodium disilicate | 30-34% |
| Sodium citrate | 0-12% |
| Sodium carbonate | 0-20% |
| Sodium perborate monohydrate | 7-15% |
| Tetraacetyl ethylene diamine (TAED) | 0-3% |
| Polymer | 0-4% |
| Maleic acid/acrylic acid copolymer | 0-5% |
| Organic phosphonate | 0-4% |
| Clay | 1-2% |
| Enzymes (e.g. alpha-amylase polypeptide) | 0.0001-0.1% |
| Sodium sulphate | Balance |

| (e) POWDER AUTOMATIC DISHWASHING COMPOSITION | |
| --- | --- |
| Nonionic surfactant | 1-7% |
| Sodium disilicate | 18-30% |
| Trisodium citrate | 10-24% |
| Sodium carbonate | 12-20% |
| Monopersulphate (2 $KHSO_5 \cdot KHSO_4 \cdot K_2SO_4$) | 15-21% |
| Bleach stabilizer | 0.1-2% |
| Maleic acid/acrylic acid copolymer | 0-6% |
| Diethylene triamine pentaacetate, pentasodium salt | 0-2.5% |
| Enzymes (e.g. alpha-amylase polypeptide) | 0.0001-0.1% |
| Sodium sulphate, water | Balance |

| (f) POWDER AND LIQUID DISHWASHING COMPOSITION WITH CLEANING SURFACTANT SYSTEM | |
| --- | --- |
| Nonionic surfactant | 0-1.5% |
| Octadecyl dimethylamine N-oxide dihydrate | 0-5% |
| 80:20 wt. C18/C16 blend of octadecyl dimethylamine N-oxide dihydrate and hexadecyldimethyl amine N-oxide dihydrate | 0-4% |
| 70:30 wt. C18/C16 blend of octadecyl bis (hydroxyethyl)amine N-oxide anhydrous and hexadecyl bis (hydroxyethyl)amine N-oxide anhydrous | 0-5% |
| $C_{13}$-$C_{15}$ alkyl ethoxysulfate with an average degree of ethoxylation of 3 | 0-10% |
| $C_{12}$-$C_{15}$ alkyl ethoxysulfate with an average degree of ethoxylation of 3 | 0-5% |
| $C_{13}$-$C_{15}$ ethoxylated alcohol with an average degree of ethoxylation of 12 | 0-5% |
| A blend of $C_{12}$-$C_{15}$ ethoxylated alcohols with an average degree of ethoxylation of 9 | 0-6.5% |
| A blend of $C_{13}$-$C_{15}$ ethoxylated alcohols with an average degree of ethoxylation of 30 | 0-4% |
| Sodium disilicate | 0-33% |
| Sodium tripolyphosphate | 0-46% |
| Sodium citrate | 0-28% |
| Citric acid | 0-29% |
| Sodium carbonate | 0-20% |
| Sodium perborate monohydrate | 0-11.5% |
| Tetraacetyl ethylene diamine (TAED) | 0-4% |
| Maleic acid/acrylic acid copolymer | 0-7.5% |
| Sodium sulphate | 0-12.5% |
| Enzymes (e.g. alpha-amylase polypeptide) | 0.0001-0.1% |

| (p) NON-AQUEOUS LIQUID AUTOMATIC DISHWASHING COMPOSITION | |
| --- | --- |
| Liquid nonionic surfactant (e.g. alcohol ethoxylates) | 2.0-10.0% |
| Alkali metal silicate | 3.0-15.0% |
| Alkali metal phosphate | 20.0-40.0% |
| Liquid carrier selected from higher glycols, polyglycols, polyoxides, glycolethers | 25.0-45.0% |
| Stabilizer (e.g. a partial ester of phosphoric acid and a $C_{16}$-$C_{18}$ alkanol) | 0.5-7.0% |
| Foam suppressor (e.g. silicone) | 0-1.5% |
| Enzymes (e.g. alpha-amylase polypeptide) | 0.0001-0.1% |

| (q) NON-AQUEOUS LIQUID DISHWASHING COMPOSITION | |
| --- | --- |
| Liquid nonionic surfactant (e.g. alcohol ethoxylates) | 2.0-10.0% |
| Sodium silicate | 3.0-15.0% |
| Alkali metal carbonate | 7.0-20.0% |
| Sodium citrate | 0.0-1.5% |
| Stabilizing system (e.g. mixtures of finely divided silicone and low molecular weight dialkyl polyglycol ethers) | 0.5-7.0% |
| Low molecule weight polyacrylate polymer | 5.0-15.0% |
| Clay gel thickener (e.g. bentonite) | 0.0-10.0% |
| Hydroxypropyl cellulose polymer | 0.0-0.6% |
| Enzymes (e.g. alpha-amylase polypeptide) | 0.0001-0.1% |
| Liquid carrier selected from higher lycols, polyglycols, polyoxides and glycol ethers | Balance |

| (r) THIXOTROPIC LIQUID AUTOMATIC DISHWASHING COMPOSITION | |
| --- | --- |
| $C_{12}$-$C_{14}$ fatty acid | 0-0.5% |
| Block co-polymer surfactant | 1.5-15.0% |
| Sodium citrate | 0-12% |
| Sodium tripolyphosphate | 0-15% |
| Sodium carbonate | 0-8% |
| Aluminium tristearate | 0-0.1% |
| Sodium cumene sulphonate | 0-1.7% |
| Polyacrylate thickener | 1.32-2.5% |
| Sodium polyacrylate | 2.4-6.0% |
| Boric acid | 0-4.0% |
| Sodium formate | 0-0.45% |
| Calcium formate | 0-0.2% |
| Sodium n-decydiphenyl oxide disulphonate | 0-4.0% |
| Monoethanol amine (MEA) | 0-1.86% |
| Sodium hydroxide (50%) | 1.9-9.3% |
| 1,2-Propanediol | 0-9.4% |
| Enzymes (e.g. alpha-amylase polypeptide) | 0.0001-0.1% |
| Suds suppressor, dye, perfumes, water | Balance |

| (s) LIQUID AUTOMATIC DISHWASHING COMPOSITION | |
| --- | --- |
| Alcohol ethoxylate | 0-20% |
| Fatty acid ester sulphonate | 0-30% |
| Sodium dodecyl sulphate | 0-20% |
| Alkyl polyglycoside | 0-21% |
| Oleic acid | 0-10% |
| Sodium disilicate monohydrate | 18-33% |
| Sodium citrate dihydrate | 18-33% |
| Sodium stearate | 0-2.5% |
| Sodium perborate monohydrate | 0-13% |
| Tetraacetyl ethylene diamine (TAED) | 0-8% |
| Maleic acid/acrylic acid copolymer | 4-8% |
| Enzymes (e.g. alpha-amylase polypeptide) | 0.0001-0.1% |

| (t) LIQUID AUTOMATIC DISHWASHING COMPOSITION CONTAINING PROTECTED BLEACH PARTICLES | |
| --- | --- |
| Sodium silicate | 5-10% |
| Tetrapotassium pyrophosphate | 15-25% |
| Sodium triphosphate | 0-2% |
| Potassium carbonate | 4-8% |

| (t) LIQUID AUTOMATIC DISHWASHING COMPOSITION CONTAINING PROTECTED BLEACH PARTICLES | |
| --- | --- |
| Protected bleach particles, e.g. chlorine | 5-10% |
| Polymeric thickener | 0.7-1.5% |
| Potassium hydroxide | 0-2% |
| Enzymes (e.g. alpha-amylase polypeptide) | 0.0001-0.1% |
| Water | Balance |

(u) Automatic dishwashing compositions as described in (a), (b), (c), (d), (f) and (j), wherein perborate is replaced by percarbonate.

(v) Automatic dishwashing compositions as described in (a) to (f) which additionally contain a manganese catalyst. The manganese catalyst may, e.g., be one of the compounds described in "Efficient manganese catalysts for low-temperature bleaching", *Nature* 369, 1994, pp. 637-639.

Uses

The present invention is also directed to methods for using an alpha-amylase polypeptide of the invention in detergents, in particular laundry detergent compositions and dishwashing detergent compositions.

Thus, the invention provides the use of an alpha-amylase polypeptide or composition of the invention, in a domestic or industrial cleaning process.

In one embodiment, the use is cleaning of fabric, for example laundry.

In another embodiment, the use is cleaning of ceramic, plastic or glass material, for example dishwashing.

Accordingly, the alpha-amylase polypeptides of the invention are applicable as a component in washing, dishwashing, and hard surface cleaning detergent compositions (in either a domestic or industrial setting).

The alpha-amylase variants of this invention possess valuable properties allowing for a variety of other industrial applications. For example, alpha-amylase polypeptides of the invention may be used for starch processes, in particular starch conversion, especially liquefaction of starch (see, e.g., U.S. Pat. No. 3,912,590, EP patent application nos. 252 730 and 63 909, WO 99/19467, and WO 96/28567 all references hereby incorporated by reference). Also contemplated are compositions for starch conversion purposes, which may beside the variant of the invention also comprise a glucoamylase, pullulanase, and other alpha-amylases.

Furthermore, alpha-amylase variants of this invention are also particularly useful in the production of sweeteners and ethanol (see, e.g., U.S. Pat. No. 5,231,017 hereby incorporated by reference), such as fuel, drinking and industrial ethanol, from starch or whole grains.

Alpha-amylase variants of the invention may also be useful for desizing of textiles, fabrics and garments (see, e.g., WO 95/21247, U.S. Pat. No. 4,643,736, EP 119,920 hereby in corporate by reference), beer making or brewing, in pulp and paper production.

Starch Conversion

Conventional starch-conversion processes, such as liquefaction and saccharification processes are described, e.g., in U.S. Pat. No. 3,912,590 and EP patent publications Nos. 252,730 and 63,909, hereby incorporated by reference.

In an embodiment the starch conversion process degrading starch to lower molecular weight carbohydrate components such as sugars or fat replacers includes a debranching step.

In the case of converting starch into a sugar, the starch is depolymerized. Such depolymerization processes may consist of a pre-treatment step and two or three consecutive process steps, viz. a liquefaction process, a saccharification process and dependent on the desired end product optionally an isomerization process.

(i) Pre-Treatment of Native Starch

Native starch consists of microscopic granules, which are insoluble in water at room temperature. When an aqueous starch slurry is heated, the granules swell and eventually burst, dispersing the starch molecules into the solution. During this "gelatinization" process there is a dramatic increase in viscosity. As the solids level is 30-40% in a typically industrial process, the starch has to be thinned or "liquefied" so that it can be handled. This reduction in viscosity is today mostly obtained by enzymatic degradation.

(ii) Liquefaction

During the liquefaction step, the long chained starch is degraded into branched and linear shorter units (maltodextrins) by an alpha-amylase. The liquefaction process is carried out at 105-110° C. for 5 to 10 minutes followed by 1-2 hours at 95° C. The pH lies between 5.5 and 6.2. In order to ensure optimal enzyme stability under these conditions, 1 mM of calcium is added (40 ppm free calcium ions). After this treatment the liquefied starch will have a "dextrose equivalent" (DE) of 10-15.

(iii) Saccharification

After the liquefaction process the maltodextrins are converted into dextrose by addition of a glucoamylase (e.g., AMG) and a debranching enzyme, such as an isoamylase (U.S. Pat. No. 4,335,208) or a pullulanase (e.g., Promozyme™) (U.S. Pat. No. 4,560,651). Before this step the pH is reduced to a value below 4.5, maintaining the high temperature (above 95° C.) to inactivate the liquefying alpha-amylase to reduce the formation of short oligosaccharide called "panose precursors" which cannot be hydrolyzed properly by the debranching enzyme.

The temperature is lowered to 60° C., and glucoamylase and debranching enzyme are added. The saccharification process proceeds for 24-72 hours.

Normally, when denaturing the α-amylase after the liquefaction step about 0.2-0.5% of the saccharification product is the branched trisaccharide 6<2>-alpha-glucosyl maltose (panose) which cannot be degraded by a pullulanase. If active amylase from the liquefaction step is present during saccharification (i.e., no denaturing), this level can be as high as 1-2%, which is highly undesirable as it lowers the saccharification yield significantly.

(iv) Isomerization

When the desired final sugar product is, e.g., high fructose syrup the dextrose syrup may be converted into fructose. After the saccharification process the pH is increased to a value in the range of 6-8, preferably pH 7.5, and the calcium is removed by ion exchange. The dextrose syrup is then converted into high fructose syrup using, e.g., an immmobilized glucoseisomerase (such as Sweetzyme<™> IT).

Ethanol Production

In general alcohol production (ethanol) from whole grain can be separated into 4 main steps Milling
Liquefaction
Saccharification
Fermentation (i) Milling The grain is milled in order to open up the structure and allowing for further processing. Two processes are used wet or dry milling. In dry milling the whole kernel is milled and used in the remaining part of the process. Wet milling gives a very good separation of germ and meal (starch granules and protein) and is with a few exceptions applied at locations where there is a parallel production of syrups.

(ii) Liquefaction

In the liquefaction process the starch granules are solubilized by hydrolysis to maltodextrins mostly of a DP higher than 4. The hydrolysis may be carried out by acid treatment or enzymatically by alpha-amylase. Acid hydrolysis is used on a limited basis. The raw material can be milled whole grain or a side stream from starch processing.

Enzymatic liquefaction is typically carried out as a three-step hot slurry process. The slurry is heated to between 60-95° C., preferably 80-85° C., and the enzyme(s) is (are) added. Then the slurry is jet-cooked at between 95-140° C., preferably 105-125° C., cooled to 60-95° C. and more enzyme(s) is (are) added to obtain the final hydrolysis. The liquefaction process is carried out at pH 4.5-6.5, typically at a pH between 5 and 6. Milled and liquefied grain is also known as mash.

(iii) Saccharification

To produce low molecular sugars DP1-3 that can be metabolized by yeast, the maltodextrin from the liquefaction must be further hydrolyzed. The hydrolysis is typically done enzymatically by glucoamylases, alternatively alpha-glucosidases or acid alpha-amylases can be used. A full saccharification step may last up to 72 hours, however, it is common only to do a pre-saccharification of typically 40-90 minutes and then complete saccharification during fermentation (SSF). Saccharification is typically carried out at temperatures from 30-65° C., typically around 60° C., and at pH 4.5.

(iv) Fermentation

Yeast typically from *Saccharomyces* spp. is added to the mash and the fermentation is ongoing for 24-96 hours, such as typically 35-60 hours. The temperature is between 26-34° C., typically at about 32° C., and the pH is from pH 3-6, preferably around pH 4-5.

Note that the most widely used process is a simultaneous saccharification and fermentation (SSF) process where there is no holding stage for the saccharification, meaning that yeast and enzyme is added together. When doing SSF it is common to introduce a pre-saccharification step at a temperature above 50° C., just prior to the fermentation.

(v) Distillation

Following the fermentation the mash is distilled to extract the ethanol.

The ethanol obtained according to the process of the invention may be used as, e.g., fuel ethanol; drinking ethanol, i.e., potable neutral spirits; or industrial ethanol.

(vi) By-Products

Left over from the fermentation is the grain, which is typically used for animal feed either in liquid form or dried.

Further details on how to carry out liquefaction, saccharification, fermentation, distillation, and recovering of ethanol are well known to the skilled person.

According to the process of the invention the saccharification and fermentation may be carried out simultaneously or separately.

Pulp and Paper Production

Alkaliine alpha-amylase polypeptides of the invention may also be used in the production of lignocellulosic materials, such as pulp, paper and cardboard, from starch reinforced waste paper and cardboard, especially where re-pulping occurs at pH above 7 and where amylases facilitate the disintegration of the waste material through degradation of the reinforcing starch. The alpha-amylase of the invention is especially useful in a process for producing a papermaking pulp from starch-coated printed-paper. The process may be performed as described in WO 95/14807, comprising the following steps:

a) disintegrating the paper to produce a pulp,
b) treating with a starch-degrading enzyme before, during or after step a), and
c) separating ink particles from the pulp after steps a) and b).

The alpha-amylases of the invention may also be very useful in modifying starch where enzymatically modified starch is used in papermaking together with alkaline fillers such as calcium carbonate, kaolin and clays. With the alkaline alpha-amylases of the invention it becomes possible to modify the starch in the presence of the filler thus allowing for a simpler integrated process.

Desizing of Textiles, Fabrics and Garments

An alpha-amylase of the invention may also be very useful in textile, fabric or garment desizing. In the textile processing industry, alpha-amylases are traditionally used as auxiliaries in the desizing process to facilitate the removal of starch-containing size, which has served as a protective coating on weft yarns during weaving. Complete removal of the size coating after weaving is important to ensure optimum results in the subsequent processes, in which the fabric is scoured, bleached and dyed. Enzymatic starch breakdown is preferred because it does not involve any harmful effect on the fiber material. In order to reduce processing cost and increase mill throughput, the desizing processing is sometimes combined with the scouring and bleaching steps. In such cases, non-enzymatic auxiliaries such as alkali or oxidation agents are typically used to break down the starch, because traditional alpha-amylases are not very compatible with high pH levels and bleaching agents. The non-enzymatic breakdown of the starch size does lead to some fiber damage because of the rather aggressive chemicals used. Accordingly, it would be desirable to use the alpha-amylases of the invention as they have an improved performance in alkaline solutions. The alpha-amylases may be used alone or in combination with a cellulase when desizing cellulose-containing fabric or textile.

Desizing and bleaching processes are well known in the art. For instance, such processes are described in WO 95/21247, U.S. Pat. No. 4,643,736, EP 119,920 hereby incorporate by reference.

Commercially available products for desizing include AQUAZYME® and AQUAZYME® ULTRA from Novozymes NS.

Beer Making

The alpha-amylases of the invention may also be very useful in a beer-making process; the alpha-amylases will typically be added during the mashing process.

The present invention is further described by the following examples that should not be construed as limiting the scope of the invention.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

EXAMPLES

Example 1: Assays for Alpha-Amylase Activity

1. Phadebas Assay

Alpha-amylase activity may be determined by a method employing Phadebas® tablets as substrate. Phadebas tablets (Phadebas® Amylase Test, supplied by Pharmacia Diagnostic) contain a cross-linked insoluble blue-colored starch polymer, which has been mixed with bovine serum albumin and a buffer substance and tableted.

For every single measurement one tablet is suspended in a tube containing 5 ml 50 mM Britton-Robinson buffer (50 mM acetic acid, 50 mM phosphoric acid, 50 mM boric acid, 0.1 mM CaCl2), pH adjusted to the value of interest with NaOH). The test is performed in a water bath at the temperature of interest. The alpha-amylase to be tested is diluted in x ml of 50 mM Britton-Robinson buffer. 1 ml of this alpha-amylase solution is added to the 5 ml 50 mM Britton-Robinson buffer. The starch is hydrolyzed by the alpha-amylase giving soluble blue fragments. The absorbance of the resulting blue solution, measured spectrophotometrically at 620 nm, is a function of the alpha-amylase activity.

It is important that the measured 620 nm absorbance after 10 or 15 minutes of incubation (testing time) is in the range of 0.2 to 2.0 absorbance units at 620 nm. In this absorbance range there is linearity between activity and absorbance (Lambert-Beer law). The dilution of the enzyme must therefore be adjusted to fit this criterion. Under a specified set of conditions (temp., pH, reaction time, buffer conditions) 1 mg of a given alpha-amylase will hydrolyze a certain amount of substrate and a blue colour will be produced. The colour intensity is measured at 620 nm. The measured absorbance is directly proportional to the specific activity (activity/mg of pure alpha-amylase protein) of the alpha-amylase in question under the given set of conditions.

2. Alternative Method

Alpha-amylase activity is determined by a method employing the PNP-G7 substrate. PNP-G7 which is an abbreviation for p-nitrophenyl-alpha, D-maltoheptaoside is a blocked oligosaccharide which can be cleaved by an endo-amylase. Following the cleavage, the alpha-Glucosidase included in the kit digest the substrate to liberate a free PNP molecule which has a yellow colour and thus can be measured by visible spectophometry at λ=405 nm (400-420 nm). Kits containing PNP-G7 substrate and alpha-Glucosidase is manufactured by Boehringer-Mannheim (cat. No. 1054635).

To prepare the reagent solution 10 ml of substrate/buffer solution is added to 50 ml enzyme/buffer solution as recommended by the manufacturer. The assay is performed by transferring 20 micro I sample to a 96 well microtitre plate and incubating at 25° C. 200 micro I reagent solution pre-equilibrated to 25° C. is added. The solution is mixed and pre-incubated 1 minute and absorption is measured every 30 sec. over 4 minutes at OD 405 nm in an ELISA reader.

The slope of the time dependent absorption-curve is directly proportional to the activity of the alpha-amylase in question under the given set of conditions.
Determination of LAS Sensitivity The variant is incubated with different concentrations of LAS (linear alkyl benzene sulphonate; Nansa 1169/P) for 10 minutes at 40° C.

The residual activity is determined using the Phadebas® assay method or the alternative method employing the PNP-G7 substrate.

LAS is diluted in 0.1 M phosphate buffer pH 7.5.

The following concentrations are used: 500 ppm, 250 ppm, 100 ppm, 50 ppm, 25 ppm, and 10 ppm on no LAS. The variant is diluted in the different LAS buffers to concentration of 0.01-5 mg/l in a total volume of 10 ml and incubated for 10 minutes in a temperature controlled water bath. The incubation is stopped by transferring a small aliquot into cold assay buffer. It is important that during activity measurement the LAS concentration is below 1 ppm, in order not to affect the activity measurement.

Then the residual activity is determined in duplicate using the above mentioned Phadebas® assay or alternative method. The activity is measured after subtraction of the blank. The activity with no LAS is 100%.

Example 2: Assessment of Wash Performance of Alpha-Amylase Polypeptides of the Invention Using Full Scale Automatic Dish Wash (ADW)

In order to assess the wash performance of the polypeptides of the present invention in a detergent base composition, washing experiments may be performed using full scale Automatic Dish Wash (ADW). The full scale ADW setup is used for testing the wash performance of polypeptides in test conditions mimicking a regular consumer setup.

In the present study, test conditions were a regular 50° C. wash program and a short 40° C. program using a Miele Dishwasher Miele G4300 SCU machine.
General Wash Performance Description.

Melamine tiles stained with starch (DM-77/DM-177/DM-277/DM-377 from Center For Test materials BV, P.O. Box 120, 3133 KT, Vlaardingen, The Netherlands) was used as test material and washed at set programs at 40° C. and 50° C. using tap water with 19-20° dH, as specified below (see Tables 2, 3 and 4). When the detergent dispenser lid opened in the dishwasher, the detergent and the alpha-amylase was added at a concentration of 1.5 mg polypeptide/wash or 3 mg polypeptide/wash for the 40° C. wash, or 0.5 mg polypeptide/wash or 1 mg polypeptide/wash for the 50° C. wash. The test with 0 mg polypeptide/L was used as a blank and corresponded to the contribution from the detergent. The full scale wash performance experiments were conducted under the experimental conditions specified below:

TABLE 2

| | Experimental condition |
|---|---|
| Detergent | Powder ADW model detergent with bleach (see Table B1 or powder model detergent without bleach (see Table B2) |
| Detergent dosage | 21.27 g/wash (with bleach) or 18.61 g/L (without bleach) |
| pH | As is |
| Wash time | Set program. |
| Temperature | 40° C. or 50° C. |
| Water hardness | Tap water |

TABLE 2-continued

| | Experimental condition |
|---|---|
| Polypeptide concentration in test | 40° C.: 1.5 mg polypeptide/wash or 3 mg polypeptide/wash<br>50° C.: 0.5 mg polypeptide/wash or 1 mg polypeptide/wash |
| Test material | DM-77 and DM-177 at 40° C. or DM-277 and DM-377 at 50° C. All mixed starch melamine tiles. |
| Ballast soil | 50 g IKW ballast soil (mixture of fat constituents, protein constitutents, powdered constituents and other constituents - defined by IKW standard |

TABLE 3

ADW model detergent with bleach

| Compound | Content active ingredients | Fraction active component |
|---|---|---|
| MGDA (Trilon M Granules SG) | 20% | 59% |
| Sodium citrate | 20% | 100% |
| Sodium carbonate | 20% | 100% |
| Sodium percarbonate | 10% | 88% |
| Sodium Silicate | 5% | 80% |
| Sodium sulfate | 12% | 100% |
| Acusol 588G | 5% | 92% |
| TAED | 3% | 92% |
| Surfac 23-6.5 | 5% | 100% |

TABLE 4

ADW model detergent without bleach

| Compund | Content active ingredients | Fraction active component |
|---|---|---|
| MGDA (Trilon M Granules SG) | 23% | 59% |
| Sodium citrate | 23% | 100% |
| Sodium carbonate | 23% | 100% |
| Sodium Silicate | 6% | 80% |
| Sodium sulfate | 14% | 100% |
| Acusol 588G | 6% | 92% |
| Surfac 23-6.5 | 6% | 100% |

After washing the melamine tiles were dried.

The wash performance was measured as difference in remission between washed tiles and unwashed tiles. The remission measurements were made with a Color-Eye 7000 (CE7000) used for taking spectra and performing calculations of remission. The remission was measured at 460 nm with no UV light in the illuminant.

The wash performance was considered to be improved if the Improvement Factor (IF) is at least 1.0, preferably at least 1.2 in one or more of the conditions listed above; i.e. either at 40° C. or 50° C., where the variant concentration was 1.5 mg polypeptide/wash or 3 mg polypeptide/wash at 40° C. wash and 0.5 mg polypeptide/wash or 1 mg polypeptide/wash.

The wash performances of exemplary polypeptides of the invention obtained by full scale wash are shown in Table 5a (40° C.) and Table 5b (50° C.) (wherein wash performance score is relative to the wash performance of the parent alpha-amylase of SEQ ID NO:1).

TABLE 5a

ADW wash performance of exemplary polypeptides of the invention

| aa sequence of polypeptide (mutations are relative to SEQ ID NO: 2) | 40° C. - DM177 tiles - 1.5 mg protein/wash | 40° C. - DM177 tiles - 3 mg protein/wash | 40° C. - DM77 tiles - 1.5 mg protein/wash | 40° C. - DM77 tiles - 3 mg protein/wash |
|---|---|---|---|---|
| SEQ ID NO: 1 + S40T | 1.0 | 0.9 | 1.0 | 1.0 |
| SEQ ID NO: 1 + K269N | 1.0 | 0.9 | 1.0 | 1.1 |
| SEQ ID NO: 1 + Y299F | 1.1 | 0.9 | 1.0 | 1.0 |
| SEQ ID NO: 1 + W167Y | 1.2 | 1.2 | 1.1 | 1.1 |
| SEQ ID NO: 1 + H210N | 0.9 | 1.0 | 1.1 | 1.0 |
| SEQ ID NO: 1 + S339A | 1.0 | 1.1 | 1.0 | 1.0 |
| SEQ ID NO: 1 + V366I | 1.0 | 0.9 | 1.0 | 1.0 |
| SEQ ID NO: 1 + K118Q | 1.1 | 1.0 | 1.1 | 0.9 |
| SEQ ID NO: 1 + K118H | 1.1 | 1.0 | 1.3 | 1.1 |
| SEQ ID NO: 1 + W167Y + H210N + S339A | 1.3 | 1.2 | 1.3 | 1.1 |
| SEQ ID NO: 1 + W48F + W167Y + H210N + S339A + V336I | 1.4 | 1.1 | 1.5 | 1.1 |
| SEQ ID NO: 1 + W167Y + H210N + Y299F + S339A + V366I | 1.2 | 1.0 | 1.3 | 1.0 |
| SEQ ID NO: 1 + W48F + W167Y + H210N + Y299F + S339A + V366I | 1.3 | 1.1 | 1.4 | 1.1 |
| SEQ ID NO: 1 + K37R | 1.0 | 0.8 | 0.9 | 0.9 |
| SEQ ID NO: 1 + V238A S334T W482Y | 1.4 | 1.2 | 1.2 | 1.2 |

TABLE 5a-continued

ADW wash performance of exemplary polypeptides of the invention

| aa sequence of polypeptide (mutations are relative to SEQ ID NO: 2) | 40° C. - DM177 tiles - 1.5 mg protein/wash | 40° C. - DM177 tiles - 3 mg protein/wash | 40° C. - DM77 tiles - 1.5 mg protein/wash | 40° C. - DM77 tiles - 3 mg protein/wash |
|---|---|---|---|---|
| SEQ ID NO: 1 + Y243F S334T | 1.3 | 1.2 | 1.3 | 1.1 |
| SEQ ID NO: 1 + A51T L202M S339A | 1.4 | 1.1 | 1.3 | 1.1 |
| SEQ ID NO: 1 + A51T L202M | 1.1 | 0.9 | 0.9 | 1.0 |

TABLE 5b

ADW wash performance of exemplary polypeptides of the invention

| aa sequence of polypeptide (mutations are relative to SEQ ID NO: 2) | 50° C. - DM277 tiles 0.5 mg protein/wash | 50° C. - DM277 tiles 1 mg protein/wash | 50° C. - DM377 tiles 0.5 mg protein/wash | 50° C. - DM377 tiles 1 mg protein/wash |
|---|---|---|---|---|
| SEQ ID NO: 1 + V366I | 1.7 | 1.1 | 1.5 | 1.1 |
| SEQ ID NO: 1 + K269N | 0.9 | 1.0 | 1.1 | 1.1 |
| SEQ ID NO: 1 + S40T | 1.5 | 1.1 | 1.5 | 1.1 |
| SEQ ID NO: 1 + Y299F | 1.3 | 1.1 | 1.5 | 1.2 |
| SEQ ID NO: 1 + S255K | 1.6 | 1.2 | 1.4 | 1.1 |
| SEQ ID NO: 1 + H210N | 1.7 | 1.1 | 1.6 | 1.0 |
| SEQ ID NO: 1 + W167Y | 1.7 | 1.2 | 1.6 | 1.1 |
| SEQ ID NO: 1 + S339A | 1.9 | 1.2 | 1.9 | 1.1 |
| SEQ ID NO: 1 + K118H | 1.3 | 1.1 | 1.1 | 1.2 |
| SEQ ID NO: 1 + K118Q | 1.3 | 1.0 | 1.1 | 1.2 |
| SEQ ID NO: 1 + K385R | 1.5 | 1.1 | 1.2 | 1.2 |
| SEQ ID NO: 1 + E138Q | 1.4 | 1.0 | 1.3 | 1.2 |
| SEQ ID NO: 1 + K37R | 1.4 | 1.1 | 1.3 | 1.2 |
| SEQ ID NO: 1 + W482Y | 1.2 | 1.0 | 1.4 | 1.2 |
| SEQ ID NO: 1 + M116F | 1.4 | 1.1 | 1.7 | 1.2 |
| SEQ ID NO: 1 + W167Y + H210N + S339A + V366I | 1.6 | 1.1 | 2.0 | 1.3 |
| SEQ ID NO: 1 + W167Y + H210N + S339A | 1.7 | 1.1 | 2.2 | 1.3 |
| SEQ ID NO: 1 + W167Y + L202M | 1.3 | 1.1 | 1.1 | 1.0 |
| SEQ ID NO: 1 + W48F + W167Y + H210N + S339A | 2.1 | 1.2 | 2.0 | 1.2 |
| SEQ ID NO: 1 + Y243F | 1.3 | 1.1 | 1.4 | 1.2 |
| SEQ ID NO: 1 + W48F | 2.0 | 1.2 | 2.5 | 1.4 |
| SEQ ID NO: 1 + D30N + N33D + K37V + K383R | 0.9 | 1.1 | 1.2 | 1.0 |
| SEQ ID NO: 1 + W48F + W167Y + H210N + Y299F + S339A + V366I | 1.4 | 1.1 | 1.7 | 1.2 |
| SEQ ID NO: 1 + W167Y + H210N + Y299F + S339A + V366I | 1.6 | 1.2 | 1.9 | 1.2 |
| SEQ ID NO: 1 + V238A S334T W482Y | 1.8 | 1.3 | 1.8 | 1.2 |
| SEQ ID NO: 1 + Y243F S334T | 2.4 | 1.3 | 2.8 | 1.3 |
| SEQ ID NO: 1 + A51T L202M N270G | 1.2 | 1.0 | 1.3 | 1.1 |
| SEQ ID NO: 1 + A51T F195N L202M | 1.8 | 1.1 | 1.8 | 1.1 |
| SEQ ID NO: 1 + A51T L202M S365C | 1.9 | 1.1 | 1.9 | 1.1 |
| SEQ ID NO: 1 + A51T A186D L202M N270G N402Y | 1.1 | 1.1 | 1.1 | 1.1 |
| SEQ ID NO: 1 + A186D L202M N270G N402Y | 1.4 | 1.1 | 1.4 | 1.1 |
| SEQ ID NO: 1 + A51T L202M Q311R | 1.8 | 1.2 | 1.8 | 1.2 |
| SEQ ID NO: 1 + A51T L202M S339A | 1.8 | 1.2 | 1.8 | 1.2 |

TABLE 5b-continued

ADW wash performance of exemplary polypeptides of the invention

| aa sequence of polypeptide (mutations are relative to SEQ ID NO: 2) | 50° C. - DM277 tiles 0.5 mg protein/wash | 50° C. - DM277 tiles 1 mg protein/wash | 50° C. - DM377 tiles 0.5 mg protein/wash | 50° C. - DM377 tiles 1 mg protein/wash |
|---|---|---|---|---|
| SEQ ID NO: 1 + K37V A51T L202M | 1.6 | 1.2 | 1.8 | 1.2 |
| SEQ ID NO: 1 + A51T L202M | 1.7 | 1.3 | 2.1 | 1.2 |
| SEQ ID NO: 1 + A51T K108R L202M | 1.8 | 1.2 | 2.2 | 1.2 |
| SEQ ID NO: 1 + A186G | 1.1 | 1.1 | 1.1 | 1.1 |
| SEQ ID NO: 1 + W48F V238A S334T | 1.9 | 1.2 | 1.9 | 1.2 |
| SEQ ID NO: 1 + L202M T246V N270G S334T | 1.0 | 1.1 | 1.4 | 1.1 |
| SEQ ID NO: 1 + S334T | 1.7 | 1.2 | 1.9 | 1.3 |
| SEQ ID NO: 1 + A51T K142R L202M N270G | 2.1 | 1.2 | 2.9 | 1.4 |

Example 3: Assessment of Wash Performance of Alpha-Amylase Polypeptides of the Invention Using Full Scale Automatic Mechanical Stress Assay (AMSA)

In order to assess the wash performance of the polypeptides of the present invention in a detergent base composition, washing experiments may also be performed using Automatic Mechanical Stress Assay (AMSA). With the AMSA test, the wash performance of a large quantity of small volume enzyme-detergent solutions can be examined. The AMSA plate has a number of slots for test solutions and a lid firmly squeezing the textile swatch to be washed against all the slot openings. During the washing time, the plate, test solutions, textile and lid were vigorously shaken to bring the test solution in contact with the textile and apply mechanical stress in a regular, periodic oscillating manner. For further details, see WO 02/42740 (especially the paragraph "Special method embodiments" at page 23-24, the disclosure of which is incorporated herein by reference).

General Wash Performance Description

A test solution comprising water (21° dH), 3.94 g/L ADW model detergent with bleach or 3.45 g/L ADW model detergent without bleach, as specified below (see Tables 6, 7 and 8), and the polypeptide of the invention at concentrations of 0.03, 0.06, 0.12 and 0.24 mg polypeptide protein/L (40° C.) or 0.01, 0.03, 0.06 and 0.12 mg polypeptide protein/L (50° C.), was prepared. Fabrics stained with starch (CS-28 from Center For Test materials BV, P.O. Box 120, 3133 KT, Vlaardingen, The Netherlands) was added and washed for 10 or 20 minutes at 40° C. and 50° C., as specified below. After thorough rinse under running tap water and drying in the dark, the light intensity values of the stained fabrics were subsequently measured as a measure for wash performance. The test with 0 mg enzyme protein/L was used as a blank and corresponded to the contribution from the detergent. Preferably mechanical action is applied during the wash step, e.g. in the form of shaking, rotating or stirring the wash solution with the fabrics and tiles. The AMSA wash performance experiments were conducted under the experimental conditions specified below:

TABLE 6

| Experimental condition | |
|---|---|
| Detergent | Powder ADW model detergent with bleach (see Table B1) or powder ADW model detergent without bleach (see Table B2) |
| Detergent dosage | 3.94 g/L (with bleach) or 3.45 g/L (without bleach) |
| Test solution volume | 160 micro L |
| pH | As is |
| Wash time | 10 or 20 minutes |
| Temperature | 40° C. or 50° C. |
| Water hardness | 21° dH ($Ca^{2+}:Mg^{2+}:HCO3^-$ = 4:1:10) |
| Enzyme concentration in test | 0.03, 0.06, 0.12 and 0.24 mg enzyme protein/L (40° C.) or 0.01, 0.03, 0.06 and 0.12 mg enzyme protein/L (50° C.) |
| Test material | CS-28 (Rice starch cotton) |

TABLE 7

ADW model detergent with bleach

| Compound | Content active ingredients | Fraction active component |
|---|---|---|
| MGDA (Trilon M Granules SG) | 20% | 59% |
| Sodium citrate | 20% | 100% |
| Sodium carbonate | 20% | 100% |
| Sodium percarbonate | 10% | 88% |
| Sodium Silicate | 5% | 80% |
| Sodium sulfate | 12% | 100% |
| Acusol 588G | 5% | 92% |
| TAED | 3% | 92% |
| Surfac 23-6.5 (liq) | 5% | 100% |

TABLE 8

| ADW model detergent without bleach | | |
|---|---|---|
| Compound | Content active ingredients | Fraction active component |
| MGDA (Trilon M Granules SG) | 23% | 59% |
| Sodium citrate | 23% | 100% |
| Sodium carbonate | 23% | 100% |
| Sodium Silicate | 6% | 80% |
| Sodium sulfate | 14% | 100% |
| Acusol 588G | 6% | 92% |
| Surfac 23-6.5 (liq) | 6% | 100% |

Water hardness was adjusted to 21° dH by addition of CaCl2), MgCl2, and NaHCO3 (Ca$^{2+}$:Mg$^{2+}$:HCO3$^-$=4:1:10) to the test system. After washing the textiles were flushed in tap water and dried.

The wash performance was measured as the brightness expressed as the intensity of the light reflected from the sample when illuminated with white light. When the sample was stained the intensity of the reflected light was lower, than that of a clean sample. Therefore the intensity of the reflected light can be used to measure wash performance.

Color measurements were made with a professional flat-bed scanner (EPSON Expression 10000XL, EPSON) used to capture an image of the washed textile.

To extract a value for the light intensity from the scanned images, 48☐24 Bit Color pixel values from the image were converted into values for red, green and blue (RGB). The intensity value (Int) is calculated by adding the RGB values together as vectors and then taking the length of the resulting vector:

$$Int = \sqrt{r^2 + g^2 + b^2}$$

The wash performances of the variants according to the invention obtained by AMSA are the following;

TABLE 9

| AMSA wash performance of exemplary polypeptides of the invention | | | | |
|---|---|---|---|---|
| | ADW Wash conditions | | | |
| | with bleach | | without bleach | |
| Mutations in SEQ ID NO: 1 (amino acid positions relative to SEQ ID NO: 2) | 40° C.- 10 min- CS28 | 50° C.- 20 min- CS28 | 40° C.- 10 min- CS28 | 50° C.- 20 min- CS28 |
| SEQ ID NO: 1 + V214T | 0.9 | 1.0 | 1.0 | 1.1 |
| SEQ ID NO: 1 + V214I | 0.9 | 1.0 | 0.9 | 1.0 |
| SEQ ID NO: 1 + Y135H | 1.0 | 1.1 | 1.1 | 1.0 |
| SEQ ID NO: 1 + Y203N | 1.0 | 1.1 | 1.1 | 1.2 |
| SEQ ID NO: 1 + W48F | 1.1 | 1.4 | 1.3 | 1.4 |
| SEQ ID NO: 1 + M116V | 1.1 | 1.2 | 1.2 | 1.3 |
| SEQ ID NO: 1 + M116I | 1.0 | 1.2 | 1.0 | 1.2 |
| SEQ ID NO: 1 + M116F | 1.1 | 1.2 | 1.3 | 1.3 |
| SEQ ID NO: 1 + W167Y | 1.1 | 1.1 | 1.3 | 1.2 |
| SEQ ID NO: 1 + W167H | 1.1 | 1.0 | 1.2 | 1.1 |
| SEQ ID NO: 1 + W187Y | 0.7 | 0.8 | 0.8 | 1.0 |
| SEQ ID NO: 1 + W189H | 1.1 | 1.1 | 1.3 | 1.2 |
| SEQ ID NO: 1 + M208V | 1.1 | 1.0 | 1.2 | 1.1 |
| SEQ ID NO: 1 + M208F | 0.9 | 1.1 | 1.1 | 1.1 |
| SEQ ID NO: 1 + M261A | 0.9 | 0.8 | 0.8 | 1.0 |
| SEQ ID NO: 1 + F295Y | 0.9 | 1.1 | 1.1 | 1.1 |
| SEQ ID NO: 1 + F295W | 1.0 | 1.0 | 1.2 | 1.1 |
| SEQ ID NO: 1 + Y298F | 1.0 | 1.1 | 1.2 | 1.2 |
| SEQ ID NO: 1 + Y298W | 1.0 | 1.0 | 1.2 | 1.0 |
| SEQ ID NO: 1 + M105F | 1.0 | 1.1 | 1.0 | 1.0 |
| SEQ ID NO: 1 + M116A | 1.1 | 1.1 | 0.9 | 1.2 |
| SEQ ID NO: 1 + M208L | 1.0 | 1.2 | 0.9 | 1.0 |
| SEQ ID NO: 1 + M10L + M261L | 1.0 | 1.1 | 1.2 | 1.0 |
| SEQ ID NO: 1 + W469F | 1.0 | 0.9 | 0.9 | 1.0 |
| SEQ ID NO: 1 + W187Y + M208L | 1.0 | 1.0 | 1.2 | 1.0 |
| SEQ ID NO: 1 + W482Y | 1.1 | 1.2 | 1.2 | 1.2 |
| SEQ ID NO: 1 + Y203F | 1.0 | 1.1 | 1.0 | 1.2 |
| SEQ ID NO: 1 + G109A | 1.1 | 1.1 | 1.0 | 1.1 |
| SEQ ID NO: 1 + N174Q | 1.1 | 1.3 | 1.0 | 1.2 |
| SEQ ID NO: 1 + N175Q | 1.0 | 1.2 | 1.0 | 1.2 |
| SEQ ID NO: 1 + N174* | 1.0 | 0.9 | 1.0 | 1.2 |
| SEQ ID NO: 1 + N174* + N175Q | 1.0 | 1.2 | 1.0 | 1.1 |
| SEQ ID NO: 1 + I235L | 1.0 | 1.2 | 1.0 | 1.3 |
| SEQ ID NO: 1 + I235M | 0.9 | 1.0 | 1.0 | 0.9 |
| SEQ ID NO: 1 + I235V | 0.8 | 0.7 | 0.8 | 1.2 |
| SEQ ID NO: 1 + V238T | 0.7 | 1.3 | 0.9 | 1.2 |
| SEQ ID NO: 1 + A265G | 1.1 | 1.2 | 1.0 | 1.2 |
| SEQ ID NO: 1 + M105Y | 1.0 | 1.1 | 1.0 | 1.2 |
| SEQ ID NO: 1 + M105F | 1.0 | 1.3 | 1.0 | 1.2 |
| SEQ ID NO: 1 + M105L | 1.1 | 1.1 | 0.9 | 1.2 |
| SEQ ID NO: 1 + M105I | 0.9 | 1.2 | 0.9 | 1.0 |
| SEQ ID NO: 1 + I250L | 1.0 | 1.2 | 0.9 | 1.1 |
| SEQ ID NO: 1 + I250V | 1.0 | 1.3 | 1.0 | 1.1 |
| SEQ ID NO: 1 + K37H | 1.1 | 1.2 | 1.0 | 1.2 |
| SEQ ID NO: 1 + K37V | 0.9 | 0.8 | 0.8 | 1.0 |
| SEQ ID NO: 1 + K37M | 0.9 | 1.2 | 0.9 | 1.1 |

TABLE 9-continued

AMSA wash performance of exemplary polypeptides of the invention

| | ADW Wash conditions | | | |
| --- | --- | --- | --- | --- |
| | with bleach | | without bleach | |
| Mutations in SEQ ID NO: 1 (amino acid positions relative to SEQ ID NO: 2) | 40° C.-10 min-CS28 | 50° C.-20 min-CS28 | 40° C.-10 min-CS28 | 50° C.-20 min-CS28 |
| SEQ ID NO: 1 + K37L | 1.0 | 1.1 | 0.8 | 1.2 |
| SEQ ID NO: 1 + Q311R | 1.1 | 1.3 | 0.9 | 1.2 |
| SEQ ID NO: 1 + Y203H | 1.0 | 1.1 | 0.9 | 1.2 |
| SEQ ID NO: 1 + I206L | 1.1 | 1.3 | 0.9 | 1.1 |
| SEQ ID NO: 1 + T182G | 1.0 | 1.2 | 1.0 | 1.3 |
| SEQ ID NO: 1 + Y243F + F267Y | 0.9 | 1.1 | 1.0 | 1.1 |
| SEQ ID NO: 1 + K37V + P45R + K383R | 0.9 | 1.0 | 0.9 | 1.0 |
| SEQ ID NO: 1 + D30N + N33D + K37V + K383R | 1.0 | 1.1 | 1.0 | 1.0 |
| SEQ ID NO: 1 + M116L | 1.1 | 1.3 | 1.2 | 1.2 |
| SEQ ID NO: 1 + N25K | 0.9 | 1.2 | 0.9 | 1.0 |
| SEQ ID NO: 1 + S40T | 1.1 | 1.4 | 1.1 | 1.3 |
| SEQ ID NO: 1 + T81S | 1.2 | 1.3 | 1.2 | Not tested |
| SEQ ID NO: 1 + Y198F | 1.0 | 1.0 | 1.0 | 1.0 |
| SEQ ID NO: 1 + M208F | 1.0 | 1.0 | 1.0 | 1.1 |
| SEQ ID NO: 1 + H210N | 1.2 | 1.2 | 1.2 | Not tested |
| SEQ ID NO: 1 + V214R | 0.9 | 1.1 | 1.1 | 1.0 |
| SEQ ID NO: 1 + K242P | 0.9 | 0.9 | 1.1 | 1.0 |
| SEQ ID NO: 1 + N260D | 1.4 | 2.0 | 1.1 | 1.5 |
| SEQ ID NO: 1 + M261L | 1.2 | 1.3 | 1.4 | Not tested |
| SEQ ID NO: 1 + Y203G | 0.9 | 1.0 | 0.9 | 1.0 |
| SEQ ID NO: 1 + N174Q + L202M | 0.9 | 0.7 | 1.2 | 1.4 |
| SEQ ID NO: 1 + L202M + Q311R | 0.7 | 0.6 | 1.1 | 1.1 |
| SEQ ID NO: 1 + K37H + L202M | 1.3 | 1.4 | 1.4 | Not tested |
| SEQ ID NO: 1 + K37V + L202M | 0.9 | 0.8 | 1.1 | 1.4 |
| SEQ ID NO: 1 + Q311T | 1.0 | 1.6 | 0.8 | 1.0 |
| SEQ ID NO: 1 + S339A | 1.4 | 1.4 | 1.2 | 2.6 |
| SEQ ID NO: 1 + E360F + S365C | 1.1 | 1.2 | 1.1 | Not tested |
| SEQ ID NO: 1 + S365M | 1.1 | 1.4 | 1.3 | 1.4 |
| SEQ ID NO: 1 + V366I | 1.2 | 1.4 | 1.1 | 1.8 |
| SEQ ID NO: 1 + S384E | 0.9 | 1.1 | 1.0 | 1.0 |
| SEQ ID NO: 1 + Q394K | 0.9 | 1.1 | 1.0 | 0.9 |
| SEQ ID NO: 1 + E416L | 0.7 | 1.2 | 0.9 | 1.1 |
| SEQ ID NO: 1 + A434D | 0.8 | 1.1 | 0.7 | 0.5 |
| SEQ ID NO: 1 + G460E | 1.1 | 1.2 | 1.3 | Not tested |
| SEQ ID NO: 1 + V474C | 1.2 | 1.3 | 1.2 | Not tested |
| SEQ ID NO: 1 + Y198F | 1.0 | 1.4 | 1.2 | 1.3 |
| SEQ ID NO: 1 + K269N | 1.0 | 1.2 | 1.2 | 1.4 |
| SEQ ID NO: 1 + K281H | 0.9 | 1.1 | 1.1 | 1.1 |
| SEQ ID NO: 1 + K108R | 1.2 | 1.3 | 1.5 | Not tested |
| SEQ ID NO: 1 + Y178W | 1.0 | 1.0 | 1.0 | 1.1 |
| SEQ ID NO: 1 + Y243F | 1.2 | 1.3 | 1.3 | Not tested |
| SEQ ID NO: 1 + Y243M | 1.0 | 1.3 | 1.2 | 1.3 |
| SEQ ID NO: 1 + D30N | 1.0 | 1.3 | 1.2 | 1.3 |
| SEQ ID NO: 1 + K37R | 1.1 | 1.6 | 1.1 | 1.4 |
| SEQ ID NO: 1 + Y64W | 0.9 | 1.1 | 1.2 | 1.1 |
| SEQ ID NO: 1 + Y398W | 1.2 | 1.9 | 1.1 | 1.4 |
| SEQ ID NO: 1 + Y404W | 1.2 | 2.6 | 1.0 | 1.8 |
| SEQ ID NO: 1 + R247K | 1.1 | 1.8 | 1.1 | 1.6 |
| SEQ ID NO: 1 + S255K | 1.3 | 2.4 | 1.2 | 1.6 |
| SEQ ID NO: 1 + I257A | 1.2 | 2.3 | 1.2 | 1.5 |
| SEQ ID NO: 1 + F195N | 0.9 | 2.1 | 1.0 | 1.5 |
| SEQ ID NO: 1 + K259N | 1.3 | 1.9 | 1.0 | 1.8 |
| SEQ ID NO: 1 + E276Q | 1.0 | 1.2 | 1.0 | 1.1 |
| SEQ ID NO: 1 + Y299F | 1.3 | 1.8 | 1.2 | 2.0 |
| SEQ ID NO: 1 + Y299W | 1.2 | 2.0 | 1.0 | 1.7 |
| SEQ ID NO: 1 + Q311H | 1.1 | 2.2 | 1.1 | 1.7 |
| SEQ ID NO: 1 + Q319R | 1.2 | 2.0 | 1.1 | 1.7 |
| SEQ ID NO: 1 + Q319H | 1.2 | 1.9 | 1.2 | 1.6 |
| SEQ ID NO: 1 + K320R | 0.9 | 1.2 | 1.0 | 1.1 |
| SEQ ID NO: 1 + K320H | 1.0 | 1.0 | 0.6 | 1.0 |
| SEQ ID NO: 1 + K383Q | 1.0 | 1.2 | 1.1 | 1.1 |
| SEQ ID NO: 1 + K385R | 1.3 | 1.4 | 1.3 | 1.2 |
| SEQ ID NO: 1 + K385Q | 1.2 | 1.2 | 1.0 | 1.1 |
| SEQ ID NO: 1 + K385H | 1.2 | 1.3 | 1.0 | 1.2 |
| SEQ ID NO: 1 + K93R | 1.1 | 1.2 | 1.1 | 1.1 |
| SEQ ID NO: 1 + K93H | 1.2 | 1.2 | 1.1 | 1.2 |
| SEQ ID NO: 1 + Q98R | 1.2 | 1.1 | 1.0 | 1.1 |
| SEQ ID NO: 1 + K118Q | 1.2 | 1.3 | 1.1 | 1.2 |
| SEQ ID NO: 1 + K118H | 1.3 | 1.1 | 1.2 | 1.0 |
| SEQ ID NO: 1 + K118N | 1.1 | 1.3 | 1.1 | 1.2 |

TABLE 9-continued

AMSA wash performance of exemplary polypeptides of the invention

| | ADW Wash conditions | | | |
|---|---|---|---|---|
| | with bleach | | without bleach | |
| Mutations in SEQ ID NO: 1 (amino acid positions relative to SEQ ID NO: 2) | 40° C.-10 min-CS28 | 50° C.-20 min-CS28 | 40° C.-10 min-CS28 | 50° C.-20 min-CS28 |
| SEQ ID NO: 1 + E130H | 1.1 | 1.2 | 1.0 | 1.2 |
| SEQ ID NO: 1 + E130Q | 1.2 | 1.3 | 0.9 | 1.3 |
| SEQ ID NO: 1 + E138Q | 1.2 | 1.4 | 1.0 | 1.3 |
| SEQ ID NO: 1 + K142R | 1.1 | 1.2 | 1.1 | 1.0 |
| SEQ ID NO: 1 + K142Q | 1.1 | 1.1 | 1.0 | 1.1 |
| SEQ ID NO: 1 + K269S + N270G + A274K | 0.9 | 1.1 | 0.7 | 1.2 |
| SEQ ID NO: 1 + W167Y + H210N | 0.9 | 1.1 | 1.0 | 1.0 |
| SEQ ID NO: 1 + W167Y + H210N + S339A | 1.2 | 1.4 | 1.2 | 1.2 |
| SEQ ID NO: 1 + W167Y + H210N + V366I | 1.0 | 1.2 | 0.9 | 1.1 |
| SEQ ID NO: 1 + S339A + V366I | 0.9 | 1.1 | 1.0 | 1.1 |
| SEQ ID NO: 1 + W167Y + V366I | 0.9 | 1.0 | 1.0 | 1.0 |
| SEQ ID NO: 1 + H210N + S339A | 0.9 | 1.3 | 1.1 | 1.1 |
| SEQ ID NO: 1 + H210N + V366I | 1.1 | 1.2 | 1.0 | 1.2 |
| SEQ ID NO: 1 + W167Y + S339A + V366I | 1.1 | 1.2 | 1.0 | 1.2 |
| SEQ ID NO: 1 + W167Y + H210N + S339A + V366I | 1.0 | 1.0 | 1.1 | 1.0 |
| SEQ ID NO: 1 + W167Y + L202M | 1.1 | 0.9 | 1.2 | 1.6 |
| SEQ ID NO: 1 + D30N + N33D + K37V + L202M + K383R | 1.0 | 0.9 | 0.9 | 1.3 |
| SEQ ID NO: 1 + W167Y + L202M + H210N + S339A | 1.0 | 0.9 | 1.3 | 1.3 |
| SEQ ID NO: 1 + W167Y + L202M + H210N + S339A + V366I | 1.0 | 0.8 | 1.2 | 1.2 |
| SEQ ID NO: 1 + W167Y + Y299F | 1.0 | 1.1 | 1.0 | 1.4 |
| SEQ ID NO: 1 + W167Y + H210N + Y299F + S339A | 1.1 | 1.2 | 1.1 | 1.0 |
| SEQ ID NO: 1 + W167Y + H210N + Y299F + S339A + V366I | 1.1 | 1.1 | 1.1 | 1.1 |
| SEQ ID NO: 1 + W48F + W167Y | 1.0 | 1.2 | 1.0 | 1.4 |
| SEQ ID NO: 1 + D30N + N33D + K37V + W48F + K383R | 1.0 | 1.2 | 1.0 | 1.2 |
| SEQ ID NO: 1 + W48F + W167Y + H210N + S339A | 1.2 | 1.3 | 1.2 | 1.2 |
| SEQ ID NO: 1 + W48F + W167Y + H210N + S339A + V366I | 1.3 | 1.7 | 1.3 | 1.3 |
| SEQ ID NO: 1 + M116F + W167Y | 1.0 | 1.1 | 0.9 | 1.1 |
| SEQ ID NO: 1 + D30N + N33D + K37V + M116F + K383R | 1.0 | 1.2 | 0.9 | 1.2 |
| SEQ ID NO: 1 + M116F + W167Y + H210N + S339A | 1.1 | 1.2 | 1.1 | 1.1 |
| SEQ ID NO: 1 + M116F + W167Y + H210N + S339A + V366I | 1.0 | 1.0 | 1.1 | 1.0 |
| SEQ ID NO: 1 + D30N + N33D + K37V + K383R + W482Y | 0.9 | 1.2 | 0.9 | 1.1 |
| SEQ ID NO: 1 + W167Y + H210N + S339A + W482Y | 1.1 | 1.0 | 1.2 | 1.1 |
| SEQ ID NO: 1 + W167Y + H210N + S339A + V366I + W482Y | 1.0 | 1.0 | 1.1 | 1.0 |
| SEQ ID NO: 1 + W167Y + Y243F | 0.9 | 1.0 | 0.9 | 1.1 |
| SEQ ID NO: 1 + W167Y + H210N + Y243F + S339A + V366I | 1.1 | 1.1 | 1.1 | 1.0 |
| SEQ ID NO: 1 + W167Y + L202M + Y299F | 0.9 | 0.8 | 1.0 | 1.3 |
| SEQ ID NO: 1 + W167Y + L202M + H210N + Y299F + S339A | 1.0 | 0.8 | 1.2 | 1.2 |
| SEQ ID NO: 1 + W167Y + L202M + H210N + Y299F + S339A + V366I | 1.0 | 0.7 | 1.2 | 1.2 |
| SEQ ID NO: 1 + W48F + W167Y + L202M | 0.9 | 0.6 | 1.1 | 1.2 |
| SEQ ID NO: 1 + K118H + W167Y + L202M | 0.9 | 0.6 | 1.1 | 1.1 |
| SEQ ID NO: 1 + W48F + W167Y + H210N + Y299F + S339A + V366I | 1.1 | 1.2 | 1.2 | 1.2 |
| SEQ ID NO: 1 + W48F + K118H + W167Y + H210N + S339A | 0.9 | 1.1 | 1.0 | 1.1 |
| SEQ ID NO: 1 + W48F + W167Y + L202M + H210N + S339A | 0.8 | 0.7 | 1.1 | 1.2 |
| SEQ ID NO: 1 + W167Y + H210N + S339A + S365C | 1.2 | 1.6 | 1.2 | 1.3 |
| SEQ ID NO: 1 + W167Y + H210N + S339A + S365C + V366I | 1.2 | 1.6 | 1.2 | 1.3 |
| SEQ ID NO: 1 + W48F + W167Y + H210N + S339A + S365C | 1.2 | 1.6 | 1.1 | 1.3 |

TABLE 9-continued

AMSA wash performance of exemplary polypeptides of the invention

| | ADW Wash conditions | | | |
| --- | --- | --- | --- | --- |
| | with bleach | | without bleach | |
| Mutations in SEQ ID NO: 1 (amino acid positions relative to SEQ ID NO: 2) | 40° C.-10 min-CS28 | 50° C.-20 min-CS28 | 40° C.-10 min-CS28 | 50° C.-20 min-CS28 |
| SEQ ID NO: 1 + W167Y + H210N + Y299F + S339A + S365C + V366I | 1.3 | 1.8 | 1.3 | 1.5 |
| SEQ ID NO: 1 + A51T N54S | 0.9 | 1.1 | 0.9 | 1.0 |
| SEQ ID NO: 1 + S334T | 1.2 | 1.4 | 0.9 | 1.4 |
| SEQ ID NO: 1 + T246M | 1.1 | 1.2 | 1.0 | 1.2 |
| SEQ ID NO: 1 + T246L | 1.1 | 1.2 | 1.0 | 1.2 |
| SEQ ID NO: 1 + T246V | 1.0 | 1.2 | 1.0 | 1.1 |
| SEQ ID NO: 1 + T246I | 1.1 | 1.3 | 1.0 | 1.3 |
| SEQ ID NO: 1 + A186G | 1.0 | 1.3 | 1.0 | 1.3 |
| SEQ ID NO: 1 + A51Q G109M Y203G | 0.9 | 1.1 | 1.1 | 1.2 |
| SEQ ID NO: 1 + V238A S334T | 1.1 | 1.2 | 1.2 | Not tested |
| SEQ ID NO: 1 + A51T L202M | 1.3 | 1.3 | 1.5 | Not tested |
| SEQ ID NO: 1 + L202M T246L | 1.1 | 0.9 | 1.2 | 1.5 |
| SEQ ID NO: 1 + A51T N174Q L202M T246I S334T | 0.9 | 1.0 | 1.3 | 1.8 |
| SEQ ID NO: 1 + A51T N174Q L202M Q311R S334T | 0.9 | 1.2 | 1.1 | Not tested |
| SEQ ID NO: 1 + I235L T246M I250L | 1.2 | 1.4 | 1.2 | Not tested |
| SEQ ID NO: 1 + A186D L202M | 0.9 | 0.7 | 1.1 | 1.2 |
| SEQ ID NO: 1 + A186D L202M N270G N402Y | 0.9 | 1.0 | 1.0 | 1.3 |
| SEQ ID NO: 1 + A186D L202M S339A | 0.8 | 0.8 | 1.1 | 1.3 |
| SEQ ID NO: 1 + A186D F195N L202M | 1.1 | 0.8 | 1.2 | 1.4 |
| SEQ ID NO: 1 + K37H A51T L202M | 1.1 | 0.9 | 1.2 | 1.4 |
| SEQ ID NO: 1 + K37V A51T L202M | 1.2 | 0.9 | 1.2 | 1.5 |
| SEQ ID NO: 1 + A51T L202M S365C | 1.2 | 1.0 | 1.3 | 1.6 |
| SEQ ID NO: 1 + A51T L202M S339A | 1.1 | 1.0 | 1.1 | Not tested |
| SEQ ID NO: 1 + A51T L202M Q311T | 1.2 | 1.0 | 1.2 | 1.5 |
| SEQ ID NO: 1 + A51T L202M M261L | 1.2 | 0.9 | 1.2 | 1.5 |
| SEQ ID NO: 1 + A51T L202M H210N | 1.1 | 0.9 | 1.0 | 1.4 |
| SEQ ID NO: 1 + A51T L202M N270G | 0.9 | 1.1 | 1.1 | 1.4 |
| SEQ ID NO: 1 + A51T F195N L202M | 1.1 | 1.1 | 0.9 | Not tested |
| SEQ ID NO: 1 + A51T L202M Q319H | 1.1 | 0.8 | 1.1 | 1.4 |
| SEQ ID NO: 1 + A51T L202M Q319R | 1.1 | 0.9 | 1.2 | 1.4 |
| SEQ ID NO: 1 + A51T L202M Q311H | 1.1 | 0.9 | 1.2 | 1.5 |
| SEQ ID NO: 1 + A51T L202M R247K | 1.2 | 0.8 | 1.0 | 1.4 |
| SEQ ID NO: 1 + A51T L202M Q311R | 1.0 | 1.0 | 1.0 | 1.3 |
| SEQ ID NO: 1 + A51T L202M Y398W | 1.0 | 1.0 | 1.1 | 1.4 |
| SEQ ID NO: 1 + A51T L202M Y299W | 1.2 | 1.0 | 0.9 | 1.4 |
| SEQ ID NO: 1 + A51T K108R L202M | 1.2 | 1.0 | 1.3 | 1.5 |
| SEQ ID NO: 1 + A51T L202M Y243F | 1.3 | 0.9 | 1.1 | 1.4 |
| SEQ ID NO: 1 + A51T L202M V474C | 1.1 | 0.9 | 1.2 | 1.3 |
| SEQ ID NO: 1 + A51T L202M G460E | 0.9 | 0.7 | 0.9 | 1.2 |
| SEQ ID NO: 1 + N174Q L202M A265G Q311R S334T | 0.9 | 1.0 | 1.1 | 1.3 |
| SEQ ID NO: 1 + A51T L202M T246V A265G Q311R | 0.8 | 0.8 | 0.9 | 1.2 |
| SEQ ID NO: 1 + A51T L202M A265G Q311R | 1.0 | 0.8 | 0.9 | 1.1 |
| SEQ ID NO: 1 + K37H L202M T246V S334T | 0.8 | 1.0 | 1.0 | 1.5 |
| SEQ ID NO: 1 + L202M T246V S334T E416L | 1.0 | 1.2 | 1.0 | 1.6 |
| SEQ ID NO: 1 + L202M T246V S334T N402Y | 1.0 | 1.1 | 1.1 | 1.6 |
| SEQ ID NO: 1 + L202M T246V S334T V366I | 0.9 | 1.1 | 1.0 | 1.4 |
| SEQ ID NO: 1 + L202M T246V S334T S365M | 1.0 | 1.0 | 1.0 | 1.3 |
| SEQ ID NO: 1 + L202M T246V S334T S365C | 1.0 | 1.1 | 1.0 | 1.4 |
| SEQ ID NO: 1 + L202M T246V M261L S334T | 1.0 | 1.0 | 1.0 | 1.2 |
| SEQ ID NO: 1 + D30N L202M H210N T246V S334T | 1.1 | 1.2 | 1.0 | 1.5 |
| SEQ ID NO: 1 + L202M T246V N270G S334T | 0.9 | 1.3 | 0.9 | 1.3 |
| SEQ ID NO: 1 + F195N L202M T246V S334T | 1.0 | 1.3 | 1.0 | 1.4 |
| SEQ ID NO: 1 + L202M T246V Q319H S334T | 1.0 | 1.1 | 1.0 | 1.4 |
| SEQ ID NO: 1 + L202M T246V Q319R S334T | 0.9 | 1.1 | 1.0 | 1.3 |
| SEQ ID NO: 1 + L202M T246V Q311H S334T | 1.0 | 1.1 | 0.9 | 1.4 |
| SEQ ID NO: 1 + L202M T246V Q311R S334T | 1.1 | 1.0 | 1.0 | 1.4 |
| SEQ ID NO: 1 + L202M T246V S334T Y398W | 1.0 | 1.1 | 0.9 | 1.3 |
| SEQ ID NO: 1 + L202M T246V K320H S334T | 1.0 | 1.0 | 1.0 | 1.5 |
| SEQ ID NO: 1 + L202M T246V Y299W S334T | 1.1 | 1.0 | 0.9 | 1.3 |
| SEQ ID NO: 1 + L202M T246V K320R S334T | 1.1 | 1.2 | 1.0 | 1.3 |
| SEQ ID NO: 1 + L202M Y243F S334T | 0.9 | 1.2 | 1.1 | 1.4 |
| SEQ ID NO: 1 + L202M T246V S334T V474C | 0.8 | 0.9 | 0.8 | 1.2 |
| SEQ ID NO: 1 + L202M T246V S334T G460E | 0.7 | 0.9 | 0.8 | 1.2 |
| SEQ ID NO: 1 + L202M I235M T246V S334T | 0.8 | 0.9 | 0.9 | 1.3 |

TABLE 9-continued

AMSA wash performance of exemplary polypeptides of the invention

| | ADW Wash conditions | | | |
|---|---|---|---|---|
| | with bleach | | without bleach | |
| Mutations in SEQ ID NO: 1 (amino acid positions relative to SEQ ID NO: 2) | 40° C.- 10 min- CS28 | 50° C.- 20 min- CS28 | 40° C.- 10 min- CS28 | 50° C.- 20 min- CS28 |
| SEQ ID NO: 1 + K108R L202M T246V S334T | 1.0 | 1.1 | 0.8 | 1.3 |
| SEQ ID NO: 1 + A51T A186D L202M N270G N402Y | 0.8 | 1.2 | 1.0 | 1.4 |
| SEQ ID NO: 1 + A186D L202M N270G S339A N402Y | 0.9 | 1.3 | 1.0 | 1.4 |
| SEQ ID NO: 1 + A51T A186D L202M N270G | 1.2 | 2.0 | 1.4 | 3.0 |
| SEQ ID NO: 1 + A51T L202M T246V N270G | 0.9 | 1.7 | 1.1 | 2.7 |
| SEQ ID NO: 1 + K37H A51T L202M N270G | 0.8 | 1.5 | 1.2 | 2.1 |
| SEQ ID NO: 1 + A51T L202M T246L N270G | 1.0 | 1.7 | 1.1 | 2.6 |
| SEQ ID NO: 1 + A51T N174Q L202M N270G | 0.8 | 1.6 | 1.1 | 2.4 |
| SEQ ID NO: 1 + A51T L202M V238A N270G | 0.9 | 1.4 | 1.0 | 2.8 |
| SEQ ID NO: 1 + A51T L202M A265G | 1.1 | 1.6 | 1.4 | 2.7 |
| SEQ ID NO: 1 + A51T L202M M261L N270G | 1.0 | 1.4 | 1.3 | 2.6 |
| SEQ ID NO: 1 + A51T L202M F267Y | 1.1 | 1.4 | 1.2 | 2.8 |
| SEQ ID NO: 1 + A51T L202M I275L | 1.1 | 1.1 | 1.3 | 2.2 |
| SEQ ID NO: 1 + A51T L202M N270G S365M | 0.6 | 0.6 | 0.8 | 1.3 |
| SEQ ID NO: 1 + A51T L202M N270G S365C | 1.2 | 1.9 | 1.2 | 2.7 |
| SEQ ID NO: 1 + A51T L202M N270G Q311T | 0.7 | 1.1 | 0.8 | 1.3 |
| SEQ ID NO: 1 + A51T L202M N270G E416L | 0.6 | 1.0 | 0.7 | 1.2 |
| SEQ ID NO: 1 + A51T L202M N270G N402Y | 0.7 | 1.0 | 0.8 | 1.2 |
| SEQ ID NO: 1 + A51T L202M N270G S365C | 0.7 | 1.2 | 0.9 | 1.3 |
| SEQ ID NO: 1 + A51T L202M N270G K383R | 0.8 | 1.2 | 0.9 | 1.3 |
| SEQ ID NO: 1 + A51T L202M N270G V474C | 0.8 | 1.1 | 0.9 | 1.4 |
| SEQ ID NO: 1 + A51T L202M N270G G460E | 0.8 | 1.1 | 1.0 | 1.4 |
| SEQ ID NO: 1 + A51T Q86L L202M N270G | 0.7 | 0.8 | 0.9 | 1.3 |
| SEQ ID NO: 1 + A51T Q86I L202M N270G | 0.8 | 1.2 | 1.0 | 1.5 |
| SEQ ID NO: 1 + A51T A113E L202M N270G | 0.7 | 1.1 | 0.8 | 1.3 |
| SEQ ID NO: 1 + A51T K93H L202M N270G | 0.8 | 1.3 | 0.9 | 1.3 |
| SEQ ID NO: 1 + A51T K108R L202M N270G | 0.8 | 1.3 | 0.9 | 1.3 |
| SEQ ID NO: 1 + A51T L202M K269N | 0.9 | 1.0 | 1.1 | 1.2 |
| SEQ ID NO: 1 + A51T L202M Y243F N270G | 0.9 | 1.0 | 1.0 | 1.2 |
| SEQ ID NO: 1 + A51T F195N L202M N270G | 0.6 | 0.9 | 0.7 | 1.1 |
| SEQ ID NO: 1 + A51T L202M R247K N270G | 0.8 | 1.0 | 0.8 | 1.2 |
| SEQ ID NO: 1 + A51T L202M R218N N270G | 0.7 | 1.0 | 0.9 | 1.3 |
| SEQ ID NO: 1 + A51T L202M S255K N270G | 0.8 | 1.1 | 0.9 | 1.3 |
| SEQ ID NO: 1 + A51T L202M I257A N270G | 0.7 | 1.1 | 0.9 | 1.2 |
| SEQ ID NO: 1 + A51T L202M V214I R218N N270G | 0.8 | 1.1 | 0.9 | 1.3 |
| SEQ ID NO: 1 + A51T L202M N270G Q311H | 0.8 | 1.1 | 0.9 | 1.3 |
| SEQ ID NO: 1 + A51T L202M N270G K320H | 0.7 | 1.2 | 0.9 | 1.3 |
| SEQ ID NO: 1 + A51T L202M N270G Y299W | 0.8 | 1.1 | 0.8 | 1.3 |
| SEQ ID NO: 1 + A51T L202M N270G K320R | 0.7 | 1.1 | 0.9 | 1.4 |
| SEQ ID NO: 1 + A51T L202M N270G K383Q | 0.8 | 1.2 | 0.9 | 1.3 |
| SEQ ID NO: 1 + A51T K142R L202M N270G | 0.9 | 1.3 | 1.0 | 1.4 |
| SEQ ID NO: 1 + A51T E130Q L202M N270G | 0.8 | 1.2 | 0.9 | 1.4 |
| SEQ ID NO: 1 + A51T K118N L202M N270G | 0.8 | 1.0 | 0.8 | 1.2 |
| SEQ ID NO: 1 + A51T E138Q L202M N270G | 0.8 | 1.3 | 0.9 | 1.4 |
| SEQ ID NO: 1 + A51T K118H L202M N270G | 0.8 | 1.1 | 0.9 | 1.2 |
| SEQ ID NO: 1 + A51T K118Q L202M N270G | 0.6 | 0.8 | 0.7 | 1.0 |
| SEQ ID NO: 1 + A51T Q86H L202M N270G | 0.5 | 0.8 | 0.7 | 1.0 |
| SEQ ID NO: 1 + A51T E121H L202M N270G | 0.8 | 1.1 | 0.9 | 1.3 |
| SEQ ID NO: 1 + A51T K118R L202M N270G | 0.6 | 0.8 | 0.7 | 1.1 |
| SEQ ID NO: 1 + K37H A51T N174Q L202M A265G Q311R S334T | 1.0 | 1.0 | 1.1 | 1.3 |
| SEQ ID NO: 1 + A51T N174Q L202M T246I Q311R S334T | 0.8 | 0.9 | 0.9 | 1.2 |
| SEQ ID NO: 1 + K37V A51T L202M A265G F267Y Q311R S334T | 0.9 | 1.1 | 1.0 | 1.2 |
| SEQ ID NO: 1 + A51T N174Q L202M A265G F267Y Q311R S334T | 0.8 | 0.9 | 1.0 | 1.2 |
| SEQ ID NO: 1 + A51G L202M Q311R S334T | 0.8 | 0.7 | 0.9 | 1.1 |
| SEQ ID NO: 1 + L202M T246I A265G F267Y Q311R S334T | 0.8 | 0.8 | 0.9 | 1.2 |
| SEQ ID NO: 1 + A51T L202M F267Y Q311R S334T S365L | 0.8 | 0.9 | 1.0 | 1.2 |
| SEQ ID NO: 1 + A51T L202M S365C | 0.9 | 1.2 | 0.9 | 1.3 |
| SEQ ID NO: 1 + A51T K108R L202M | 0.8 | 0.8 | 0.8 | 1.2 |
| SEQ ID NO: 1 + A51T S365C | 0.9 | 1.4 | 0.9 | 1.1 |
| SEQ ID NO: 1 + A51T K108R | 0.8 | 1.1 | 0.9 | 0.9 |
| SEQ ID NO: 1 + L202M V238A S334T | 0.9 | 1.1 | 1.0 | 1.5 |

TABLE 9-continued

AMSA wash performance of exemplary polypeptides of the invention

| | ADW Wash conditions | | | |
|---|---|---|---|---|
| | with bleach | | without bleach | |
| Mutations in SEQ ID NO: 1 (amino acid positions relative to SEQ ID NO: 2) | 40° C.-10 min-CS28 | 50° C.-20 min-CS28 | 40° C.-10 min-CS28 | 50° C.-20 min-CS28 |
| SEQ ID NO: 1 + W48F V238A S334T | 1.0 | 1.6 | 1.1 | 1.5 |
| SEQ ID NO: 1 + M116F V238A S334T | 1.0 | 1.4 | 1.0 | 1.5 |
| SEQ ID NO: 1 + V238A S334T W482Y | 1.0 | 1.5 | 0.9 | 1.4 |
| SEQ ID NO: 1 + Y243F S334T | 0.9 | 1.4 | 1.0 | 1.3 |
| SEQ ID NO: 1 + L202M V238A Y299F S334T | 1.0 | 1.1 | 1.0 | 1.2 |
| SEQ ID NO: 1 + L202M T246V N270G S334T | 0.7 | 1.1 | 0.8 | 1.2 |
| SEQ ID NO: 1 + W48F K118H V238A S334T | 1.0 | 1.3 | 1.0 | 1.2 |
| SEQ ID NO: 1 + W48F L202M V238A S334T | 0.9 | 1.0 | 1.0 | 1.3 |
| SEQ ID NO: 1 + A51T A186N L202M N270G S365C | 0.9 | 1.3 | 0.9 | 1.3 |
| SEQ ID NO: 1 + W167Y A186N H210N S339A V366I | 1.2 | 1.5 | 1.2 | 1.2 |
| SEQ ID NO: 1 + W48F W167Y A186N H210N S339A | 1.2 | 1.6 | 1.2 | 1.4 |
| SEQ ID NO: 1 + W167Y A186N H210N Y299F S339A V366I | 1.3 | 1.6 | 1.2 | 1.4 |
| SEQ ID NO: 1 + L202M T246V N270G S334T S365C | 1.0 | 1.5 | 1.0 | 1.3 |
| SEQ ID NO: 1 + A186N L202M T246V N270G S334T | 0.8 | 1.3 | 0.9 | 1.2 |
| SEQ ID NO: 1 + A51T | 1.0 | 1.3 | 1.1 | 1.3 |

The invention claimed is:

1. A polypeptide comprising a variant amino acid sequence of SEQ ID NO: 1, wherein the polypeptide comprises:
   (a) a substitution with Y or H at a position corresponding to amino acid position 167, wherein numbering is according to the amino acid sequence set forth in SEQ ID NO: 2; and
   (b) a mutation at one or more positions corresponding to positions 48, 210, 299, 339, or 366, wherein numbering is according to the amino acid sequence set forth in SEQ ID NO: 2;
   wherein the polypeptide has at least 90% sequence identity to the amino acid sequence set forth in SEQ ID NO: 1, and wherein the polypeptide has alpha-amylase activity and exhibits an enhanced wash performance compared to the polypeptide of SEQ ID NO: 1.

2. The polypeptide of claim 1 wherein the enhanced wash performance is assessed using an Automatic Mechanical Stress Assay (AMSA) assay.

3. The polypeptide of claim 1 wherein the enhanced wash performance is exhibited during high temperature washes.

4. The polypeptide of claim 3, wherein said high temperature is at least 40° C.

5. The polypeptide of claim 2, wherein said polypeptide exhibits an enhanced wash performance in one or more of the conditions selected from the group consisting of:
   (a) Model ADW detergent with bleach at 40° C. and a wash cycle of 10 min;
   (b) Model ADW detergent without bleach at 40° C. and a wash cycle of 10 min;
   (c) Model ADW detergent with bleach at 50° C. and a wash cycle of 20 min; and
   (d) Model ADW detergent without bleach at 50° C. and a wash cycle of 20 min;
   wherein said model ADW detergent comprises trisodium salt of methylglycinediacetic acid, sodium citrate, sodium carbonate, sodium silicate, sodium sulphate, polyphosphate and silicate scale inhibitor.

6. The polypeptide of claim 1 wherein the polypeptide is 1000 or fewer amino acids in length.

7. The polypeptide of claim 6 wherein the polypeptide is between 400 and 600 amino acids in length.

8. The polypeptide of claim 1 further comprising a mutation at one or more positions corresponding to positions 10, 25, 30, 37, 40, 51, 54, 64, 81, 86, 93, 98, 105, 108, 109, 113, 116, 118, 121, 130, 135, 138, 142, 174, 175, 178, 182, 186, 187, 189, 195, 198, 202, 203, 206, 208, 214, 218, 235, 238, 242, 243, 246, 247, 250, 255, 257, 259, 260, 261, 265, 267, 269, 270, 274, 275, 276, 281, 295, 298, 311, 319, 320, 334, 360, 365, 383, 384, 385, 394, 398, 402, 404, 416, 434, 460, 469, 474, and 482, wherein numbering is according to the amino acid sequence set forth in SEQ ID NO: 2.

9. The polypeptide of claim 8, wherein said mutation at one or more positions is a substitution, deletion, and/or insertion.

10. The polypeptide of claim 1, wherein said polypeptide further comprises one or more of the following substitutions relative to the amino acid sequence of SEQ ID NO:2: M10L, N25K, D30N, K37H, K37L, K37M, K37R, K37V, S40T, A51Q, A51T, N54S, Y64W, T81S, Q86H, Q86I, Q86L, K93H, K93R, Q98R, M105Y, M105F, M105I, M105L, K108R, G109A, G109M, A113E, M116I, M116L, M116A, M116V, M116F, K118Q, K118H, K118N, K118R, E121H, E130H, E130Q, Y135H, E138Q, K142R, K142Q, N174Q, N174*, N175Q, Y178W, T182G, A186D, A186G, W187Y, W189H, F195N, Y198F, Y203H, Y203N, Y203G, Y203F, I206L, M208F, M208L, M208V, V214R, V214T, V214I, R218N, I235V, I235L, I235M, V238T, V238A, K242P, Y243F, Y243M, T246V, T246I, T246L, T246M, R247K, I250L, I250V, S255K, I257A, K259N, N260D, M261L, M261A, A265G, F267Y, K269S, K269N, N270G, A274K, I275L, E276Q, K281H, F295Y, F295W, Y298W, Y298F, Q311T, Q311H, Q311R, Q319H, Q319R, K320H, K320R, S334T, E360F, S365M, S365C, K383Q, K383R, S384E, K385H, K385Q, K385R, Q394K, Y398W, N402Y, Y404W, E416L, A434D, G460E, W469F, V474C, and W482Y, wherein numbering is according to the amino acid sequence set forth in SEQ ID NO: 2.

11. The polypeptide of claim 1, wherein said polypeptide consists of the amino acid sequence of SEQ ID NO:2 with mutations selected from the group consisting of:
W167Y+H210N+V366I, W167Y+H210N, W167Y+H210N+Y243F+V366I, W167Y+H210N+V366I+W482Y, M116F+W167Y+H210N+V366I, W48F+W167Y+H210N+V366I, W167Y+L202M+H210N+V366I, W167Y+H210N+W482Y, M116F+W167Y+H210N, W48F+W167Y+H210N, W167Y+L202M+H210N, W48F+W167Y, W167Y+V366I, wherein numbering is according to the amino acid sequence set forth in SEQ ID NO: 2.

12. The polypeptide of claim 1, wherein said enhanced wash performance corresponds to an Improvement Factor (IF) of at least 1.2 when the polypeptide is evaluated in an ADW assay with a detergent comprising bleach and at 40° C. for 10 min.

13. The polypeptide of claim 12, wherein said polypeptide comprises a mutation at one or more positions corresponding to positions 37, 51, 93, 98, 108, 118, 186, 202, 210, 235, 243, 246, 247, 250, 255, 259, 260, 261, 270, 299, 311, 319, 334, 339, 365, 385, 398, and 404, wherein numbering is according to the amino acid sequence set forth in SEQ ID NO: 2.

14. The polypeptide of claim 1, wherein said enhanced wash performance corresponds to an IF of at least 1.2 when the polypeptide is evaluated in an ADW assay with a detergent comprising bleach and at 50° C. for 20 min.

15. The polypeptide of claim 14, wherein said polypeptide further comprises a mutation at one or more positions corresponding to positions 30, 33, 37, 40, 51, 81, 86, 93, 105, 108, 116, 118, 130, 138, 142, 174, 175, 182, 186, 195, 198, 202, 206, 235, 238, 243, 246, 247, 250, 255, 257, 259, 260, 261, 265, 266, 267, 269, 270, 311, 319, 320, 334, 360, 365, 383, 385, 402, 416, 474, and 482, wherein numbering is according to the amino acid sequence set forth in SEQ ID NO: 2.

16. The polypeptide of claim 14, wherein said polypeptide consists of the amino acid sequence of SEQ ID NO: 2 with mutations selected from the group consisting of:
W167Y+H210N, W48F+W167Y+H210N, W48F+W167Y, and W167Y+H210N+V366I, wherein numbering is according to the amino acid sequence set forth in SEQ ID NO: 2.

17. The polypeptide of claim 1, wherein said enhanced wash performance corresponds to an Improvement Factor (IF) of at least 1.2 when the polypeptide is evaluated in an ADW assay with a detergent without bleach and at 40° C. for 10 min.

18. The polypeptide of claim 17, wherein said polypeptide further comprises a mutation at one or more positions corresponding to positions 37, 51, 64, 81, 108, 116, 174, 186, 187, 189, 195, 198, 202, 208, 235, 238, 243, 246, 250, 261, 265, 267, 269, 270, 275, 311, 319, 334, 365, 385, 460, and 474, wherein numbering is according to the amino acid sequence set forth in SEQ ID NO: 2.

19. The polypeptide of claim 17, wherein said polypeptide consists of the amino acid sequence of SEQ ID NO: 2 with the mutations W167Y+H210N, wherein numbering is according to the amino acid sequence set forth in SEQ ID NO: 2.

20. The polypeptide of claim 1, wherein said enhanced wash performance corresponds to an IF of at least 1.2 when the polypeptide is evaluated in an ADW assay with a detergent without bleach and at 50° C. for 20 min.

21. The polypeptide of claim 20, wherein said polypeptide further comprises a mutation at one or more positions corresponding to positions 30, 33, 37, 40, 51, 86, 93, 108, 109, 113, 116, 118, 121, 130, 138, 142, 174, 175, 182, 186, 195, 198, 202, 203, 218, 235, 238, 243, 246, 247, 250, 255, 257, 259, 260, 261, 265, 267, 269, 270, 274, 275, 311, 319, 320, 334, 365, 383, 385, 398, 402, 416, 404, 460, 474, and 482, wherein numbering is according to the amino acid sequence set forth in SEQ ID NO: 2.

22. The polypeptide of claim 20, wherein said polypeptide consists of the amino acid sequence of SEQ ID NO:2 with the mutations W167Y+H210N+V366I, and W167Y, wherein numbering is according to the amino acid sequence set forth in SEQ ID NO: 2.

23. The polypeptide of claim 1, wherein said polypeptide consists of the amino acid sequence of SEQ ID NO:2 with a W167Y mutation and a mutation at one or more positions corresponding to positions 48, 210, 299, 339, or 366, wherein numbering is according to the amino acid sequence set forth in SEQ ID NO: 2.

24. The polypeptide of claim 1, wherein said polypeptide comprises or consists of an amino acid sequence selected from the following:
(a) SEQ ID NO: 1 with mutations W167Y, H210N and S339A;
(b) SEQ ID NO: 1 with mutations W167Y, H210N, S339A and V366I;
(c) SEQ ID NO: 1 with mutations W167Y, H210N, Y299F, S339A and V366I;
(d) SEQ ID NO: 1 with mutations W48F and W167Y;
(e) SEQ ID NO: 1 with mutations W48F, W167Y, H210N and S339A;
(f) SEQ ID NO: 1 with mutations W48F, W167Y, H210N, Y299F, S339A and V366I; and
wherein numbering is according to the amino acid sequence set forth in SEQ ID NO: 2.

25. The polypeptide of claim 1, wherein said polypeptide comprises or consists of an amino acid sequence which shares at least 97%-sequence identity to SEQ ID NO: 1.

26. The polypeptide of claim 1, wherein the number of mutations relative to SEQ ID NO:1 is 1-20 mutations.

27. The polypeptide of claim 1, wherein said polypeptide is selected from:
SEQ ID NO:1+W167Y+H210N+S339A+V366I;
SEQ ID NO:1+W167Y+H210N+S339A;
SEQ ID NO:1+W167Y+H210N;
SEQ ID NO:1+W167Y+L202M+H210N+Y299F+S339A+V366I;
SEQ ID NO:1+W167Y+H210N+Y243F+S339A+V366I;
SEQ ID NO:1+W167Y+H210N+S339A+V366I+W482Y;
SEQ ID NO:1+M116F+W167Y+H210N+S339A+V366I;
SEQ ID NO:1+W48F+W167Y+H210N+S339A+V366I;
SEQ ID NO:1+W167Y+H210N+Y299F+S339A+V366I;

SEQ ID NO:1+W167Y+L202M+H210N+S339A+ V366I;
SEQ ID NO:1+W167Y+L202M+H210N+Y299F+ S339A;
SEQ ID NO:1+W167Y+H210N+S339A+W482Y;
SEQ ID NO:1+M116F+W167Y+H210N+S339A;
SEQ ID NO:1+W48F+W167Y+H210N+S339A;
SEQ ID NO:1+W167Y+H210N+Y299F+S339A;
SEQ ID NO:1+W167Y+L202M+H210N+S339A;
SEQ ID NO:1+W167Y+L202M+Y299F;
SEQ ID NO:1+W48F+W167Y;
SEQ ID NO:1+W167Y+Y299F;
SEQ ID NO:1+W167Y+H210N+V366I;
SEQ ID NO:1+W167Y+V366I; and
SEQ ID NO:1+W167Y+S339A+V366I wherein numbering is according to the amino acid sequence set forth in SEQ ID NO: 2.

28. A polynucleotide encoding said polypeptide of claim 1.

29. A nucleic acid construct comprising said polynucleotide of claim 28.

30. An expression vector comprising said polynucleotide of claim 28.

31. A host cell comprising said polynucleotide of claim 28.

32. A method of producing an alpha-amylase polypeptide, comprising:
(a) cultivating a host cell under conditions suitable for expression of said polypeptide, wherein said host cell comprises a polynucleotide encoding a polypeptide comprising a variant amino acid sequence of SEQ ID NO: 1, wherein the polypeptide comprises a substitution with Y or H at a position corresponding to amino acid position 167 of SEQ ID NO: 2 and a mutation at one or more positions corresponding to positions 48, 210, 299, 339, 366, wherein numbering is according to the amino acid sequence set forth in SEQ ID NO: 2, wherein the polypeptide has at least 90% sequence identity to the amino acid sequence set forth in SEQ ID NO: 1, and wherein the variant polypeptide has alpha-amylase activity and exhibits an enhanced wash performance compared to the polypeptide of SEQ ID NO: 1; and
(b) recovering said polypeptide.

33. The method of claim 32, wherein said polypeptide further comprises a mutation at one or more positions corresponding to positions 10, 25, 30, 37, 40, 51, 54, 64, 81, 86, 93, 98, 105, 108, 109, 113, 116, 118, 121, 130, 135, 138, 142, 174, 175, 178, 182, 186, 187, 189, 195, 198, 202, 203, 206, 208, 214, 218, 235, 238, 242, 243, 246, 247, 250, 255, 257, 259, 260, 261, 265, 267, 269, 270, 274, 275, 276, 281, 295, 298, 311, 319, 320, 334, 360, 365, 383, 384, 385, 394, 398, 402, 404, 416, 434, 460, 469, 474, and 482, wherein numbering is according to the amino acid sequence set forth in SEQ ID NO: 2.

34. A detergent composition, comprising the polypeptide of claim 1 and a concentrate or additive for making the same.

35. The composition of claim 34 wherein the surfactant is selected from the group consisting of anionic surfactants, cationic surfactants, nonionic surfactants and amphoteric surfactants.

36. The composition of claim 34 further comprising one or more additional components selected from the group consisting of oxidizing agents, bleach activators, chelating agents, bulking agents, builders, buffering agents, structurants, sequestrants, optical brighteners, antifoaming agents, enzymes, fragrances, anti-redeposition agents, skin conditioning agents, softness extenders, emulsifiers, and colorants.

37. The composition of claim 34, wherein said composition is a liquid or powder laundry detergent composition.

38. The composition of claim 34, wherein said composition is a liquid or powder automatic dishwashing (ADW) detergent composition.

39. The composition of claim 34, wherein said composition is a liquid manual dishwashing detergent composition.

40. The polypeptide of claim 1, wherein the variant amino acid sequence comprises a W167Y substitution at amino acid position 167.

41. The polypeptide of claim 1, wherein the variant amino acid sequence comprises a W167H substitution at amino acid position 167.

42. The polypeptide of claim 1, wherein said polypeptide comprises one or more of the following substitutions relative to the amino acid sequence of SEQ ID NO:2: W48F, H210N, and V366I, wherein numbering is according to the amino acid sequence set forth in SEQ ID NO: 2.

* * * * *

UNITED STATES PATENT AND TRADEMARK OFFICE
CERTIFICATE OF CORRECTION

PATENT NO. : 11,407,986 B2
APPLICATION NO. : 16/062492
DATED : August 9, 2022
INVENTOR(S) : Regueira et al.

It is certified that error appears in the above-identified patent and that said Letters Patent is hereby corrected as shown below:

In the Claims

Please amend Claim 10 at Column 94, Line 58 – Column 95, Line 13 as follows:
10. The polypeptide of claim 1, wherein said polypeptide further comprises one or more of the following substitutions relative to the amino acid sequence of SEQ ID NO: 2: M10L, N25K, D30N, K37H, K37L, K37M, K37R, K37V, S40T, A51Q, A51T, N54S, Y64W, T81S, Q86H, Q86I, Q86L, K93H, K93R, Q98R, M105Y, M105F, M105I, M105L, K108R, G109A, G109M, A113E, M116I, M116L, M116A, M116V, M116F, K118Q, K118H, K118N, K118R, E121H, E130H, E130Q, Y135H, E138Q, K142R, K142Q, N174Q, N174*, N175Q, Y178W, T182G, A186D, A186G, W187Y, W189H, F195N, Y198F, Y203H, Y203N, Y203G, Y203F, I206L, M208F, M208L, M208V, V214R, V214T, V214I, R218N, I235V, I235L, I235M, V238T, V238A, K242P, Y243F, Y243M, T246V, T246I, T246L, T246M, R247K, I250L, I250V, S255K, I257A, K259N, N260D, M261L, M261A, A265G, F267Y, K269S, K269N, N270G, A274K, I275L, E276Q, K281H, F295Y, F295W, Y298W, Y298F, Q311T, Q311H, Q311R, Q319H, Q319R, K320H, K320R, S334T, E360F, S365M, S365C, K383Q, K383R, S384E, K385H, K385Q, K385R, Q394K, Y398W, N402Y, Y404W, E416L, A434D, G460E, W469F, V474C, and W482Y, wherein numbering is according to the amino acid sequence set forth in SEQ ID NO: 2.

Please amend Claim 11 at Column 95, Lines 14-25 as follows:
11. The polypeptide of claim 1, wherein said polypeptide consists of the amino acid sequence of SEQ ID NO: 2 with mutations selected from the group consisting of: W167Y+H210N+V366I, W167Y+H210N, W167Y+H210N+Y243F+V366I, W167Y+H210N+V366I+W482Y, M116F+W167Y+H210N+V366I, W48F+W167Y+H210N+V366I, W167Y+L202M+H210N+V366I, W167Y+H210N+W482Y, M116F+W167Y+H210N, W48F+W167Y+H210N, W167Y+L202M+H210N, W48F+W167Y, W167Y+V366I, wherein numbering is according to the amino acid sequence set forth in SEQ ID NO: 2.

Please amend Claim 16 at Column 95, Lines 51-57 as follows:
16. The polypeptide of claim 14, wherein said polypeptide consists of the amino acid sequence of Signed and Sealed this
Fourth Day of April, 2023

Katherine Kelly Vidal
*Director of the United States Patent and Trademark Office*

SEQ ID NO: 2 with mutations selected from the group consisting of: W167Y+H210N, W48F+W167Y+H210N, W48F+W167Y, and W167Y+H210N+V366I, wherein numbering is according to the amino acid sequence set forth in SEQ ID NO: 2.

SEQUENCE LISTING

<160> NUMBER OF SEQ ID NOS: 15

<210> SEQ ID NO 1
<211> LENGTH: 483
<212> TYPE: PRT
<213> ORGANISM: Bacillus sp.

<400> SEQUENCE: 1

```
His His Asn Gly Thr Asn Gly Thr Leu Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Ser Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Ile Arg Thr Lys Tyr Gly
65                  70                  75                  80

Thr Arg Asn Gln Leu Gln Ala Ala Val Asn Ala Leu Lys Ser Asn Gly
                85                  90                  95

Ile Gln Val Tyr Gly Asp Val Val Met Asn His Lys Gly Gly Ala Asp
            100                 105                 110

Ala Thr Glu Met Val Lys Ala Val Glu Val Asn Pro Asn Asn Arg Asn
        115                 120                 125

Gln Glu Val Ser Gly Glu Tyr Thr Ile Glu Ala Trp Thr Lys Phe Asp
    130                 135                 140

Phe Pro Gly Arg Ala Asn Thr His Ser Asn Phe Lys Trp Arg Trp Tyr
145                 150                 155                 160

His Phe Asp Gly Val Asp Trp Asp Gln Ser Arg Lys Leu Asn Asn Arg
                165                 170                 175
```

```
Ile Tyr Lys Phe Arg Thr Lys Ala Trp Asp Trp Glu Val Asp Thr Glu
            180                 185                 190

Phe Gly Asn Tyr Asp Tyr Leu Leu Tyr Ala Asp Ile Asp Met Asp His
        195                 200                 205

Pro Glu Val Val Asn Glu Leu Arg Asn Trp Gly Val Trp Tyr Thr Asn
    210                 215                 220

Thr Leu Gly Leu Asp Gly Phe Arg Ile Asp Ala Val Lys His Ile Lys
225                 230                 235                 240

Tyr Ser Phe Thr Arg Asp Trp Ile Asn His Val Arg Ser Ala Ile Gly
                245                 250                 255

Lys Asn Met Phe Ala Val Ala Glu Phe Trp Lys Asn Asp Leu Gly Ala
            260                 265                 270

Ile Glu Asn Tyr Leu Asn Lys Thr Asn Trp Asn His Ser Val Phe Asp
        275                 280                 285

Val Pro Leu His Phe Asn Leu Tyr Tyr Ala Ser Lys Ser Gly Gly Asn
    290                 295                 300

Tyr Asp Met Arg Gln Ile Phe Asn Gly Thr Val Val Gln Lys His Pro
305                 310                 315                 320

Thr His Ala Val Thr Phe Val Asp Asn His Asp Ser Gln Pro Glu Glu
                325                 330                 335

Ser Leu Glu Ser Phe Val Arg Glu Trp Phe Lys Pro Leu Ala Tyr Ala
            340                 345                 350

Leu Thr Leu Thr Arg Glu Gln Gly Tyr Pro Ser Val Phe Tyr Gly Asp
        355                 360                 365

Tyr Tyr Gly Ile Pro Thr His Gly Val Pro Ala Met Lys Ser Lys Ile
    370                 375                 380

Asp Pro Ile Leu Glu Ala Arg Gln Lys Tyr Ala Tyr Gly Arg Gln Asn
385                 390                 395                 400

Asp Tyr Leu Asp His His Asn Ile Ile Gly Trp Thr Arg Glu Gly Asn
                405                 410                 415

Thr Ala His Pro Asn Ser Gly Leu Ala Thr Ile Met Ser Asp Gly Ala
            420                 425                 430

Gly Gly Asn Lys Trp Met Phe Val Gly Arg Asn Lys Ala Gly Gln Val
        435                 440                 445

Trp Thr Asp Ile Thr Gly Asn Lys Ala Gly Thr Val Thr Ile Asn Ala
    450                 455                 460

Asp Gly Trp Gly Asn Phe Ser Val Asn Gly Gly Ser Val Ser Ile Trp
465                 470                 475                 480

Val Asn Lys

<210> SEQ ID NO 2
<211> LENGTH: 485
<212> TYPE: PRT
<213> ORGANISM: Bacillus subtilis

<400> SEQUENCE: 2

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Ser Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60
```

```
Asp Leu Gly Glu Phe Asn Gln Lys Gly Thr Ile Arg Thr Lys Tyr Gly
 65                  70                  75                  80

Thr Arg Asn Gln Leu Gln Ala Ala Val Asn Ala Leu Lys Ser Asn Gly
                 85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
        115                 120                 125

Gln Glu Val Ser Gly Glu Tyr Thr Ile Glu Ala Trp Thr Lys Phe Asp
    130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Lys Leu Asn Asn Arg
                165                 170                 175

Ile Tyr Lys Phe Arg Gly Asp Gly Lys Gly Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
    210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                245                 250                 255

Thr Gly Lys Asn Met Phe Ala Val Ala Glu Phe Trp Lys Asn Asp Leu
            260                 265                 270

Gly Ala Ile Glu Asn Tyr Leu Asn Lys Thr Asn Trp Asn His Ser Val
        275                 280                 285

Phe Asp Val Pro Leu His Tyr Asn Leu Tyr Asn Ala Ser Lys Ser Gly
    290                 295                 300

Gly Asn Tyr Asp Met Arg Gln Ile Phe Asn Gly Thr Val Val Gln Arg
305                 310                 315                 320

His Pro Met His Ala Val Thr Phe Val Asp Asn His Asp Ser Gln Pro
                325                 330                 335

Glu Glu Ala Leu Glu Ser Phe Val Glu Glu Trp Phe Lys Pro Leu Ala
            340                 345                 350

Tyr Ala Leu Thr Leu Thr Arg Glu Gln Gly Tyr Pro Ser Val Phe Tyr
        355                 360                 365

Gly Asp Tyr Tyr Gly Ile Pro Thr His Gly Val Pro Ala Met Lys Ser
    370                 375                 380

Lys Ile Asp Pro Ile Leu Glu Ala Arg Gln Lys Tyr Ala Tyr Gly Arg
385                 390                 395                 400

Gln Asn Asp Tyr Leu Asp His His Asn Ile Ile Gly Trp Thr Arg Glu
                405                 410                 415

Gly Asn Thr Ala His Pro Asn Ser Gly Leu Ala Thr Ile Met Ser Asp
            420                 425                 430

Gly Ala Gly Gly Asn Lys Trp Met Phe Val Gly Arg Asn Lys Ala Gly
        435                 440                 445

Gln Val Trp Thr Asp Ile Thr Gly Asn Arg Ala Gly Thr Val Thr Ile
    450                 455                 460

Asn Ala Asp Gly Trp Gly Asn Phe Ser Val Asn Gly Gly Ser Val Ser
465                 470                 475                 480
```

```
Ile Trp Val Asn Lys
            485

<210> SEQ ID NO 3
<211> LENGTH: 269
<212> TYPE: PRT
<213> ORGANISM: Bacillus lentus

<400> SEQUENCE: 3

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

<210> SEQ ID NO 4
<211> LENGTH: 269
<212> TYPE: PRT
<213> ORGANISM: Thermomyces lanuginosus

<400> SEQUENCE: 4

Glu Val Ser Gln Asp Leu Phe Asn Gln Phe Asn Leu Phe Ala Gln Tyr
1               5                   10                  15

Ser Ala Ala Ala Tyr Cys Gly Lys Asn Asn Asp Ala Pro Ala Gly Thr
            20                  25                  30

Asn Ile Thr Cys Thr Gly Asn Ala Cys Pro Glu Val Glu Lys Ala Asp
        35                  40                  45
```

```
Ala Thr Phe Leu Tyr Ser Phe Glu Asp Ser Gly Val Gly Asp Val Thr
 50                  55                  60

Gly Phe Leu Ala Leu Asp Asn Thr Asn Lys Leu Ile Val Leu Ser Phe
 65                  70                  75                  80

Arg Gly Ser Arg Ser Ile Glu Asn Trp Ile Gly Asn Leu Asn Phe Asp
                 85                  90                  95

Leu Lys Glu Ile Asn Asp Ile Cys Ser Gly Cys Arg Gly His Asp Gly
            100                 105                 110

Phe Thr Ser Ser Trp Arg Ser Val Ala Asp Thr Leu Arg Gln Lys Val
            115                 120                 125

Glu Asp Ala Val Arg Glu His Pro Asp Tyr Arg Val Val Phe Thr Gly
130                 135                 140

His Ser Leu Gly Gly Ala Leu Ala Thr Val Ala Gly Ala Asp Leu Arg
145                 150                 155                 160

Gly Asn Gly Tyr Asp Ile Asp Val Phe Ser Tyr Gly Ala Pro Arg Val
                165                 170                 175

Gly Asn Arg Ala Phe Ala Glu Phe Leu Thr Val Gln Thr Gly Gly Thr
            180                 185                 190

Leu Tyr Arg Ile Thr His Thr Asn Asp Ile Val Pro Arg Leu Pro Pro
            195                 200                 205

Arg Glu Phe Gly Tyr Ser His Ser Ser Pro Glu Tyr Trp Ile Lys Ser
210                 215                 220

Gly Thr Leu Val Pro Val Thr Arg Asn Asp Ile Val Lys Ile Glu Gly
225                 230                 235                 240

Ile Asp Ala Thr Gly Gly Asn Asn Gln Pro Asn Ile Pro Asp Ile Pro
                245                 250                 255

Ala His Leu Trp Tyr Phe Gly Leu Ile Gly Thr Cys Leu
            260                 265

<210> SEQ ID NO 5
<211> LENGTH: 485
<212> TYPE: PRT
<213> ORGANISM: Bacillus halmapalus

<400> SEQUENCE: 5

His His Asn Gly Thr Asn Gly Thr Met Met Gln Tyr Phe Glu Trp His
 1               5                  10                  15

Leu Pro Asn Asp Gly Asn His Trp Asn Arg Leu Arg Asp Asp Ala Ser
             20                  25                  30

Asn Leu Arg Asn Arg Gly Ile Thr Ala Ile Trp Ile Pro Pro Ala Trp
         35                  40                  45

Lys Gly Thr Ser Gln Asn Asp Val Gly Tyr Gly Ala Tyr Asp Leu Tyr
 50                  55                  60

Asp Leu Gly Glu Phe Asn Gln Lys Gly Thr Val Arg Thr Lys Tyr Gly
 65                  70                  75                  80

Thr Arg Ser Gln Leu Glu Ser Ala Ile His Ala Leu Lys Asn Asn Gly
                 85                  90                  95

Val Gln Val Tyr Gly Asp Val Val Met Asn His Lys Gly Gly Ala Asp
            100                 105                 110

Ala Thr Glu Asn Val Leu Ala Val Glu Val Asn Pro Asn Asn Arg Asn
            115                 120                 125

Gln Glu Ile Ser Gly Asp Tyr Thr Ile Glu Ala Trp Thr Lys Phe Asp
130                 135                 140

Phe Pro Gly Arg Gly Asn Thr Tyr Ser Asp Phe Lys Trp Arg Trp Tyr
145                 150                 155                 160
```

-continued

```
His Phe Asp Gly Val Asp Trp Asp Gln Ser Arg Gln Phe Gln Asn Arg
            165                 170                 175

Ile Tyr Lys Phe Arg Gly Asp Gly Lys Ala Trp Asp Trp Glu Val Asp
            180                 185                 190

Ser Glu Asn Gly Asn Tyr Asp Tyr Leu Met Tyr Ala Asp Val Asp Met
            195                 200                 205

Asp His Pro Glu Val Val Asn Glu Leu Arg Arg Trp Gly Glu Trp Tyr
            210                 215                 220

Thr Asn Thr Leu Asn Leu Asp Gly Phe Arg Ile Asp Ala Val Lys His
225                 230                 235                 240

Ile Lys Tyr Ser Phe Thr Arg Asp Trp Leu Thr His Val Arg Asn Ala
            245                 250                 255

Thr Gly Lys Glu Met Phe Ala Val Ala Glu Phe Trp Lys Asn Asp Leu
            260                 265                 270

Gly Ala Leu Glu Asn Tyr Leu Asn Lys Thr Asn Trp Asn His Ser Val
            275                 280                 285

Phe Asp Val Pro Leu His Tyr Asn Leu Tyr Asn Ala Ser Asn Ser Gly
            290                 295                 300

Gly Asn Tyr Asp Met Ala Lys Leu Leu Asn Gly Thr Val Val Gln Lys
305                 310                 315                 320

His Pro Met His Ala Val Thr Phe Val Asp Asn His Asp Ser Gln Pro
            325                 330                 335

Gly Glu Ser Leu Glu Ser Phe Val Gln Glu Trp Phe Lys Pro Leu Ala
            340                 345                 350

Tyr Ala Leu Ile Leu Thr Arg Glu Gln Gly Tyr Pro Ser Val Phe Tyr
            355                 360                 365

Gly Asp Tyr Tyr Gly Ile Pro Thr His Ser Val Pro Ala Met Lys Ala
            370                 375                 380

Lys Ile Asp Pro Ile Leu Glu Ala Arg Gln Asn Phe Ala Tyr Gly Thr
385                 390                 395                 400

Gln His Asp Tyr Phe Asp His His Asn Ile Ile Gly Trp Thr Arg Glu
            405                 410                 415

Gly Asn Thr Thr His Pro Asn Ser Gly Leu Ala Thr Ile Met Ser Asp
            420                 425                 430

Gly Pro Gly Gly Glu Lys Trp Met Tyr Val Gly Gln Asn Lys Ala Gly
            435                 440                 445

Gln Val Trp His Asp Ile Thr Gly Asn Lys Pro Gly Thr Val Thr Ile
            450                 455                 460

Asn Ala Asp Gly Trp Ala Asn Phe Ser Val Asn Gly Gly Ser Val Ser
465                 470                 475                 480

Ile Trp Val Lys Arg
            485

<210> SEQ ID NO 6
<211> LENGTH: 484
<212> TYPE: PRT
<213> ORGANISM: Bacillus sp.

<400> SEQUENCE: 6

Asn Thr Ala Pro Ile Asn Glu Thr Met Met Gln Tyr Phe Glu Trp Asp
1               5                   10                  15

Leu Pro Asn Asp Gly Thr Leu Trp Thr Lys Val Lys Asn Glu Ala Ala
            20                  25                  30
```

```
Asn Leu Ser Ser Leu Gly Ile Thr Ala Leu Trp Leu Pro Ala Tyr
        35                  40                  45

Lys Gly Thr Ser Gln Ser Asp Val Gly Tyr Gly Val Tyr Asp Leu Tyr
 50                  55                  60

Asp Leu Gly Glu Phe Asn Gln Lys Gly Thr Ile Arg Thr Lys Tyr Gly
 65                  70                  75                  80

Thr Lys Thr Gln Tyr Ile Gln Ala Ile Gln Ala Lys Ala Ala Gly
                 85                  90                  95

Met Gln Val Tyr Ala Asp Val Val Phe Asn His Lys Ala Gly Ala Asp
                100                 105                 110

Gly Thr Glu Phe Val Asp Ala Val Glu Val Asp Pro Ser Asn Arg Asn
            115                 120                 125

Gln Glu Thr Ser Gly Thr Tyr Gln Ile Gln Ala Trp Thr Lys Phe Asp
        130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Ser Thr Gly Lys Ala Trp Asp Trp Glu Val Asp Thr
                180                 185                 190

Glu Asn Gly Asn Tyr Asp Tyr Leu Met Phe Ala Asp Leu Asp Met Asp
            195                 200                 205

His Pro Glu Val Val Thr Glu Leu Lys Asn Trp Gly Thr Trp Tyr Val
        210                 215                 220

Asn Thr Thr Asn Ile Asp Gly Phe Arg Leu Asp Ala Val Lys His Ile
225                 230                 235                 240

Lys Tyr Thr Phe Phe Pro Asp Trp Leu Thr Tyr Val Arg Asn Gln Thr
                245                 250                 255

Gly Lys Asn Leu Phe Ala Val Gly Glu Phe Trp Ser Tyr Asp Val Asn
            260                 265                 270

Lys Leu His Asn Tyr Ile Thr Lys Thr Asn Gly Ser Met Ser Leu Phe
        275                 280                 285

Asp Ala Pro Leu His Asn Asn Phe Tyr Thr Ala Ser Lys Ser Ser Gly
290                 295                 300

Tyr Phe Asp Met Arg Tyr Leu Leu Asn Asn Thr Leu Met Lys Asp Gln
305                 310                 315                 320

Pro Ser Leu Ala Val Thr Leu Val Asp Asn His Asp Thr Gln Pro Gly
                325                 330                 335

Gln Ser Leu Gln Ser Trp Val Glu Pro Trp Phe Lys Pro Leu Ala Tyr
            340                 345                 350

Ala Phe Ile Leu Thr Arg Gln Glu Gly Tyr Pro Cys Val Phe Tyr Gly
        355                 360                 365

Asp Tyr Tyr Gly Ile Pro Lys Tyr Asn Ile Pro Gly Leu Lys Ser Lys
370                 375                 380

Ile Asp Pro Leu Leu Ile Ala Arg Arg Asp Tyr Ala Tyr Gly Thr Gln
385                 390                 395                 400

Arg Asp Tyr Ile Asp His Gln Asp Ile Ile Gly Trp Thr Arg Glu Gly
                405                 410                 415

Ile Asp Thr Lys Pro Asn Ser Gly Leu Ala Ala Leu Ile Thr Asp Gly
            420                 425                 430

Pro Gly Gly Ser Lys Trp Met Tyr Val Gly Lys Lys His Ala Gly Lys
        435                 440                 445
```

Val Phe Tyr Asp Leu Thr Gly Asn Arg Ser Asp Thr Val Thr Ile Asn
450                 455                 460

Ala Asp Gly Trp Gly Glu Phe Lys Val Asn Gly Gly Ser Val Ser Ile
465                 470                 475                 480

Trp Val Ala Lys

<210> SEQ ID NO 7
<211> LENGTH: 485
<212> TYPE: PRT
<213> ORGANISM: Cytophaga sp.

<400> SEQUENCE: 7

Ala Ala Thr Asn Gly Thr Met Met Gln Tyr Phe Glu Trp Tyr Val Pro
1               5                   10                  15

Asn Asp Gly Gln Gln Trp Asn Arg Leu Arg Thr Asp Ala Pro Tyr Leu
                20                  25                  30

Ser Ser Val Gly Ile Thr Ala Val Trp Thr Pro Pro Ala Tyr Lys Gly
            35                  40                  45

Thr Ser Gln Ala Asp Val Gly Tyr Gly Pro Tyr Asp Leu Tyr Asp Leu
50                  55                  60

Gly Glu Phe Asn Gln Lys Gly Thr Val Arg Thr Lys Tyr Gly Thr Lys
65                  70                  75                  80

Gly Glu Leu Lys Ser Ala Val Asn Thr Leu His Ser Asn Gly Ile Gln
                85                  90                  95

Val Tyr Gly Asp Val Val Met Asn His Lys Ala Gly Ala Asp Tyr Thr
            100                 105                 110

Glu Asn Val Thr Ala Val Glu Val Asn Pro Ser Asn Arg Asn Gln Glu
        115                 120                 125

Thr Ser Gly Glu Tyr Asn Ile Gln Ala Trp Thr Gly Phe Asn Phe Pro
130                 135                 140

Gly Arg Gly Thr Thr Tyr Ser Asn Phe Lys Trp Gln Trp Phe His Phe
145                 150                 155                 160

Asp Gly Thr Asp Trp Asp Gln Ser Arg Ser Leu Ser Arg Ile Phe Lys
                165                 170                 175

Phe Arg Gly Thr Gly Lys Ala Trp Asp Trp Glu Val Ser Ser Glu Asn
            180                 185                 190

Gly Asn Tyr Asp Tyr Leu Met Tyr Ala Asp Ile Asp Tyr Asp His Pro
        195                 200                 205

Asp Val Val Asn Glu Met Lys Lys Trp Gly Val Trp Tyr Ala Asn Glu
210                 215                 220

Val Gly Leu Asp Gly Tyr Arg Leu Asp Ala Val Lys His Ile Lys Phe
225                 230                 235                 240

Ser Phe Leu Lys Asp Trp Val Asp Asn Ala Arg Ala Ala Thr Gly Lys
                245                 250                 255

Glu Met Phe Thr Val Gly Glu Tyr Trp Gln Asn Asp Leu Gly Ala Leu
            260                 265                 270

Asn Asn Tyr Leu Ala Lys Val Asn Tyr Asn Gln Ser Leu Phe Asp Ala
        275                 280                 285

Pro Leu His Tyr Asn Phe Tyr Ala Ala Ser Thr Gly Gly Gly Tyr Tyr
290                 295                 300

Asp Met Arg Asn Ile Leu Asn Asn Thr Leu Val Ala Ser Asn Pro Thr
305                 310                 315                 320

Lys Ala Val Thr Leu Val Glu Asn His Asp Thr Gln Pro Gly Gln Ser
                325                 330                 335

Leu Glu Ser Thr Val Gln Pro Trp Phe Lys Pro Leu Ala Tyr Ala Phe
            340                 345                 350

Ile Leu Thr Arg Ser Gly Gly Tyr Pro Ser Val Phe Tyr Gly Asp Met
        355                 360                 365

Tyr Gly Thr Lys Gly Thr Thr Thr Arg Glu Ile Pro Ala Leu Lys Ser
    370                 375                 380

Lys Ile Glu Pro Leu Leu Lys Ala Arg Lys Asp Tyr Ala Tyr Gly Thr
385                 390                 395                 400

Gln Arg Asp Tyr Ile Asp Asn Pro Asp Val Ile Gly Trp Thr Arg Glu
                405                 410                 415

Gly Asp Ser Thr Lys Ala Lys Ser Gly Leu Ala Thr Val Ile Thr Asp
            420                 425                 430

Gly Pro Gly Gly Ser Lys Arg Met Tyr Val Gly Thr Ser Asn Ala Gly
        435                 440                 445

Glu Ile Trp Tyr Asp Leu Thr Gly Asn Arg Thr Asp Lys Ile Thr Ile
    450                 455                 460

Gly Ser Asp Gly Tyr Ala Thr Phe Pro Val Asn Gly Gly Ser Val Ser
465                 470                 475                 480

Val Trp Val Gln Gln
            485

<210> SEQ ID NO 8
<211> LENGTH: 485
<212> TYPE: PRT
<213> ORGANISM: Bacillus sp.

<400> SEQUENCE: 8

His His Asn Gly Thr Asn Gly Thr Met Met Gln Tyr Phe Glu Trp Tyr
1               5                   10                  15

Leu Pro Asn Asp Gly Asn His Trp Asn Arg Leu Asn Ser Asp Ala Ser
            20                  25                  30

Asn Leu Lys Ser Lys Gly Ile Thr Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Ser Gln Leu Gln Ala Ala Val Thr Ser Leu Lys Asn Asn Gly
                85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
        115                 120                 125

Gln Glu Val Thr Gly Glu Tyr Thr Ile Glu Ala Trp Thr Arg Phe Asp
    130                 135                 140

Phe Pro Gly Arg Gly Asn Thr His Ser Ser Phe Lys Trp Arg Trp Tyr
145                 150                 155                 160

His Phe Asp Gly Val Asp Trp Asp Gln Ser Arg Arg Leu Asn Asn Arg
                165                 170                 175

Ile Tyr Lys Phe Arg Gly His Gly Lys Ala Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
    210                 215                 220

-continued

```
Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
            245                 250                 255

Thr Gly Lys Asn Met Phe Ala Val Ala Glu Phe Trp Lys Asn Asp Leu
        260                 265                 270

Gly Ala Ile Glu Asn Tyr Leu Gln Lys Thr Asn Trp Asn His Ser Val
    275                 280                 285

Phe Asp Val Pro Leu His Tyr Asn Leu Tyr Asn Ala Ser Lys Ser Gly
290                 295                 300

Gly Asn Tyr Asp Met Arg Asn Ile Phe Asn Gly Thr Val Val Gln Arg
305                 310                 315                 320

His Pro Ser His Ala Val Thr Phe Val Asp Asn His Asp Ser Gln Pro
            325                 330                 335

Glu Glu Ala Leu Glu Ser Phe Val Glu Glu Trp Phe Lys Pro Leu Ala
        340                 345                 350

Tyr Ala Leu Thr Leu Thr Arg Glu Gln Gly Tyr Pro Ser Val Phe Tyr
    355                 360                 365

Gly Asp Tyr Tyr Gly Ile Pro Thr His Gly Val Pro Ala Met Arg Ser
370                 375                 380

Lys Ile Asp Pro Ile Leu Glu Ala Arg Gln Lys Tyr Ala Tyr Gly Lys
385                 390                 395                 400

Gln Asn Asp Tyr Leu Asp His His Asn Ile Ile Gly Trp Thr Arg Glu
            405                 410                 415

Gly Asn Thr Ala His Pro Asn Ser Gly Leu Ala Thr Ile Met Ser Asp
        420                 425                 430

Gly Ala Gly Gly Ser Lys Trp Met Phe Val Gly Arg Asn Lys Ala Gly
    435                 440                 445

Gln Val Trp Ser Asp Ile Thr Gly Asn Arg Thr Gly Thr Val Thr Ile
450                 455                 460

Asn Ala Asp Gly Trp Gly Asn Phe Ser Val Asn Gly Gly Ser Val Ser
465                 470                 475                 480

Ile Trp Val Asn Lys
            485

<210> SEQ ID NO 9
<211> LENGTH: 483
<212> TYPE: PRT
<213> ORGANISM: Bacillus sp.

<400> SEQUENCE: 9

His His Asn Gly Thr Asn Gly Thr Met Met Gln Tyr Phe Glu Trp Tyr
1               5                   10                  15

Leu Pro Asn Asp Gly Asn His Trp Asn Arg Leu Asn Ser Asp Ala Ser
            20                  25                  30

Asn Leu Lys Ser Lys Gly Ile Thr Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Ser Gln Leu Gln Ala Ala Val Thr Ser Leu Lys Asn Asn Gly
            85                  90                  95
```

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
            115                 120                 125

Gln Glu Val Thr Gly Glu Tyr Thr Ile Glu Ala Trp Thr Arg Phe Asp
130                 135                 140

Phe Pro Gly Arg Gly Asn Thr His Ser Ser Phe Lys Trp Arg Trp Tyr
145                 150                 155                 160

His Phe Asp Gly Val Asp Trp Asp Gln Ser Arg Arg Leu Asn Asn Arg
                165                 170                 175

Ile Tyr Lys Phe Arg Gly Lys Ala Trp Asp Trp Glu Val Asp Thr Glu
            180                 185                 190

Asn Gly Asn Tyr Asp Tyr Leu Met Tyr Ala Asp Ile Asp Met Asp His
            195                 200                 205

Pro Glu Val Val Asn Glu Leu Arg Asn Trp Gly Val Trp Tyr Thr Asn
210                 215                 220

Thr Leu Gly Leu Asp Gly Phe Arg Ile Asp Ala Val Lys His Ile Lys
225                 230                 235                 240

Tyr Ser Phe Thr Arg Asp Trp Ile Asn His Val Arg Ser Ala Thr Gly
                245                 250                 255

Lys Asn Met Phe Ala Val Ala Glu Phe Trp Lys Asn Asp Leu Gly Ala
            260                 265                 270

Ile Glu Asn Tyr Leu Gln Lys Thr Asn Trp Asn His Ser Val Phe Asp
            275                 280                 285

Val Pro Leu His Tyr Asn Leu Tyr Asn Ala Ser Lys Ser Gly Gly Asn
290                 295                 300

Tyr Asp Met Arg Asn Ile Phe Asn Gly Thr Val Val Gln Arg His Pro
305                 310                 315                 320

Ser His Ala Val Thr Phe Val Asp Asn His Asp Ser Gln Pro Glu Glu
                325                 330                 335

Ala Leu Glu Ser Phe Val Glu Glu Trp Phe Lys Pro Leu Ala Tyr Ala
            340                 345                 350

Leu Thr Leu Thr Arg Glu Gln Gly Tyr Pro Ser Val Phe Tyr Gly Asp
            355                 360                 365

Tyr Tyr Gly Ile Pro Thr His Gly Val Pro Ala Met Arg Ser Lys Ile
370                 375                 380

Asp Pro Ile Leu Glu Ala Arg Gln Lys Tyr Ala Tyr Gly Pro Gln His
385                 390                 395                 400

Asp Tyr Leu Asp His Pro Asp Val Ile Gly Trp Thr Arg Glu Gly Asp
                405                 410                 415

Ser Ser His Pro Lys Ser Gly Leu Ala Thr Leu Ile Thr Asp Gly Pro
            420                 425                 430

Gly Gly Ser Lys Arg Met Tyr Ala Gly Leu Lys Asn Ala Gly Glu Thr
            435                 440                 445

Trp Tyr Asp Ile Thr Gly Asn Arg Ser Asp Thr Val Lys Ile Gly Ser
            450                 455                 460

Asp Gly Trp Gly Glu Phe His Val Asn Asp Gly Ser Val Ser Ile Tyr
465                 470                 475                 480

Val Gln Lys

<210> SEQ ID NO 10
<211> LENGTH: 485
<212> TYPE: PRT

<213> ORGANISM: Bacillus sp.

<400> SEQUENCE: 10

```
His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Thr Ala Val Trp Ile Pro Pro Ala Trp
        35                  40                  45

Lys Gly Ala Ser Gln Asn Asp Val Gly Tyr Gly Ala Tyr Asp Leu Tyr
50                  55                  60

Asp Leu Gly Glu Phe Asn Gln Lys Gly Thr Val Arg Thr Lys Tyr Gly
65                  70                  75                  80

Thr Arg Asn Gln Leu Gln Ala Ala Val Thr Ala Leu Lys Ser Asn Gly
                85                  90                  95

Ile Gln Val Tyr Gly Asp Val Val Met Asn His Lys Gly Gly Ala Asp
            100                 105                 110

Ala Thr Glu Trp Val Arg Ala Val Glu Val Asn Pro Ser Asn Arg Asn
        115                 120                 125

Gln Glu Val Ser Gly Asp Tyr Thr Ile Glu Ala Trp Thr Lys Phe Asp
130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Gln Leu Gln Asn Arg
                165                 170                 175

Ile Tyr Lys Phe Arg Gly Asp Gly Lys Gly Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Leu Thr His Val Arg Asn Thr
                245                 250                 255

Thr Gly Lys Asn Met Phe Ala Val Ala Glu Phe Trp Lys Asn Asp Ile
            260                 265                 270

Gly Ala Ile Glu Asn Tyr Leu Ser Lys Thr Asn Trp Asn His Ser Val
        275                 280                 285

Phe Asp Val Pro Leu His Tyr Asn Leu Tyr Asn Ala Ser Arg Ser Gly
290                 295                 300

Gly Asn Tyr Asp Met Arg Gln Ile Phe Asn Gly Thr Val Val Gln Arg
305                 310                 315                 320

His Pro Thr His Ala Val Thr Phe Val Asp Asn His Asp Ser Gln Pro
                325                 330                 335

Glu Glu Ala Leu Glu Ser Phe Val Glu Trp Phe Lys Pro Leu Ala
            340                 345                 350

Cys Ala Leu Thr Leu Thr Arg Asp Gln Gly Tyr Pro Ser Val Phe Tyr
        355                 360                 365

Gly Asp Tyr Tyr Gly Ile Pro Thr His Gly Val Pro Ala Met Lys Ser
370                 375                 380

Lys Ile Asp Pro Ile Leu Glu Ala Arg Gln Lys Tyr Ala Tyr Gly Lys
385                 390                 395                 400
```

```
Gln Asn Asp Tyr Leu Asp His His Asn Met Ile Gly Trp Thr Arg Glu
            405                 410                 415

Gly Asn Thr Ala His Pro Asn Ser Gly Leu Ala Thr Ile Met Ser Asp
            420                 425                 430

Gly Pro Gly Gly Asn Lys Trp Met Tyr Val Gly Arg Asn Lys Ala Gly
            435                 440                 445

Gln Val Trp Arg Asp Ile Thr Gly Asn Arg Ser Gly Thr Val Thr Ile
450                 455                 460

Asn Ala Asp Gly Trp Gly Asn Phe Ser Val Asn Gly Gly Ser Val Ser
465                 470                 475                 480

Ile Trp Val Asn Asn
            485

<210> SEQ ID NO 11
<211> LENGTH: 485
<212> TYPE: PRT
<213> ORGANISM: Bacillus sp.

<400> SEQUENCE: 11

His His Asn Gly Thr Asn Gly Thr Met Met Gln Tyr Phe Glu Trp Tyr
1               5                   10                  15

Leu Pro Asn Asp Gly Asn His Trp Asn Arg Leu Asn Ser Asp Ala Ser
            20                  25                  30

Asn Leu Lys Ser Lys Gly Ile Thr Ala Val Trp Ile Pro Pro Ala Trp
        35                  40                  45

Lys Gly Ala Ser Gln Asn Asp Val Gly Tyr Gly Ala Tyr Asp Leu Tyr
50                  55                  60

Asp Leu Gly Glu Phe Asn Gln Lys Gly Thr Val Arg Thr Lys Tyr Gly
65                  70                  75                  80

Thr Arg Ser Gln Leu Gln Ala Ala Val Thr Ser Leu Lys Asn Asn Gly
            85                  90                  95

Ile Gln Val Tyr Gly Asp Val Val Met Asn His Lys Gly Gly Ala Asp
        100                 105                 110

Ala Thr Glu Met Val Arg Ala Val Glu Val Asn Pro Asn Asn Arg Asn
    115                 120                 125

Gln Glu Val Thr Gly Glu Tyr Thr Ile Glu Ala Trp Thr Arg Phe Asp
130                 135                 140

Phe Pro Gly Arg Gly Asn Thr His Ser Ser Phe Lys Trp Arg Trp Tyr
145                 150                 155                 160

His Phe Asp Gly Val Asp Trp Asp Gln Ser Arg Arg Leu Asn Asn Arg
            165                 170                 175

Ile Tyr Lys Phe Arg Gly His Gly Lys Ala Trp Asp Trp Glu Val Asp
        180                 185                 190

Thr Glu Asn Gly Asn Tyr Asp Tyr Leu Leu Tyr Ala Asp Ile Asp Met
    195                 200                 205

Asp His Pro Glu Val Val Asn Glu Leu Arg Asn Trp Gly Val Trp Tyr
210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
            245                 250                 255

Thr Gly Lys Asn Met Phe Ala Val Ala Glu Phe Trp Lys Asn Asp Leu
        260                 265                 270

Gly Ala Ile Glu Asn Tyr Leu Gln Lys Thr Asn Trp Asn His Ser Val
    275                 280                 285
```

```
Phe Asp Val Pro Leu His Tyr Asn Leu Tyr Asn Ala Ser Lys Ser Gly
        290                 295                 300

Gly Asn Tyr Asp Met Arg Asn Ile Phe Asn Gly Thr Val Val Gln Arg
305                 310                 315                 320

His Pro Ser His Ala Val Thr Phe Val Asp Asn His Asp Ser Gln Pro
                325                 330                 335

Glu Glu Ala Leu Glu Ser Phe Val Glu Glu Trp Phe Lys Pro Leu Ala
            340                 345                 350

Tyr Ala Leu Thr Leu Thr Arg Glu Gln Gly Tyr Pro Ser Val Phe Tyr
        355                 360                 365

Gly Asp Tyr Tyr Gly Ile Pro Thr His Gly Val Pro Ala Met Arg Ser
370                 375                 380

Lys Ile Asp Pro Ile Leu Glu Ala Arg Gln Lys Tyr Ala Tyr Gly Lys
385                 390                 395                 400

Gln Asn Asp Tyr Leu Asp His His Asn Ile Ile Gly Trp Thr Arg Glu
                405                 410                 415

Gly Asn Thr Ala His Pro Asn Ser Gly Leu Ala Thr Ile Met Ser Asp
            420                 425                 430

Gly Ala Gly Gly Ser Lys Trp Met Phe Val Gly Arg Asn Lys Ala Gly
        435                 440                 445

Gln Val Trp Ser Asp Ile Thr Gly Asn Arg Thr Gly Thr Val Thr Ile
450                 455                 460

Asn Ala Asp Gly Trp Gly Asn Phe Ser Val Asn Gly Gly Ser Val Ser
465                 470                 475                 480

Ile Trp Val Asn Lys
                485

<210> SEQ ID NO 12
<211> LENGTH: 351
<212> TYPE: PRT
<213> ORGANISM: Bacillus sp.

<400> SEQUENCE: 12

Tyr Asn Pro Val Thr Glu Asp Leu Tyr His Ser Phe Asp Ser His
1               5                   10                  15

Asp Ala Arg Asn Trp Gln Ile Ser Asp Gly Trp Arg Asn Gly Asp Asp
                20                  25                  30

Phe Phe Gly Cys His Trp Ser Gln Asn Arg Val Asn Phe Asn Arg Gly
            35                  40                  45

Glu Met Glu Leu Ser Leu Arg Thr Asn Tyr Ser Tyr Ser Ala Pro Tyr
50                  55                  60

Asn Tyr Glu Cys Ala Glu Tyr Ala Thr Ser Asn Phe Tyr Gly Tyr Gly
65                  70                  75                  80

Leu Tyr Glu Val Ser Met Lys Pro Ala Asn Val Ser Gly Val Ile Ser
                85                  90                  95

Ser Phe Phe Thr Tyr Thr Gly Pro Ser Tyr Asn Gly Ala Pro Trp Asp
            100                 105                 110

Glu Ile Asp Ile Glu Phe Leu Gly Asn Asp Thr Thr Lys Val Gln Phe
        115                 120                 125

Asn Tyr Tyr Thr Asn Gly Val Gly Gly Asn Glu Ile Ile Tyr Asp Leu
130                 135                 140

Gly Phe Asp Ala Ala Asn Ser Phe Asn Thr Tyr Ala Phe Asp Trp Gln
145                 150                 155                 160
```

```
Glu Asn Tyr Ile Ser Trp Tyr Val Asn Gly Asn Leu Val Ala Thr Ala
                165                 170                 175

Thr Glu Asn Ile Pro Ser Asn Pro Ser Lys Ile Met Met Asn Val Trp
            180                 185                 190

Asn Thr Tyr Gly Ile Asp Glu Trp Ala Gly Ala Tyr Gly Gly Glu Ala
        195                 200                 205

Ala Asn Ala Thr Tyr Glu Trp Val Arg Tyr Thr Pro Asn Asn Gly Asn
    210                 215                 220

Thr Thr Pro Ser Thr Ala Pro Asp Phe Gln Leu Gln Ala Cys Asp Tyr
225                 230                 235                 240

Ser Asp Ser Ser Gly Ile Thr Ser Trp Ser Cys Gly Val Gly Thr Phe
                245                 250                 255

His Ser Ser Asn Trp Ile Lys Phe Asp Ser Val Asp Leu Ser Thr Gly
            260                 265                 270

Tyr Asn Ala Phe Ala Val Ser Tyr Thr Ser Pro Gly Ser Gly Ser Phe
        275                 280                 285

Asp Ile Arg Leu Gly Ser Pro His Gly Gln Arg Ile Gly Thr Val Asn
    290                 295                 300

Tyr Gly Ala Thr Gly Gly Trp Ser Asn Tyr Glu Trp Ser Gly Thr Pro
305                 310                 315                 320

Ser Leu Asp Val Thr Val Arg Gly Ala His Asp Ile Tyr Ile Val Ala
                325                 330                 335

Thr Ser Gly Ala Ala Asn Leu Arg Glu Phe Trp Phe Lys Asn Glu
            340                 345                 350

<210> SEQ ID NO 13
<211> LENGTH: 245
<212> TYPE: PRT
<213> ORGANISM: Bacillus akibai

<400> SEQUENCE: 13

Ala Glu Arg Pro Ile Gly Thr Thr Phe Val Glu Thr Phe Glu Ser Tyr
1               5                   10                  15

Asp Ser Glu Arg Trp Ser Lys Ala Gly Val Trp Thr Asn Gly Gln Met
            20                  25                  30

Phe Asn Ala Thr Trp Tyr Pro Glu Gln Val Thr Phe Ser Asp Gly Lys
        35                  40                  45

Met Lys Leu Gln Ile Asp Lys Glu Asp Asn Glu Thr Ala Ser Pro Pro
    50                  55                  60

Tyr Lys Ala Gly Glu Leu Arg Thr Asn Asp Phe Tyr His Tyr Gly Leu
65                  70                  75                  80

Phe Glu Val Ser Met Lys Pro Ala Lys Ser Thr Gly Thr Val Ser Ser
                85                  90                  95

Phe Phe Thr Tyr Thr Gly Pro Trp Asp Trp Asp Asn Asp Pro Trp Asp
            100                 105                 110

Glu Ile Asp Ile Glu Phe Leu Gly Lys Asp Thr Thr Lys Ile Gln Phe
        115                 120                 125

Asn Tyr Phe Thr Asn Gly Val Gly Gly Asn Glu His Tyr His Glu Leu
    130                 135                 140

Gly Phe Asp Ala Ala Asp Asp Phe Asn Thr Tyr Ala Phe Glu Trp Arg
145                 150                 155                 160

Pro Glu Ser Ile Arg Trp Phe Val Asn Gly Glu Leu Val His Thr Ala
                165                 170                 175
```

```
Thr Glu Asn Ile Pro Gln Thr Pro Gln Lys Ile Met Met Asn Leu Trp
            180                 185                 190

Pro Gly Ile Gly Val Asp Gly Trp Thr Gly Arg Phe Asn Gly Glu Asp
            195                 200                 205

Thr Pro Val Val Thr Gln Tyr Asp Trp Val Lys Tyr Thr Pro Leu Glu
            210                 215                 220

Glu Leu Gly Cys Tyr Asn Glu Lys Asn Lys Tyr Lys Lys Cys Lys
225                 230                 235                 240

Lys Thr Lys Val Lys
            245

<210> SEQ ID NO 14
<211> LENGTH: 222
<212> TYPE: PRT
<213> ORGANISM: Bacillus agaradhaerens

<400> SEQUENCE: 14

His Asn Pro Val Thr Asp Glu Glu Val Tyr His Ser Phe Asn Ser His
1               5                   10                  15

Asp Trp Gln Asn Trp Asn Met Ser Asp Gly Trp Lys Asn Asp Asp Tyr
            20                  25                  30

Phe Phe Gly Cys His Trp Ser Gln Asn Arg Val Asn Phe Tyr Gly Gly
            35                  40                  45

Gln Met Glu Leu Ser Leu Arg Thr Asn Tyr Ser Tyr Ala Pro Pro Tyr
    50                  55                  60

Asn Tyr Glu Cys Ala Glu Tyr Thr Thr Asn Asn Phe Tyr Gly Tyr Gly
65                  70                  75                  80

Leu Tyr Glu Val Ser Met Lys Pro Ala Lys Val Ser Gly Val Ile Ser
                85                  90                  95

Ser Phe Phe Thr Tyr Thr Gly Pro Ser Tyr Asn Gly Ala Pro Trp Asp
            100                 105                 110

Glu Ile Asp Ile Glu Phe Leu Gly Asn Asp Thr Thr Lys Val Gln Phe
            115                 120                 125

Asn Tyr Tyr Thr Asp Gly Val Gly Gly Asn Glu Ile Leu Tyr Asp Leu
        130                 135                 140

Gly Phe Asp Ala Ala Asp Ser Tyr Asn Thr Tyr Ala Phe Asp Trp Gln
145                 150                 155                 160

Glu Asn Tyr Ile Asn Trp Tyr Val Asn Gly Gln Leu Val Ala Thr Ala
                165                 170                 175

Thr Glu Asn Ile Pro Ser Asn Pro Ser Lys Ile Met Met Asn Ile Trp
            180                 185                 190

Asn Thr Tyr Gly Ile Asp Glu Trp Ala Gly Arg Tyr Tyr Gly Glu Asp
            195                 200                 205

Ala Asn Ala Ser Tyr Asn Trp Val Arg Tyr Thr Pro Asn Arg
        210                 215                 220

<210> SEQ ID NO 15
<211> LENGTH: 214
<212> TYPE: PRT
<213> ORGANISM: Bacillus mojavensis

<400> SEQUENCE: 15

Gln Thr Gly Gly Ser Phe Phe Asp Pro Phe Asn Gly Tyr Asn Ser Gly
1               5                   10                  15

Phe Trp Gln Lys Ala Asn Gly Tyr Ser Asn Gly Asn Met Phe Asn Cys
            20                  25                  30
```

-continued

```
Thr Trp Arg Ala Asn Asn Val Ser Met Thr Ser Leu Gly Glu Met Arg
     35                  40                  45

Leu Ala Leu Thr Ser Pro Ser Tyr Asn Lys Phe Asp Cys Gly Glu Asn
 50              55                  60

Arg Ser Val Gln Thr Tyr Gly Tyr Gly Leu Tyr Glu Val Arg Met Lys
 65          70                  75                      80

Pro Ala Lys Asn Val Gly Ile Val Ser Ser Phe Phe Thr Tyr Thr Gly
             85                  90                  95

Pro Thr Asp Gly Thr Pro Trp Asp Glu Ile Asp Ile Glu Phe Leu Gly
             100             105                 110

Lys Asp Thr Thr Lys Val Gln Phe Asn Tyr Tyr Thr Asn Gly Val Gly
         115                 120                 125

Asn His Glu Lys Leu Val Asp Leu Gly Phe Asp Ala Ala Asn Ala Tyr
     130                 135                 140

His Thr Tyr Ala Phe Asp Trp Gln Pro Asn Ser Ile Lys Trp Tyr Val
 145             150                 155                 160

Asp Gly Gln Leu Lys His Thr Ala Thr Ser Gln Ile Pro Thr Thr Pro
             165                 170                 175

Gly Lys Ile Met Met Asn Leu Trp Asn Gly Thr Gly Val Asp Glu Trp
             180                 185                 190

Leu Gly Ser Tyr Asn Gly Val Thr Pro Leu Tyr Ala His Tyr Asp Trp
         195                 200                 205

Val Arg Tyr Thr Lys Lys
         210
```